United States Patent
Fernandes et al.

(10) Patent No.: US 11,367,004 B2
(45) Date of Patent: Jun. 21, 2022

(54) REAL-WORLD EVIDENCE OF DIAGNOSTIC TESTING AND TREATMENT PATTERNS IN U.S. BREAST CANCER PATIENTS WITH IMPLICATIONS FOR TREATMENT BIOMARKERS FROM RNA-SEQUENCING DATA

(71) Applicant: TEMPUS LABS, INC., Chicago, IL (US)

(72) Inventors: Louis Fernandes, Chicago, IL (US); Caroline Epstein, Chicago, IL (US); Joshua S K Bell, Chicago, IL (US); Nike Tsiapera Beaubier, Chicago, IL (US); Gary Palmer, Chicago, IL (US)

(73) Assignee: TEMPUS LABS, INC., Chicago, IL (US)

( * ) Notice: Subject to any disclaimer, the term of this patent is extended or adjusted under 35 U.S.C. 154(b) by 0 days.

(21) Appl. No.: 17/247,509

(22) Filed: Dec. 14, 2020

(65) Prior Publication Data

US 2021/0222259 A1 Jul. 22, 2021

Related U.S. Application Data

(60) Provisional application No. 62/947,431, filed on Dec. 12, 2019.

(51) Int. Cl.
| | |
|---|---|
| *G06N 3/12* | (2006.01) |
| *G16B 5/20* | (2019.01) |
| *G16B 25/00* | (2019.01) |
| *G16B 20/00* | (2019.01) |
| *G16B 30/00* | (2019.01) |
| *C12Q 1/6886* | (2018.01) |

(52) U.S. Cl.
CPC ............. *G06N 3/12* (2013.01); *C12Q 1/6886* (2013.01); *G16B 5/20* (2019.02); *G16B 20/00* (2019.02); *G16B 25/00* (2019.02); *G16B 30/00* (2019.02); *C12Q 2600/106* (2013.01); *C12Q 2600/112* (2013.01); *C12Q 2600/158* (2013.01)

(58) Field of Classification Search
CPC . G06N 3/12; C16B 5/20; G16B 20/00; G16B 25/00; G16B 30/00; C12Q 1/6886
USPC .......................................................... 702/19
See application file for complete search history.

(56) References Cited

U.S. PATENT DOCUMENTS

| | | |
|---|---|---|
| 8,843,356 B2 | 9/2014 | Schadt et al. |
| 2010/0216660 A1 | 8/2010 | Nikolsky et al. |
| 2018/0357374 A1 | 12/2018 | Bagaev et al. |
| 2020/0098448 A1 | 3/2020 | Shah et al. |
| 2020/0395097 A1 | 12/2020 | Chang et al. |

FOREIGN PATENT DOCUMENTS

| | | |
|---|---|---|
| EP | 3369826 A1 | 9/2018 |
| WO | 2013/011479 A2 | 1/2013 |
| WO | 2015/077725 A1 | 5/2015 |

OTHER PUBLICATIONS

Yao et al. "Discordance and Clinical Significance of ER, PR, and HER2 Status between Primary Breast Cancer and Synchronous Axillary Lymph Node Metastasis" Med. Oncol. (2014) vol. 31, No. 798, pp. 1-7. (Year: 2014).*
Loi et al., Pembrolizumab plus trastuzumab in trastuzumab-resistant, advanced, HER2-positive breast cancer (PANACEA): a single-arm, multicentre, phase 1b-2 trial, The Lancet Oncology, 20:371-382 (2019).
Martina et al., The inclusion of real world evidence in clinical development planning, Trials, 19:468 (2018).
McNamara et al., Differential impact of cognitive computing augmented by real world evidence on novice and expert oncologists, Cancer Medicine, 8(15):6578-6584 (2019).
Michuda et al., Transcriptome-based cancer type prediction for tumors of unknown origin, Journal of Clinical Oncology, 37:3081-3081 (2019).
Miksad et al., Harnessing the power of real-world evidence (rwe): a checklist to ensure regulatory-grade data quality, Clinical pharmacology & therapeutics, 103:202-205 (2018).
Nabhan et al., Real-world evidence-what does it really mean?, JAMA Oncology, 5(6):781-783, (2019).
Nahed et al., Ki-67 as a prognostic marker according to breast cancer molecular subtype, Cancer Biology & Medicine, 13(4):496-504 (2016).
Network TCGA, Comprehensive molecular portraits of human breast tumours, Nature, 490:61-70 (2012).
O'Neill et al., 2-Deoxy-D-Glucose inhibits aggressive triple-negative breast cancer cells by targeting glycolysis and the cancer stem cell phenotype, Scientific Reports, 9:3788 (2019).
Pfizer, U.S. fda approves ibrance (Registered) (palbociclib) for the treatment of men with HR+, HER2-metastatic breast cancer, (2019).
Plitas et al., Regulatory T cells exhibit distinct features in human breast cancer, Immunity, 45:1122-1134 (2016).
Przepiorka et al., FDA approval: blinatumomab, Clinical cancer research, 21:4035-4039 (2015).
Quek et al., Clinical outcomes, treatment patterns, and health resource utilization among metastatic breast cancer patients with germline BRCA1/2 mutation: A real-world retrospective study, Advances in Therapy, 36:708-720 (2019).

(Continued)

*Primary Examiner* — Jerry Lin
(74) *Attorney, Agent, or Firm* — Marshall, Gerstein & Borun LLP

(57) ABSTRACT

Techniques are provided for replacing image assays using real world data and real word evidence RNA-seq analysis for assessing biologic pathways for identifying molecular subtypes. Systems of a methods diagnose HER2 status for a patient, by identifying discordant HER2 status result between the HER2 status from immunohistochemistry (IHC) and the HER2 status from fluorescence in-situ hybridization (FISH) and diagnosing HER2 status based gene expression data.

29 Claims, 35 Drawing Sheets
(27 of 35 Drawing Sheet(s) Filed in Color)

(56) References Cited

OTHER PUBLICATIONS

Research FoC, Blueprint for breakthrough: exploring the utility of real world evidence, (RWE) (2016).
Robertson et al., Re-testing of predictive biomarkers on surgical breast cancer specimens is clinically relevant, Breast Cancer Research and Treatment, 174:795-805 (2019).
Sharma et al., HER-2 pulsed dendritic cell vaccine can eliminate HER-2 expression and impact ductal carcinoma in situ, Cancer, 118:4354-4362 (2012).
Shimelis et al., Triple-negative breast cancer risk genes identified by multigene hereditary cancer panel testing, Journal of the National Cancer Institute, 110:855-862 (2018).
Smid et al., Subtypes of breast cancer show preferential site of relapse, Cancer Research, 68:3108-3114 (2008).
Taylor-Stokes et al., Treatment patterns and clinical outcomes among patients receiving palbociclib in combination with an aromatase inhibitor or fulvestrant for HR+/HER2-negative advanced/metastatic breast cancer in real-world settings in the US: Results from the IRIS study, The Breast, 43:22-27 (2019).
Thomas et al., NY-ESO-1 based immunotherapy of cancer: Current perspectives, Frontiers in Immunology, 9:947 (2018).
U.S. patent application filed Dec. 4, 2020, entitled Systems and Methods for Automating RNA Expression Calls in a Cancer Prediction Pipeline, U.S. Appl. No. 17/112,877.
U.S. patent application, titled Data based cancer research and treatment systems and methods, filed Oct. 18, 2019, U.S. Appl. No. 16/657,804.
U.S. patent application, titled Tumor organoid culture compositions, systems, and methods, filed Nov. 22, 2019, U.S. Appl. No. 16/693,117.
U.S. provisional patent application, titled A method and process for predicting and analyzing patient cohort response, progression and survival, filed Dec. 31, 2018, U.S. Appl. No. 62/786,739.
U.S. provisional patent application, titled Adaptive order fulfillment and tracking methods and systems, filed Jul. 12, 2019, U.S. Appl. No. 62/873,693.
U.S. provisional patent application, titled Artificial intelligence assisted precision medicine enhancements to standardized laboratory diagnostic testing, filed Oct. 22, 2019, U.S. Appl. No. 62/924,515.
U.S. Provisional patent application, titled Large scale phenotypic organoid analysis, filed Dec. 5, 2019, U.S. Appl. No. 62/944,292.
U.S. provisional patent application, titled System and method for expanding clinical options for cancer patients using integrated genomic profiling, filed Sep. 19, 2019, U.S. Appl. No. 62/902,950.
U.S. provisional patent application, titled systems and methods for automating RNA expression calls in a cancer prediction pipeline, filed Dec. 4, 2019, U.S. Appl. No. 62/943,712.
U.S. Provisional patent application, titled Systems and methods for next generation sequencing uniform probe design, filed Oct. 21, 2019, U.S. Appl. No. 62/924,073.
U.S. Provisional patent application, titled Systems and methods for predicting therapeutic sensitivity, filed Oct. 22, 2019, U.S. Appl. No. 62/924,621.
U.S. provisional patent application, titled Systems and methods of clinical trial evaluation, filed May 31, 2019, U.S. Appl. No. 62/855,913.
U.S. Provisional patent application, titled Therapeutic suggestion improvements gained through genomic biomarker matching plus clinical history, filed Feb. 12, 2019, U.S. Appl. No. 62/804,724.
U.S. provisional patent application, titled, Calculating cell-type RNA profiles for diagnosis and treatment, filed Oct. 21, 2019, U.S. Appl. No. 62/924,054.
U.S. provisional patent application, titled, Transcriptome deconvolution of metastatic tissue samples, filed Dec. 31, 2018, U.S. Appl. No. 62/786,756.
Vallon-Christersson et al., Cross comparison and prognostic assessment of breast cancer multigene signatures in a large population-based contemporary clinical series, Scientific Reports, 9:12184 (2019).
Von et al., Adjuvant pertuzumab and trastuzumab in early her2-positive breast cancer, New England Journal of Medicine, 377:122-131 (2017).
Wolff et al., Human epidermal growth factor receptor 2 testing in breast cancer: american society of clinical oncology/college of american pathologists clinical practice guideline focused update, Journal of Clinical Oncology, 36:2105-2122 (2018).
Wu et al., Precision medicine based on tumorigenic signaling pathways for triple-negative breast cancer, Oncology letters, 16:4984-4996 (2018).
Zare et al., Implementation of the 2018 american society of clinical oncology/college of american pathologists guidelines on her2/neu assessment by fish in breast cancers: predicted impact in a single institutional cohort, Modern Pathology, 32:1566-1573 (2019).
Zoon et al., Current molecular diagnostics of breast cancer and the potential incorporation of microRNA, Expert Review of Molecular Diagnostics, 9:455-466 (2009).
Administration USFD: <Ibrance (Registered) (palbociclib) capsules, for oral use—Label.pdf>, (2019).
Administration USFD: Framework for the FDA's real-world evidence program, (2018).
Administration USFD: Submitting documents using real-world data and real-world evidence to FDA for drugs and biologies guidance for industry, (2019).
Administration USFD: Use of electronic health record data in clinical investigations: Guidance for industry, (2018).
Administration USFD: Use of real-world evidence to support regulatory decision-making for medical devices: guidance for industry and food and drug administration staff, (2017).
Allott et al., Intratumoral heterogeneity as a source of discordance in breast cancer biomarker classification, Breast Cancer Research, 18:68 (2016).
American Cancer Society. Breast cancer facts & figures 2019-2020, in Society AC (ed) (2019).
Arena et al., ER-/PR+/HER2-breast cancer type shows the highest proliferative activity among all other combined phenotypes and is more common in young patients: Experience with 6643 breast cancer cases, The Breast Journal, 25:381-385 (2019).
Avazpour et al., HOTAIR: A promising long non-coding rna with potential role in breast invasive carcinoma, Frontiers in Genetics, 8:170 (2017).
Ayoub et al., Immunotherapy for HER2-positive breast cancer: recent advances and combination therapeutic approaches, Breast Cancer: Targets and Therapy, 11:53-69 (2019).
Beaubier et al., Clinical validation of the Tempus xO assay, Oncotarget, 9(40):25826-25832 (2018).
Beaubier et al., Clinical validation of the tempus xT next-generation targeted oncology sequencing assay, Oncotarget, 10(24):2384-2396 (2019).
Beaubier et al., Integrated genomic profiling expands clinical options for patients with cancer, Nature Biotechnology, 37:1351-1360 (2019).
Bradford et al., Consensus analysis of whole transcriptome profiles from two breast cancer patient cohorts reveals long non-coding rnas associated with intrinsic subtype and the tumour microenvironment, PLOS ONE, 11:e0163238 (2016).
BreastCancer.org: MammaPrint Test, (2019).
Brueffer et al., Clinical value of rna sequencing-based classifiers for prediction of the five conventional breast cancer biomarkers: a report from the population-based multicenter Sweden cancerome analysis network-breast initiative, JCO Precision Oncology, 2:1-18 (2018).
Cortes-Ciriano et al., A molecular portrait of microsatellite instability across multiple cancers, Nature Communications, 8:15180 (2017).
Cowie et al., Electronic health records to facilitate clinical research, Clinical Research in Cardiology, 106:1-9 (2017).
Craig et al., Genome and transcriptome sequencing in prospective metastatic triple-negative breast cancer uncovers therapeutic vulnerabilities, Molecular Cancer Therapeutics, 12:104-116 (2013).
Daniels et al., Long-term survival in trastuzumab-treated patients with HER2-positive metastatic breast cancer real-world outcomes and treatment patterns in a whole-of-population Australian cohort (2001-2016), Breast Cancer Research and Treatment, 171:151-159 (2018).

(56) References Cited

OTHER PUBLICATIONS

Dawood et al., Prognosis of women with metastatic breast cancer byher2status and trastuzumab treatment: an institutional-based review, Journal of Clinical Oncology, 28:92-98 (2010).
Dekker et al., Reliability of core needle biopsy for determining ER and HER2 status in breast cancer, Annals of Oncology, 24(4):931-937 (2013).
Desantis et al., Breast cancer statistics, CA: A Cancer Journal for Clinicians, 69(6):438-451 (2019).
El-Galaly et al., Routine imaging for diffuse large b-cell lymphoma in first complete remission does not improve post-treatment survival: a danish-swedish population-based study, Journal of Clinical Oncology, 33:3993-3998 (2015).
Elsawaf et al., Triple-negative breast cancer: clinical and histological correlations, Breast Care, 6:273-278 (2011).
Eswaran et al., Transcriptomic landscape of breast cancers through mRNA sequencing, Scientific Reports, 2:264 (2012).
Fehrenbacher et al., Abstract GS1-02: NSABP B-47 (NRG oncology): phase iii randomized trial comparing adjuvant chemotherapy with adriamycin (a) and cyclophosphamide (c) ? weekly paclitaxel (wp), or docetaxel (t) and c with or without a year of trastuzumab (H) in women with node-positive or high-risk node-negative invasive breast cancer (IBC) expressing HER2 staining intensity of IHC 1+ or 2+ with negative FISH (HER2-Low IBC), Cancer Research, 78:GS1-02-GS1-02 (2018).
Fernandes et al., Real-world evidence of diagnostic testing and treatment patterns in U.S. breast cancer patients with implications for treatment biomarkers from RNA-sequencing data, Clinical Breast Cancer, 1-38 (2020).
Fumagalli et al., Transfer of clinically relevant gene expression signatures in breast cancer: from Affymetrix microarray to Illumina RNA-Sequencing technology, 15:1008 (2014).
Gierach et al., Association of adjuvant tamoxifen and aromatase inhibitor therapy with contralateral breast cancer risk among US women with breast cancer in a general community setting, JAMA Oncology, 3:186 (2017).
Gill et al., Improving observational studies in the era of big data, The Lancet, 392:716-717 (2018).
Goss et al., Impact of premenopausal status at breast cancer diagnosis in women entered on the placebo-controlled NCIC CTG MA17 trial of extended adjuvant letrozole, Annals of Oncology, 24(2):355-361 (2013).
Grewal et al., Application of a neural network whole transcriptome-based pan-cancer method for diagnosis of primary and metastatic cancers, JAMA Network Open, 2:e192597 (2019).
Gullo et al., Impact of timing of trastuzumab initiation on long-term outcome of patients with early-stage HER2-positive breast cancer: the "one thousand HER2 patients" project, British Journal of Cancer, 119:374-380 (2018).
Guo et al., Transcriptome sequencing uncovers a three-long noncoding RNA signature in predicting breast cancer survival, Scientific Reports, 6:27931 (2016).
Gyawali et al., Real-world evidence and randomized studies in the precision oncology era: the right balance, JCO Precision Oncology, 1:1-5 (2017).
Gyorffy et al., An integrative bioinformatics approach reveals coding and non-coding gene variants associated with gene expression profiles and outcome in breast cancer molecular subtypes, British Journal of Cancer, 118:1107-1114 (2018).
Hanzelmann et al., GSVA: gene set variation analysis for microarray and RNA-Seq data, BMC Bioinformatics, 14:7 (2013).
Hare et al., mTOR function and therapeutic targeting in breast cancer, American journal of cancer research, 7(3):383-404 (2017).
Harrell et al., Analysis of adjuvant endocrine therapy in practice from electronic health record data of patients with breast cancer, JCO Clinical Cancer Informatics, 1-8 (2017).
Hernandez et al., The adaptable trial and pcornet: shining light on a new research paradigm, Annals of Internal Medicine, 163:635-636 (2015).
Holgado et al., Is there a role for immunotherapy in HER2-positive breast cancer?, npj Breast Cancer, 4:21 (2018).
Institute NC: SEER cancer statistics review 1975-2016 (2019).
International Application No. PCT/US20/64969, International Search Report and Written Opinion, dated Apr. 21, 2021.
International Application No. PCT/US20/64969, Invitation to Pay Additional Fees, dated Feb. 23, 2021.
Iqbal et al., Differences in breast cancer stage at diagnosis and cancer-specific survival by race and ethnicity in the united states, JAMA, 313(2):165-173 (2015).
Jourquin et al., susan g. komen big data for breast cancer initiative: how patient advocacy organizations can facilitate using big data to improve patient outcomes, JCO Precision Oncology, 3:1-9 (2019).
Khozin et al., Real-world data for clinical evidence generation in oncology, Journal of the National Cancer Institute, 109(2017).
Khozin et al., Real-world outcomes of patients with metastatic non-small cell lung cancer treated with programmed cell death protein 1 inhibitors in the year following U.S. regulatory approval, The Oncologist, 24:648-656 (2019).
Liberzon et al., The molecular signatures database hallmark gene set collection, Cell Systems, 1:417-425 (2015).
Alcala et al., Integrative and comparative genomic analyses identify clinically relevant pulmonary carcinoid groups and unveil the supra-carcinoids, Nature Communications, 10:3407 (2019).
Chlon, Machine learning methods for cancer immunology, Dissertation, U Cambridge, 144 (2017).
Hwang, Using network inference to discover molecular pathways underlying cytokine synergism and age-related neurodegeneration, Dissertation, MIT. 90:(2018).
Jahid, Machine learning and graph theoretical approaches toward precise disease classification, prognosis and treatment, Dissertation, UT San Antonio, 117 (2015).
Muraro, et al., An integrative analysis of gene expression and molecular interaction data to identify dys-regulated subnetworks in inflammatory bowel disease, BMC bioinformatics, 17:42 (2016).
Paull et al., A modular master regulator landscape determines the impact of genetic alteration on the transcriptional identify of cancer cells, BioRxiv., 67(2019).
Ramazzotti et al., Multi-omic tumor data reveal diversity of molecular mechanisms that correlate with surivival, Nature Communications, 9:4453 (2018).
Robinson, Integretive clinical genomics of metastatic cancer, Nature, 543:297 (2017).
Ronen, Evaluation of colorectal cancer subtypes and cell lines using deep learning, Life-science-alliance, 2(6):e201900517 (2019).
Vitali et al., Developing a personalome for precision medicine: emerging method that compute interpretable effect sizes from single subject transcriptomes, Briefings in Bioinformatics, 20(3):789-805 (2017).

* cited by examiner

Figure S1

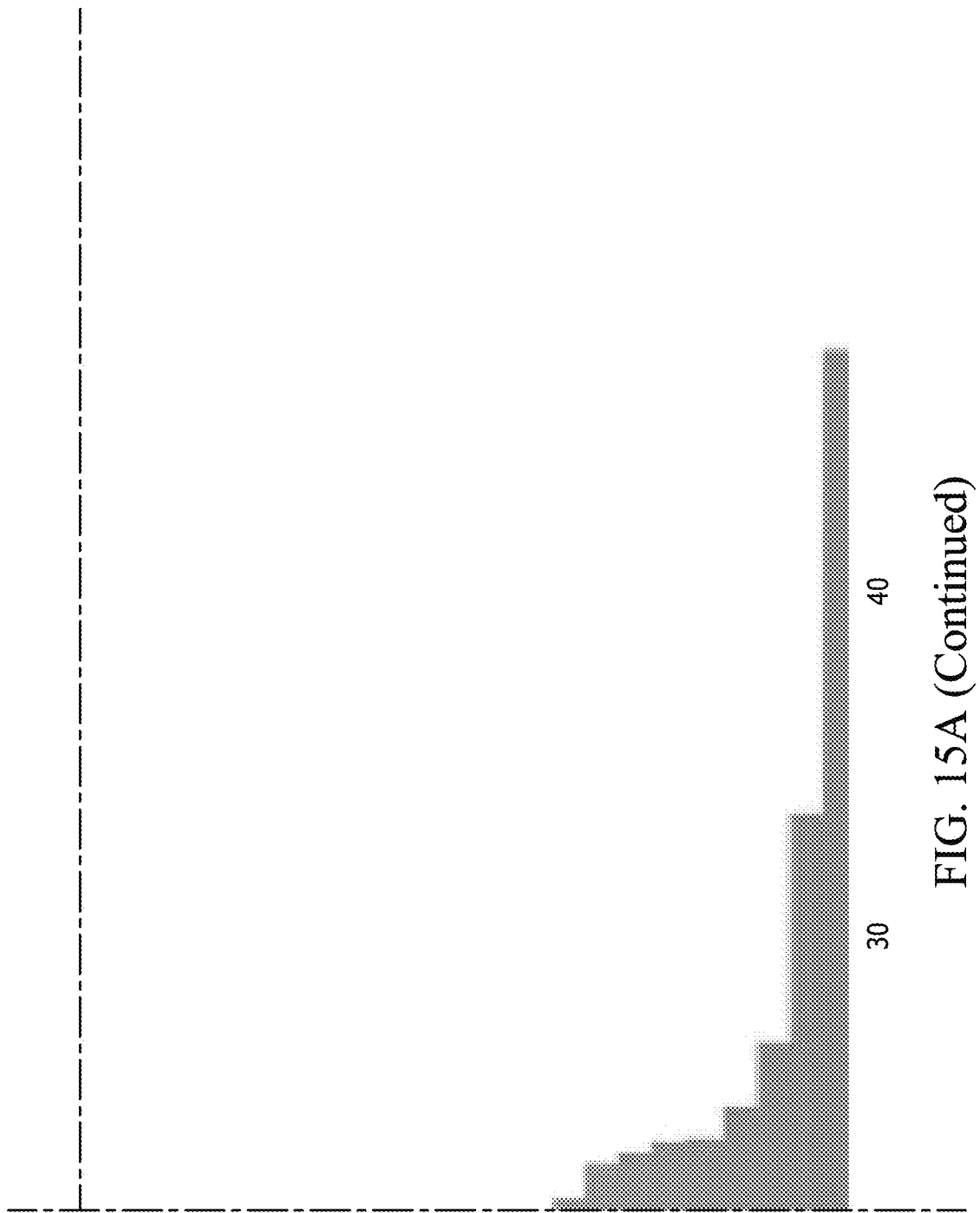

REAL-WORLD EVIDENCE OF DIAGNOSTIC TESTING AND TREATMENT PATTERNS IN U.S. BREAST CANCER PATIENTS WITH IMPLICATIONS FOR TREATMENT BIOMARKERS FROM RNA-SEQUENCING DATA

CROSS-REFERENCE TO RELATED APPLICATIONS

This application claims benefit of priority to and claims under 35 U.S.C. § 119(e)(1) the benefit of the filing date of U.S. provisional application Ser. No. 62/947,431 filed Dec. 12, 2019, the entire disclosure of which is incorporated herein by reference.

FIELD OF THE INVENTION

The present disclosure relates to techniques for the analysis of real world data and/or real word evidence and, more particularly, to techniques for replacing image assays using real world data and real word evidence RNA-seq analysis for assessing biologic pathways for identifying molecular subtypes.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

A growing number of studies have explored real-world data (RWD) and subsequent real-world evidence (RWE) to accelerate treatments for cancer patients. RWD relates to patient information procured during routine care, while RWE is the clinical evidence derived from RWD. The feasibility of this approach has increased alongside technological advances and regulatory support to continuously capture and integrate healthcare data sources. Several studies demonstrate the ability for RWE to guide clinical development strategies, expand product labels, and address knowledge gaps by examining clinical aspects not captured in clinical trials. While limitations for widespread adoption and areas for improvement still exist, RWE has the power to impact patient care.

An essential step towards strengthening RWE validity is demonstrating consistency between population statistics derived from observational RWD and those from controlled, experimental data. Despite the overwhelming support for RWE utility in oncology, technical barriers must be addressed for RWD/RWE to reach its full clinical potential. Incorporating administrative data, ancillary data, and unstructured clinical text from a variety of institutions to generate RWE is a complex task. For example, no standardization exists for abstracting and structuring highly heterogeneous data sources, and many natural language processing algorithms cannot account for these incongruencies. Consequently, clinical endpoints may not be accurately captured and even when data is properly abstracted and prepared for analysis, extraneous variables in raw RWD can introduce confounding biases. Similarly, the integration of omics data with RWD requires a controlled approach for large-scale data analytics.

RWE and integrated omics data have the power to impact patient care. Various studies show the additive value of molecular tumor profiling with RWD for clinically relevant breast cancer insights, but further advancements in the field require the integration of genetic and clinical data from a variety of institutions, along with omics-focused capabilities and data analytics. One potential avenue to augment the value of breast cancer RWD is transcriptomics, as RNA-based gene expression analyses have shown prognostic, predictive, and treatment-directing value beyond DNA-sequencing insights. Whole-transcriptome RNA sequencing (RNA-seq) can help classify cancer types and breast cancer biomarkers, overcoming inconclusive pathology assessments, insufficient tissue quantity, and inter-observer variability of immunohistochemical or in-situ hybridization assays.

A need exists for techniques analyzing real-world evidence of diagnostic testing and treatment pattern analysis in cancer patients, in particular evidence relevant to treatment biomarkers, where such analysis comes from analyzing RNA-sequencing data and/or imaging data, indicating pathway data.

SUMMARY OF THE INVENTION

The present application describes systems and methods addressing the complexities of real world data (RWD) structuring and analyses. Techniques herein demonstrate the feasibility of retrospective RWD analysis and demonstrate that results from clinical studies can be replicated using longitudinal RWD from a large, representative breast cancer cohort. Applying the present techniques with clinical information, such as patient demographics, clinical characteristics, molecular markers, treatment patterns, and overall survival (OS) outcomes, we demonstrate that they are able to uncover discrepancies in real-world testing records, such as HER2 testing records. The present techniques provide for integration of RWD with transcriptomic profiling for clinically relevant insights through analyses of RWD and molecular data. The present techniques are able to augment the value of real world evidence (RWE) by reconciling molecular subtypes, uncovering pathway-driven insights and identifying patients who may benefit from RNA-seq analyses.

In accordance with an example, a computer-implemented method for determining a molecular subtype of a cancer specimen, the method includes: for each of a plurality of pre-determined biological pathways, determining a pathway score using gene expression data of a plurality of nucleic acids associated with the specimen; preparing a summary score for the plurality of biological pathways, based upon the pathway score for each biological pathway; comparing the summary score to one or more enrichment scores each associated with a pre-determined molecular subtype; and returning a determined molecular subtype based on the comparison of the summary score and the one or more enrichment scores.

In some examples, the method includes receiving gene expression data corresponding to a plurality of available biological pathways; and applying a pathway heuristic filter to identify a subset of the available biological pathways, wherein the subset being the pre-determined biological pathways.

In some examples, the pathway heuristic filter is a pathway overlap filter.

In some examples, the method includes filtering the available biologic pathways by applying the pathway overlap filter to identify and filter out pathways having 90% or greater genes in common with a pathway to be retained in the subset.

In some examples, the method includes filtering the available biologic pathways by applying the pathway overlap filter to identify and filter out pathways having 80% or greater genes in common with a pathway to be retained in the subset.

In some examples, the method includes filtering the available biologic pathways by applying the pathway overlap filter to identify and filter out pathways having 50% or greater genes in common with a pathway to be retained in the subset.

In some examples, the pathway heuristic filter is a gene expression data filter.

In some examples, the pathway heuristic filter is a molecular subtype filter.

In some examples, the pathway score for each biological pathway is a z-score.

In some examples, the summary score is an average of the z-scores for the biological pathways.

In some examples, the method includes, before preparing the average of the z-scores, scaling one or more of the z-scores.

In some examples, scaling one or more of the z-scores includes flipping a sign of the one or more z-scores.

In some examples, scaling one or more of the z-scores includes flipping the sign of the one or more z-scores.

In some examples, the method includes flipping the sign of z-scores having a mean negative z-score in a group of positive gene expression samples and having a mean positive z-score in a group of negative gene expression samples.

In some examples, the method includes flipping the sign of z-scores having negative score below a negative threshold or a positive score above a positive threshold.

In some examples, the method includes scaling the pathway score for each of a plurality of biological pathways before determining the summary score.

In some examples, the gene expression data are RNA-seq gene expression data.

In some examples, the pre-determined biological pathways are one or more of the Hallmark pathways.

In some examples, the pre-determined biological pathways are all one or more of the Hallmark pathways.

In some examples, the pre-determined biological pathways are one or more pathways related to estrogen signaling.

In some examples, the pre-determined biological pathways are one or more of pathways downstream of human epidermal growth factor receptor 2 (HER2), downstream of RAS, or downstream of mTOR.

In some examples, the pre-determined biological pathways are one or more immune-related pathways.

In some examples, the pre-determined biological pathways are one or more immune-related Hallmark pathways.

In some examples, the one or more enrichment scores in are determined by UMAP analysis.

In some examples, the determined molecular subtype is a HR+ subtype, a HR+/HER2+ subtype, a HR−/HER2+ subtype, or a HER2− subtype.

In some examples, the determined molecular subtype is a triple negative subtype.

In some examples, the specimen is from a patient diagnosed with breast cancer.

In some examples, the specimen is a breast cancer specimen.

In accordance with another example, a system having a memory and a processor, the memory storing instructions, that when executed, cause the processor to perform any of the foregoing methods.

In accordance with another example, a system having a memory and a processor, the memory storing instructions, that when executed, cause the processor to: for each of a plurality of pre-determined biological pathways, determine a pathway score using gene expression data of a plurality of nucleic acids associated with the specimen; prepare a summary score for the plurality of biological pathways, based upon the pathway score for each biological pathway; compare the summary score to one or more enrichment scores each associated with a pre-determined molecular subtype; and return a determined molecular subtype based on the comparison of the summary score and the one or more enrichment scores.

In accordance with another example, a computer-implemented method of diagnosing HER2 status for a patient, the method includes: obtaining human epidermal growth factor receptor 2 (HER2) status for a specimen from analysis of immunohistochemistry (IHC) image from a first sample of the patient; obtaining HER2 status for a specimen from analysis of fluorescence in-situ hybridization (FISH) image from a second sample of the patient; identifying discordant HER2 status result between the HER2 status from IHC and the HER2 status from FISH; and in response to the identification of discordant HER2 status, diagnosing HER2 status based on at least gene expression data from a third sample of the patient.

In some examples, the method further includes generating a HER2 discordance status report indicating biologic pathways in gene expression data.

In some examples, the method further includes generating a HER2 discordance status report including an indication of a model of molecular subtype gene expression used to identify the discordant HER2.

In some examples, the model of molecular subtype gene expression includes a linear gene expression model.

In some examples, the model of molecular subtype gene expression includes a pathway gene expression model.

In some examples, the method further includes generating the HER2 discordance status report including a listing of pathways identified by the pathway gene expression model.

In some examples, the model of molecular subtype gene expression includes a multiple gene linear regression gene expression model.

In some examples, the method further includes generating the HER2 discordance status report including a listing of genes identified by the multiple gene linear regression gene expression model.

In some examples, the method further includes generating a HER2 discordance status report indicating a molecular subtype determined from the gene expression data.

In some examples, the molecular subtype is a HR+ subtype, a HR+/HER2+ subtype, a HR−/HER2+ subtype, or a HER2− subtype.

In some examples, the molecular subtype is a ER+, ER−, PR+, or PR−.

In some examples, the molecular subtype is a triple negative subtype.

In some examples, the method further includes adjusting a therapeutic treatment protocol based on the patterns in gene expression data.

In some examples, diagnosing HER2 status based on at least gene expression data from a third sample of the patient includes: for each of a plurality of biological pathways in the gene expression data, determining a pathway score; preparing a summary score for the plurality of biological pathways, based upon the pathway score for each biological pathway; and comparing the summary score to one or more enrichment scores each associated with a pre-determined molecular subtype, wherein diagnosing HER2 status based on at least gene expression data from a third sample of the patient includes determining a molecular subtype of the gene expression data as corresponding to the HER2 status, based on the comparison of the summary score and the one or more enrichment scores.

In some examples, obtaining HER2 status from analysis of the immunohistochemistry (IHC) image includes applying the IHC image to a trained IHC classification model, trained with histopathology slide image data to classify HER2 status; and wherein obtaining HER2 status from analysis of the FISH image includes applying the IHC image to a trained FISH classification model, trained with histopathology slide image data to classify HER2 status.

In some examples, the trained IHC classification model and the trained FISH classification model are convolutional neural networks.

In some examples, the method further includes, in response identifying discordant HER2 status result between the HER2 status from IHC and the HER2 status from FISH and diagnosing HER2 status based on at least gene expression data from a third sample of the patient, providing the discordant HER2 status results and the diagnosed HER2 status based on the at least gene expression data to a hybrid classification model.

In some examples, the hybrid classification model includes a convolutional neural network.

In some examples, the first sample, the second sample, and the third sample are from a single biopsy block.

In some examples, the first sample, the second sample, and the third sample are different slices from the biopsy block.

In accordance with another example, a system having a memory and a processor, the memory storing instructions, that when executed, cause the processor to: obtain human epidermal growth factor receptor 2 (HER2) status for a specimen from analysis of immunohistochemistry (IHC) image from a first sample of the patient; obtain HER2 status for a specimen from analysis of fluorescence in-situ hybridization (FISH) image from a second sample of the patient; identify discordant HER2 status result between the HER2 status from IHC and the HER2 status from FISH; and in response to the identification of discordant HER2 status, diagnose HER2 status based on at least gene expression data from a third sample of the patient.

In some examples, the memory includes instructions that when executed cause the processor to generate a HER2 discordance status report indicating biologic pathways in gene expression data.

In some examples, the memory includes instructions that when executed cause the processor to generate a HER2 discordance status report including an indication of a model of molecular subtype gene expression used to identify the discordant HER2.

In accordance with another example, a system having a memory and a processor, the memory storing instructions, that when executed, cause the processor to perform any of the foregoing methods.

BRIEF DESCRIPTION OF THE DRAWINGS

This patent or application file contains at least one drawing executed in color. Copies of this patent or patent application publication with color drawing(s) will be provided by the United States Patent and Trademark Office upon request and payment of the necessary fee.

The figures described below depict various aspects of the system and methods disclosed herein. It should be understood that each figure depicts an example of aspects of the present systems and methods.

FIG. 5A is a plot of the number of patients with positive, negative, or equivocal IHC or FISH test results for ER, PR, HR, and HER2 status at initial diagnosis. FIG. 5B is a plot of the distributions of breast cancer molecular subtypes as determined by abstracted ER, PR, and HER2 test results at initial diagnosis, and FIG. 5C is a plot of the distribution of ER and PR status combinations across the cohort. FIG. 5D is a plot of the number of patients with high, moderate, low, indeterminate, or equivocal Ki67 IHC test results or status-indicating physician notes at initial diagnosis, separated by molecular subtype.

FIG. 8A is a plot of the distribution of patients with variants in the most frequently reported genes across the cohort. The number of patients harboring mutations in each gene are shown above the bars. FIG. 8B is a plot of the number of variants classified as alterations, amplifications, or deletions within each of the most frequently reported genes in the cohort. FIG. 8C is a plot of the distribution of patients with pathogenic germline alterations in NCCN-designated familial high-risk genes and FIG. 8D is a plot of tumor mutational burden (TMB) across the cohort.

FIG. 9A is plot of UMAP transcriptome clustering of 19,147 genes in the cohort color-coded by molecular subtype. Circles correspond to samples with available IHC or FISH test results for all proteins and X symbols correspond to patients with predicted status for at least one protein. FIG. 9B plots relationship between ER, PR, and HER2 receptor status and $\log_{10}$-transformed, normalized gene expression of ESR1, PGR, and ERBB2. Left panels represent samples with available receptor status from abstracted test results, while right panels represent transcriptome-based receptor status predictions. HER2 predictions for samples reported as equivocal are plotted as white dots.

FIG. 10A illustrates specificity and sensitivity and FIG. 10B illustrates precision and recall of transcriptome-based receptor status predictions were evaluated on a testing set comprised of cohort RNA-sequenced samples with abstracted receptor status results in the database. FIG. 10C illustrates confusion matrices depicting transcriptome-based ER, PR, and HER2 status prediction performance.

FIG. 11A illustrates a Pearson correlation between ERBB2 expression and enrichment scores (GSVA) for each HER2-related pathway in MSigDB among the cohort. FIG. 11B illustrates correlation between ESR1 expression and enrichment scores for each ER-related pathway in MSigDB among the cohort.

FIG. 12C is a UMAP of 50 Hallmark enrichment scores. Patients with molecular subtypes based on at least one abstracted receptor status are depicted by circles, while patients with molecular subtypes determined exclusively from RNA-predicted statuses are depicted by X symbols. Distribution of enrichment Z-scores for HR−/HER2+(FIG. 12D) and TNBC (FIG. 12E) relevant pathways are shown.

DETAILED DESCRIPTION OF THE INVENTION

Figure 1:
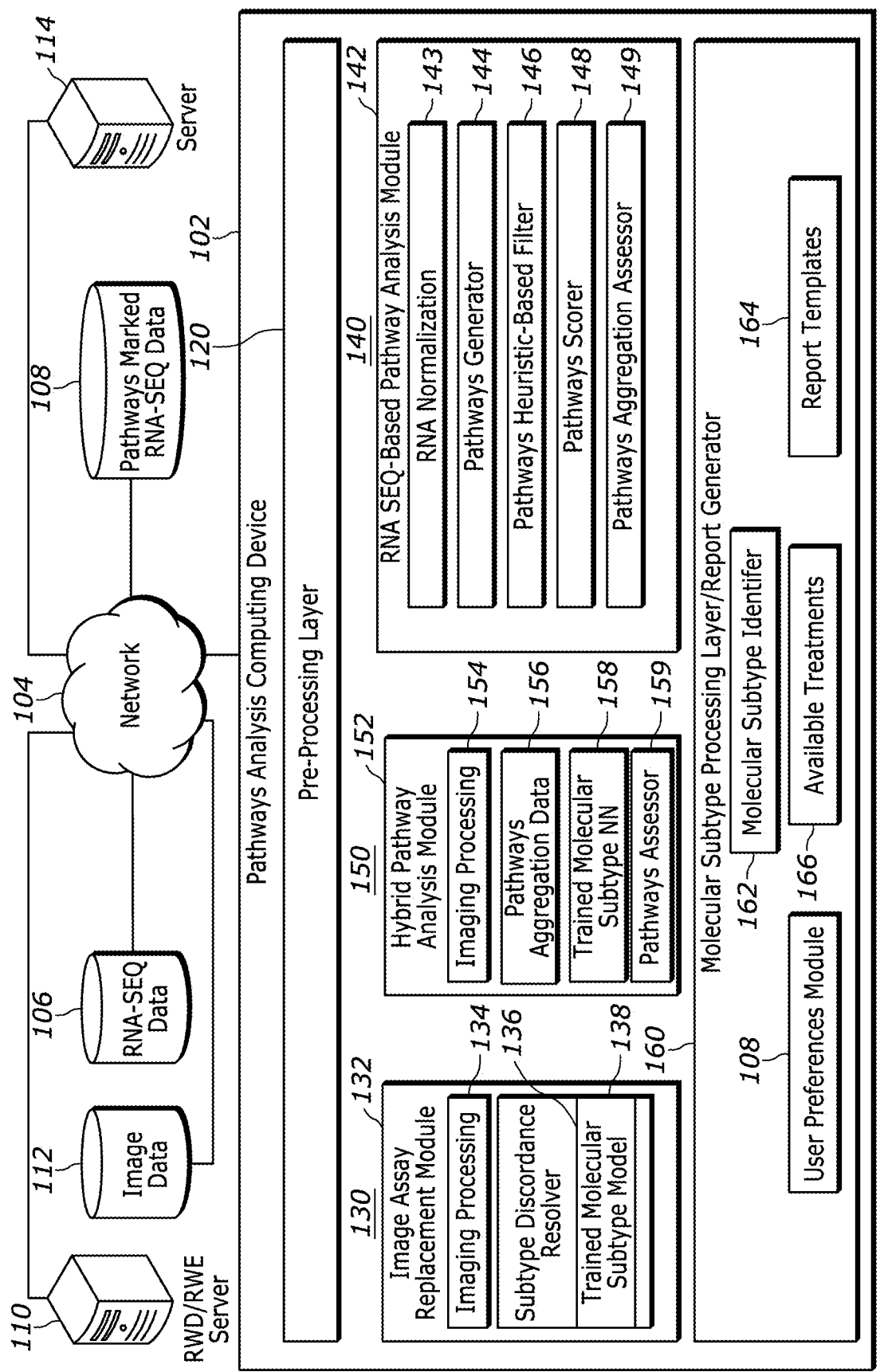
FIG. 1 is a schematic illustration of an example computer processing system for performing biologic pathway analysis on real world data and/or real world evidence, in accordance with an example.

The expanding utility of RWE is evident with the growing number of related studies and regulatory considerations. Compared with randomized controlled trials, however, RWD analyses are complicated by a lack of standardization between records and the introduction of extraneous factors, such as natural language processing errors and uncontrolled confounding variables. In various embodiments, the present application address these concerns by providing systems and methods to 1) increase the statistical power of analyses with a relatively large cohort size, 2) incorporate a variety of data sources beyond electronic health records to benefit downstream analyses, and 3) demonstrate consistency between characteristics of the real-world cohort and results from previous clinical studies.

Using only a portion of breast cancer patient records from the extensive clinicogenomic database, we were able to perform a retrospective analysis using techniques provided herein that provide further evidence for the feasibility and value of generating clinically relevant RWE. We demonstrate that longitudinal RWD can capture key information regarding patient clinical history, treatment journey, and outcomes. RWD analyses, using example techniques herein, generated valid RWE that replicated previously published clinical results and was generally consistent with established databases, indicating feasibility. Although the majority of cohort characteristics were aligned with previous clinical studies, our analyses also highlighted the complexities in breast cancer RWD. For instance, the proportion of pre- and post-menopausal patients was similar to previous clinical trial data, but menopausal status was only confidently abstracted in approximately 51% of the cohort. Upon further review, many RWD breast cancer studies have either applied simplified definitions of menopause, such as an age cutoff, reported missing statuses in electronic records, or did not include menopausal status at all. Advantageously, in various embodiments, the present techniques allow for integration of simplifying rules for abstraction that fill in such gaps in RWD, such as in defining real-world progression-free survival, but can also affect the validity of conclusions.

In various embodiments, to strengthen the validity of RWE presented here, rules were established and applied to perform relevant analyses and to derive statistics from sample cohorts. In various embodiments, techniques herein include applying biologic pathway analysis techniques that facilitate the definition of molecular subtypes from multiple abstracted test results. For example, applying techniques herein to an HER2 test result analyses confirmed the existing conflict in standard testing interpretations, an issue evident by recent American Society of Clinical Oncology (ASCO) guidelines, previous clinical studies, and meta-analyses. Specifically, our findings of IHC intra-test discordance illustrate the subjectivity of IHC testing, prompting standard testing improvements and biomarker discovery.

Upon observation of discrepancies in abstracted HER2 testing results, a separate cohort with complete biopsy data was selected to test the efficacy of a whole-transcriptome model in predicting molecular subtypes. By combining clinical and molecular data with the techniques herein, we demonstrate that transcriptome profiling is complementary to RWD and can illuminate fundamental biological differences between patients. RNA-seq may supplement standard testing interpretations by providing clinically relevant insights when biopsy test data is inconclusive, exemplified here in the resolution of molecular subtypes for patients with equivocal statuses. In various embodiments, equivocal statuses can be avoided and appropriate molecular subtypes identified to inform better treatment decision making, for example, better breast cancer treatment decision making.

Furthermore, as discussed further in examples below, applying the present techniques in various embodiments, we demonstrate that our signaling pathway investigation heretofore uncovered potential pathway-related therapeutic targets, such as oncogenic signaling via the mTOR pathway, for subtypes like TNBC with limited pharmacotherapies available. Further, the present pathway analyses can also elucidate treatment-related tumor characteristics not captured by standard diagnostic and prognostic tests, such as additional biomarkers or amplifications that may be targetable in HER2+ breast cancer patients. Expression-based immune signatures can also predict response to neoadjuvant treatment with several experimental agents/combinations added to standard chemotherapy, including the addition of pembrolizumab in early-stage TNBC. Biomarker selection of immunotherapy in early-stage TNBC will become imperative to therapeutic strategies given its substantial toxicity.

In various embodiments, the present techniques therefore provide data pipelines that integrate longitudinal RWD and comprehensive molecular sequencing data into a structured clinicogenomic database capable of generating valid clinical evidence in real-time. While RWD are inherently complex, cancer cohort selection and data insights are feasible using structured data sources and strictly defined analysis criteria. As we have discovered, integrating RNA-seq data with RWD can improve clinically actionable evidence related to clinical markers, potential therapeutic targets, and optimal therapy selection in breast cancer.

FIG. 1 illustrates a system 100 for performing biologic pathways analysis and molecular subtype determination from analysis of (i) imaging data, such as fluorescence in-situ hybridization (FISH), hematoxylin & eosin stain (H&E), or immunohistochemistry (IHC) image data as well as imaging assay results obtained from such images, (ii) gene expression data, such as RNA-SEQ data, or (iii) a combination thereof. In the illustrated example, the system 100 includes a pathways analysis computing device 102 communicatively coupled, through a communication network 104, to a plurality of data sets and data sources. For example, the computing device 102 may be configured to receive gene expression data from a multitude of different sources through the network 104. The computing device 102, for example, may be coupled to a network-accessible RNA-SEQ database (or dataset) 106, where such gene expression data may or may not be marked with pathways. The computing device 102 may be coupled to a network-accessible RNA-SEQ database 108 that does include already-marked pathways. In some examples, either of these databases 106 and 108 may include gene expression datasets that have been pre-normalized or formatted in accordance with a predetermined normalization protocol. In some examples, either of these databases 106 and 108 is no normalized prior to receipt at the computing device 102. As used herein the term biologic pathways is also referenced simply as "pathways," and includes genetic pathways, cellular pathways, signal transduction pathways, and metabolic pathways.

The computing device 102 may be communicatively coupled to other sources of gene expression data such as a RWD/RWE server 110, which may include gene expression data and other data collected in clinical settings as may be contained in a research institution computing system, lab computing system, hospital computing system, physician group computing system, electronic health records, patient generated health data mobile devices and wearables and mobile apps, observational study systems, patient/disease state registries etc., that makes available stored gene expression data in the form of RNA sequencing dataset.

The computing device 102 may be communicatively coupled to a histopathology image data repository 112. Any number of histopathology image data sources could be accessible using the computing device 102. The histopathology images may be images captured by any dedicated digital medical image scanners, e.g., any suitable optical histopathology slide scanner including 10× and/or 40× resolution magnification scanners. In yet other examples, images may be received from a genomic sequencing system, e.g., the TOGA and NCI Genomic Data Commons or other source of gene expression data. Further still, the histopathology image data repository 112 may be from an organoid modeling lab. These image sources may communicate image data, image assay results data, genomic data, patient data, treatment data, historical data, or other RWD/RWE data, in accordance with the techniques and processes described herein. Each of the image sources may represent multiple image sources. Further, each of these image sources may be considered a different data source, those data sources may be capable of generating and providing imaging data that differs from other providers, hospitals, etc. The imaging data between different sources potentially differs in one or more ways, resulting in different data source-specific bias, such as in different dyes, biospecimen fixations, embeddings, staining protocols, and distinct pathology imaging instruments and settings.

While the server 110 is specifically labeled as a RWD and/or RWE server, as will be appreciated, any of the data sources 106, 108, 110, and 112 may be considered as containing RWD and/or RWE datasets.

The functions of the computing device 102 may be implemented across distributed computing devices connected to one another through a communication link. The functionality of the system 100 may be distributed across any number of devices, including a portable personal computer, smart phone, electronic document, tablet, and desktop personal computer devices shown. In some examples, some or all of the functionality of the computing device 102 may be performed at a network accessible server 114 coupled to the network 104. The network 104 may be public networks such as the Internet, a private network such as that of research institution or a corporation, or any combination thereof. Networks can include, local area network (LAN), wide area network (WAN), cellular, satellite, or other network infrastructure, whether wireless or wired. The networks can utilize communications protocols, including packet-based and/or datagram-based protocols such as Internet protocol (IP), transmission control protocol (TCP), user datagram protocol (UDP), or other types of protocols. Moreover, the networks can include a number of devices that facilitate network communications and/or form a hardware basis for the networks, such as switches, routers, gateways, access points (such as a wireless access point as shown), firewalls, base stations, repeaters, backbone devices, etc.

In the illustrated example, the computing device 102 is configured having a pipeline configuration, showing three different pathway analysis pipelines. An initial pre-processing 120 is provided for gene expression data pre-processing as described in various embodiments herein.

A first pipeline 130 contains an image assay replacement analysis module 132 that receives histopathology image data (including, for example, image assay results data) from the pre-processing layer 120. The image-based module 132 includes an image processing stage 134 and a trained molecular subtype model 136, for example, a model trained to classify the presence of one or more molecular subtypes from RWD/RWE, such as image assay results, i.e., determined based analysis of histopathology image data. A subtype discordance resolver 138 receives the molecular subtype data determined from different images and determines if there is agreement or discordance therebetween. For example, as discussed further below, the trained molecular subtype model 136 may be trained to identify proteins associated with breast cancer in both IHC image data and FISH image data. Yet, as discussed further below, often molecular subtype determinations in IHC image data do not match the molecular subtype determinations from FISH image data. The subtype discordance resolver is capable of comparing the resulting molecular subtypes, determining when there is discordance, including for example when the data is equivocal, and determines if another pipeline process, such as pipeline 140 or pipeline 150 should be used to resolved the discordance.

In contrast to the image assay replacement determination of pipeline 130, a second pipeline 140 performs pathway analysis on gene expression data only. In the illustrated example, the pipeline 140 includes an RNA-seq pathway analysis module 142 having an RNA normalization stage 143, a pathways generator stage 144, a pathways heuristic-based filter stage 146, a pathways scorer stage 148, and a pathways aggregation assessor 149.

A third pipeline 150 forms a hybrid process configured to perform pathway analysis on a combination of histopathology imaging data (including imaging assay results data) and gene expression data. In the illustrated example, the third pipeline 150 includes a hybrid pathway analysis module 152 that includes an imaging processing stage 154, RNA-seq-based pathway aggregation data 156, for example, obtained from the module 142, a trained molecular subtype neural network 158, and a pathways assessor stage 159.

Each of the pipelines 130, 140, and 150 coupled to send their respective pathways analyses data to a molecular subtype processing layer 160, which in the illustrated example, is further configured as a report generator layer. The molecular subtype processing layer 160 contains a molecular subtype identifier 162 that compares the pathway summary scores, received from one or more of the pipelines 130, 140, and 150, to enrichment scores for candidate groups of molecular subtypes stored within the layer 160 or accessible thereto. From this comparison, the identifier 162 determines a predicted molecular subtype(s) and provides that subtype(s) to a report template generator 164. In some examples, the identifier 162 may access available treatment/therapy options 166 corresponding to the determined molecular subtype and provide that additional information to the report generator 164. A user preferences module 168 is further provided to store user settable preferences, for example those entered to the computing device 102 via display and graphical user interface. Example user preferences include report templates, rankings of available treatments, molecular subtype identifier rules predetermined by the user, etc.

Figure 2:
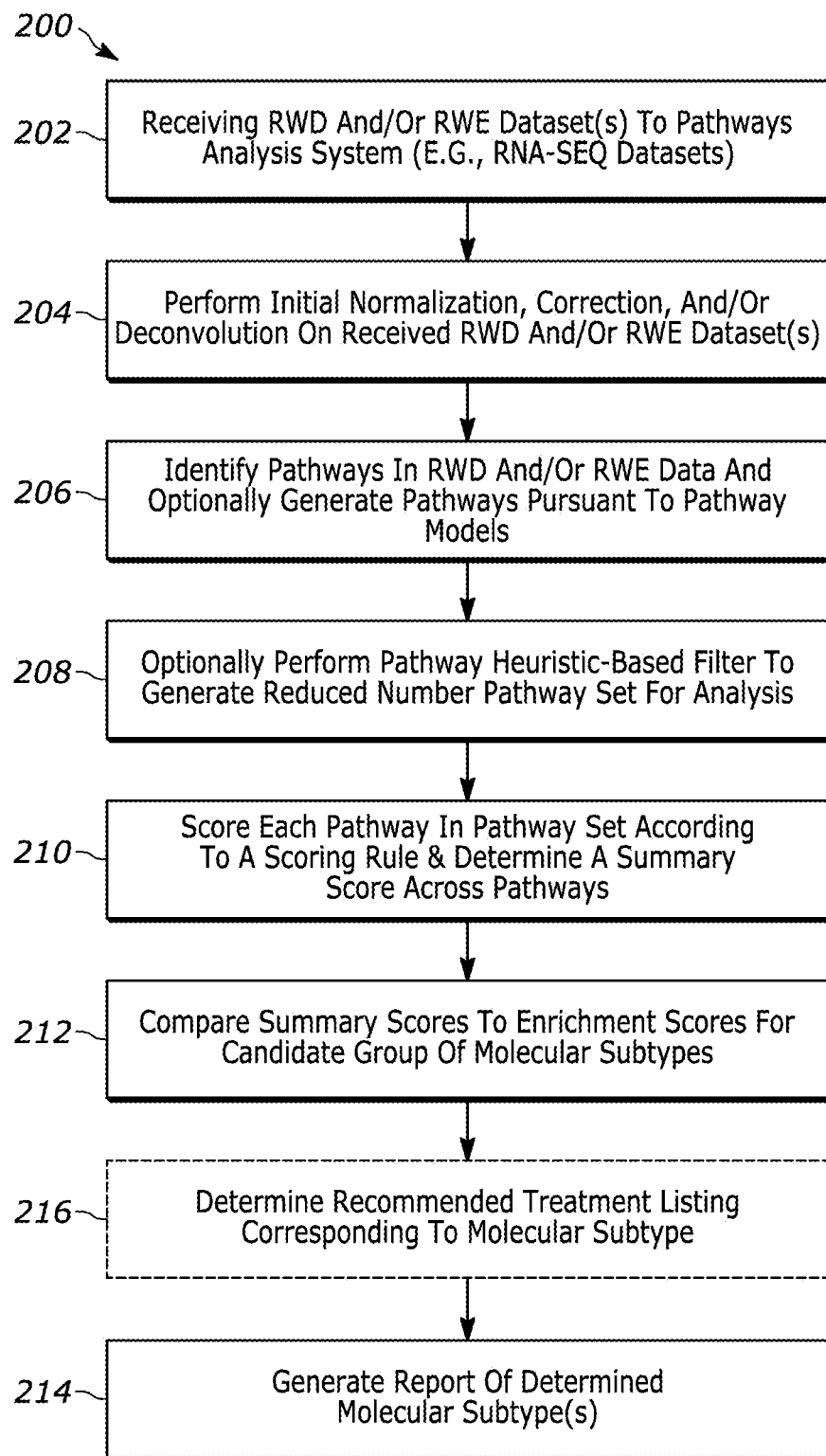
FIG. 2 is a block diagram of an example process for performing pathway analysis and molecular subtype identification from gene expression data as performed by the processing system of FIG. 1, in accordance with an example.

FIG. 2 illustrates an example process 200 of pathway analysis of RWD data, in particular gene expression data, as may be performed by the computing device 102 and in particular by the RNA-seq-based pathway analysis module 142. At a block 202, RWD or RWE data in the form of gene expression data, e.g., RNA-seq data is received to a pathways analysis system. In the example of the FIG. 1, such data may be received from the RNA-seq datasets 106 and/or 108, or the server 110, for example.

In various embodiments, a block 204 is provided and performs a normalization process on the received RNA-seq data. Thus, as illustrated in FIG. 1, the pipeline 140 may include an RNA-seq data normalizer, for example, as disclosed in U.S. patent application Ser. No. 16/581,706, titled "Methods of Normalizing and Correcting RNA Expression Data", and filed Sep. 24, 2019, which is incorporated herein by reference and in its entirety for all purposes. In some examples, the block 204 performs a transcriptomic data deconvolution process, for example, as disclosed in U.S. Prov. Patent Application No. 62/786,756, titled "Transcriptome Deconvolution of Metastatic Tissue Samples", and filed Dec. 31, 2018, and U.S. Prov. Patent Application No. 62/924,054, titled "Calculating Cell-type RNA Profiles for Diagnosis and Treatment", and filed Oct. 21, 2019, which are incorporated herein by reference and in their entirety for all purposes. The deconvoluted information may then be passed on to other aspects of the platform, such as variant calling, RNA expression calling, or insight engines.

In various embodiments, the block 204 may normalize the newly obtained gene expression (e.g., RNA-seq) dataset, to eliminate biases caused by, for example, gene content (GC), gene length, and sequencing depth. Conversion factors may be generated by comparing the obtained gene expression dataset to a standard gene expression dataset using a statistical mapping model. Examples of statistical mapping model include, but are not limited to, a standard linear model, a generalized linear model (using for example a gamma distribution of counts data), or non-parametric methods, such as data transformation into ranks.

For example, the gene expression dataset from the block 202 may contain RNA-seq data. A gene information table containing information such as gene name and starting and ending points (to determine gene length) and gene content ("GC") may be accessed by the block 202 and the resulting information used to determine sample regions for analyzing the gene expression dataset. From there, the block 204 may perform additional normalizations. For instance, a GC content normalization may be performed using a first full quantile normalization process, such as a quantile normalization process like that of the R packages EDASeq and DESeq normalization processes (Bioconductor, Roswell Park Comprehensive Cancer Center, Buffalo, N.Y., available at https://bioconductor.org/packages/release/bioc/html/DESeq.html). The GC content for the sampled data may then be normalized for the gene expression dataset. Subsequently, a second, full quantile normalization may be performed on the gene lengths in the sample data. To correct for sequencing depth, a third normalization process may be used that allows for correction for overall differences in sequencing depth across samples, without being overly influenced by outlier gene expression values in any given sample. For example, a global reference may be determined by calculating a geometric mean of expressions for each gene across all samples. A size factor may be used to adjust the sample to match the global reference. A sample's expression values may be compared to a global reference geometric mean, creating a set of expression ratios for each gene (i.e., sample expression to global reference expression). The size factor is determined as the median value of these calculated ratios. The sample is then adjusted by the single size factor correction in order to match to the global reference, e.g., by dividing gene expression value for each gene by the sample's size factor. The entire GC normalized, gene length normalized, and sequence depth corrected RNA-seq data may be stored as normalized RNA-seq data. A correction process may then be performed on the normalized RNA-seq data, by sampling the RNA-seq data numerous times, and performing statistical mapping or applying a statistical transformation model, such as a linear transformation model, for each gene. Corresponding intercept and beta values may be determined from the linear transformation model and used as correction factors for the RNA-seq data.

In some examples, to incorporate multiple datasets, the block 204 performs gene expression batch normalization processes that adjust for known biases within the dataset including, but not limited to, GC content, gene length, and sequencing depth.

In various embodiments, the process 204 may additionally perform a deconvolution process that receives normalized gene expression data and modifies the data using a clustering process to optimize the number of clusters, K, such that one or more gene expression clusters associated with one or more cell types of interest are detected. Subsequent analysis of the gene expression clusters may determine cancer-specific cluster types within such data.

Deconvoluted gene expression data may be used in downstream gene expression data analyses and may yield more accurate results than analyzing mixed sample gene expression data. For example, analyses of the mixed sample gene expression data may return results that reflect the background tissue instead of the cancer tissue in the mixed sample. Such deconvolution may be beneficial for downstream gene expression data analyses including the pathway analyses that determine which genes are overexpressed or underexpressed along different pathways for determining consensus molecular subtypes, predicting a cancer type present in the sample (especially for tumors of unknown origin), detecting infiltrating lymphocytes, determining which cellular activity pathways are dysregulated, discovering biomarkers, matching therapies or clinical trials based on the results of any of these downstream analyses, and designing clinical trials or organoid experiments based on the results of any of these downstream analyses.

Additional normalization processes at block 204 include normalizing RNA-seq data to account for technical differences between data sets, such as to normalize for the assay used (polyA/exome-capture), for the probe set used for capture, for the sequencer used, and/or for the flow cell. Further examples and discussions of normalization processes that may be performed by the block 204 include those described in U.S. patent application Ser. No. 17/112,877, filed Dec. 4, 2020, entitled "Systems And Methods For Automating RNA Expression Calls In A Cancer Prediction Pipeline" and U.S. patent App. Serial No. filed Sep. 24, 2019, entitled "Methods Of Normalizing And Correcting RNA Expression Data", both of which are hereby incorporated by reference in their respective entireties for all purposes.

One or more of these processes of block 204 may be performed in the RNA normalizer 143 of the pipeline 140 or in the pre-processing layer 120.

In some implementations, the received gene expression data will include pathway data, for example, contained in the RNA-seq dataset 108. In some implementations, the gene expression data will not contain pathway data, such as with the RNA-seq dataset 106. Therefore, a block 206 is provided for identifying pathway data in the received and normalized gene expression data. The number of identified pathways may be small, 1-10, 10-100, 100-1000, 1000-10000, or great than 100000.

If no pathway data is provided, then the block 206 may apply one or more pathway models to the gene expression data to generate pathways. In some example, the block 206 may even identify the presence of existing pathway data, determine whether the existing pathway data meets a predetermined criteria, and if the data does not then apply new pre-authorized pathway models to reconstruct pathway data from the dataset. The block 206, which may be executed by the pathway generator 146 in pipeline 140, may apply suitable pathway models, such as a Hallmark pathway model, immune-related Hallmark pathways model, related estrogen signaling model, downstream HER2 model, downstream RAS model, downstream of mTOR model, and/or immune-related pathways model. The block 206 may be configured to apply which model is selected by a user, for example, stored in the user preferences module 168. In various embodiments, the block 206 is configured to generate a sufficiently large number of diverse pathways for meaning aggregation in processes to follow.

The pathways may be determined (or previously determined) using gene set enrichment analysis GSEA, single sample gene set enrichment analysis (ssGSEA), or another analyses. The pathways may differ in genes, gene ranking, gene expressions, and nodes according to pathway activity. The pathways may correspond to different cancers or different cancer subtypes. In various embodiments, the pathways may correspond to signaling pathway activity (MAPK, RAS, NOTCH), immune features (inflammation, cytokine signaling), tumor microenvironment (hypoxia, angiogenesis), over-expression of a gene (leveraging its downstream effects on other genes' expression), etc.

With pathways identified from the process 204, a process block 208 optionally performs an heuristic-based filtering on the pathways to generate a reduced pathway set for scoring and aggregation analysis. In some embodiments, the process 208 compares pathways and determines if any pathways overlap (for example, have included genes in common) by a threshold amount or percentage. If two or more pathways overlap by a sufficient amount, then the process 208 determine which pathway should remain in the reduced pathway set and then eliminate the other pathways. For example, the process may retain the pathway with the greatest pathway length or the pathway with the greatest amount of biologic expression (gene expression, protein expression, cellular expression). In some examples, the process 208 may filter pathways to minimize gene set overlap or to ensure there is no overlap. The process 208 may filter the pathways for analysis based on other heuristics, such as only identifying upregulating pathways, i.e., pathways exhibiting biologic expression, or only identifying downregulating pathways, i.e., pathways of suppression of biologic expression. Other example heuristic include filtering pathways based on the amount of upregulation or the amount of downregulation. For example, pathways with downregulation amounts greater than a threshold value may be removed. Other example heuristics including filtering pathways based on an pre-assigned molecular subtype, such as filtering to include on pathways previously determined to be associated with HER2+ or HER2−. Other example heuristics include filtering pathways that including be upregulation and downregulation in the same pathway. In some examples, filtering may be based on requiring a pathway to have scores that are significantly different (e.g., p<0.05 by a Wilcoxon) among known positives (by e.g. HER2 IHC/FISH) or negatives. In some examples, pathways could be required to have a mean fold difference (e.g., 1.5) between known positives and negatives. In the example of FIG. 1, the process 208 may be performed by a pathways heuristic filter stage 148.

In the illustrated example of FIG. 2, with the set of pathways for analysis determined, a process 210 performs a scoring of each pathway according to a scoring rule. In some examples, a pathway score is used that ranks the genes in a pathway. In some examples, the scoring is performed by determining z-score for each pathway. The z-score is a difference between a mean of the gene expression values forming a known pathway (a reference gene expression) and a mean of gene expression values in a RNA-seq dataset, for example, after normalization. In various embodiments, the reference gene expression for a pathway is represented by one or more enrichment scores for the pathway, indicating an upregulation or downregulation of gene expression for the pathway. In this way, enrichment scores are associated with pre-determined molecular subtypes, in various embodiments. The reference pathways may be obtained from known databases of pathways and their gene sets. Generally speaking, z-score for a pathway is an example scoring metric capable of taking into account directional effects of one or more molecules on a process and the direction of change of those molecules in a dataset, e.g., upregulation or downregulation of those molecules. The z-score metric is able to predict activation or inhibition of regulators based on relationships with dataset genes and direction of change of dataset genes. For example, a positive z-score indicates that genes in that pathway are upregulated relative to the mean, while a negative z-score indicates that genes in that pathway are downregulated relative to the mean. By way of example only, a positive z-score pathways may in some examples indicate a pathway associated with a gene expression that indicates a HER2+ molecular subtype, and a negative z-score may indicate a pathway associated with gene expression inhibition indicating a HER2− molecular subtype. While various examples are described with reference to a z-score, the process 210 may apply any number of pathway scoring rules, such as for example a quantile normalization or a machine learning algorithm (MLA), that exhibit similar characteristics as z-scores.

In various embodiments, the process 210 further may apply a scaling to allow for summary aggregation of the pathway scores without having the positive and negative scores cancel over a mean gene expression level. The scaling applied by process 210 may be pathway level scaling or gene expression level scoring. For pathway level scaling, for example, the process 210 may identify all pathways having a negative z-score in the majority of patients/specimens in the training data having a HER2− status (negative controls), or a mean negative z-score in the negative controls and flip the sign of the pathway z-score to positive. For each pathway there may be a range of z-scores that are negative and a range that are positive for a set of patients. In some examples, scaling may include flipping a z-score having a mean negative z-score in positive samples and flipping a z-score having a mean positive z-score in negative samples. In some examples, the process 210 may identify those pathways with a negative score below a threshold value and flip the sign of only those pathways or change the scoring value of those pathways to the threshold value. For example, the process 210 may be configured to assign z-scores that are greater than zero, 0, or z-scores that within a range, for example −2<z-score <+2. In another example, all pathway names including HER2 and do (for downregulated) have their signs flipped. In other examples, scaling may be performed to reduce the amount of skew in the distribution of the pathway scores. For gene expression level scaling, gene expression levels, which may vary, may be scaled based on reference gene expression levels for training data. Such scaling may be based on z-scores, quantile normalization, or other scoring modalities.

In various embodiments, the process 210 further performs an aggregation of the pathway scores to determine an aggregated score across the entire reduced pathway set. For example, the process 210 may determine an average of the z-scores across all pathways, after a scaling process. In some examples, the aggregation is performed on the z-scores without performing a scaling process. The features of process 210 may be performed by the pathways scorer 148 and the aggregation assessor 149 of the module 142, in FIG. 1. The aggregation score is an example of a summary score of the analyze pathway set for a subject.

At a block 212, the summary score from process 210 is compared against enrichment scores of pre-determined molecular subtypes to determine if a match exists, where a match may be determined using a matching rule. For example, an aggregation score from the process 210 may be compared against enrichment scores in the form of predetermined HER2+ or HER2− pathway gene expression scores. If the aggregation score is sufficiently, statistically associated with the enrichment score, the process 212 identifies the corresponding candidate molecular subtype to a block 214, where a report containing the identified molecular subtype is generated for display to a user, for storage by a computing device, and/or for communicating remotely to a user via communication network. In some implementations, the process 212 may identify multiple candidates of molecular subtypes, and the process 214 may generate a report containing each of them, where in some examples, the molecular subtypes are ranked according to a similarity score. In various embodiments, the report may include a report element that indicates one or more therapies that are likely to work for a given molecular subtype base on stored associations between the two. In various embodiments, the reports may be ranked by the best match for the determined molecular subtype.

Optionally, in some examples the molecular subtype is provided to a block 216 that determines a recommended set of treatments/therapies, from a larger universe of available treatments/therapies, that corresponds to the replacement molecular subtype. For example, available treatments generally associated with molecular subtypes may be stored in the computing device 102 in a ranked manner. The block 214 therefore may generate a report that includes a report element that indicates one or more treatments/therapies that are likely to work for a given molecular subtype base on stored associations between the two, or known associations (for example, published research studies and/or clinical trials, or NCCN or FDA guidelines). In various embodiments, the reports may be ranked by the best match for the determined molecular subtype.

Figure 3A:
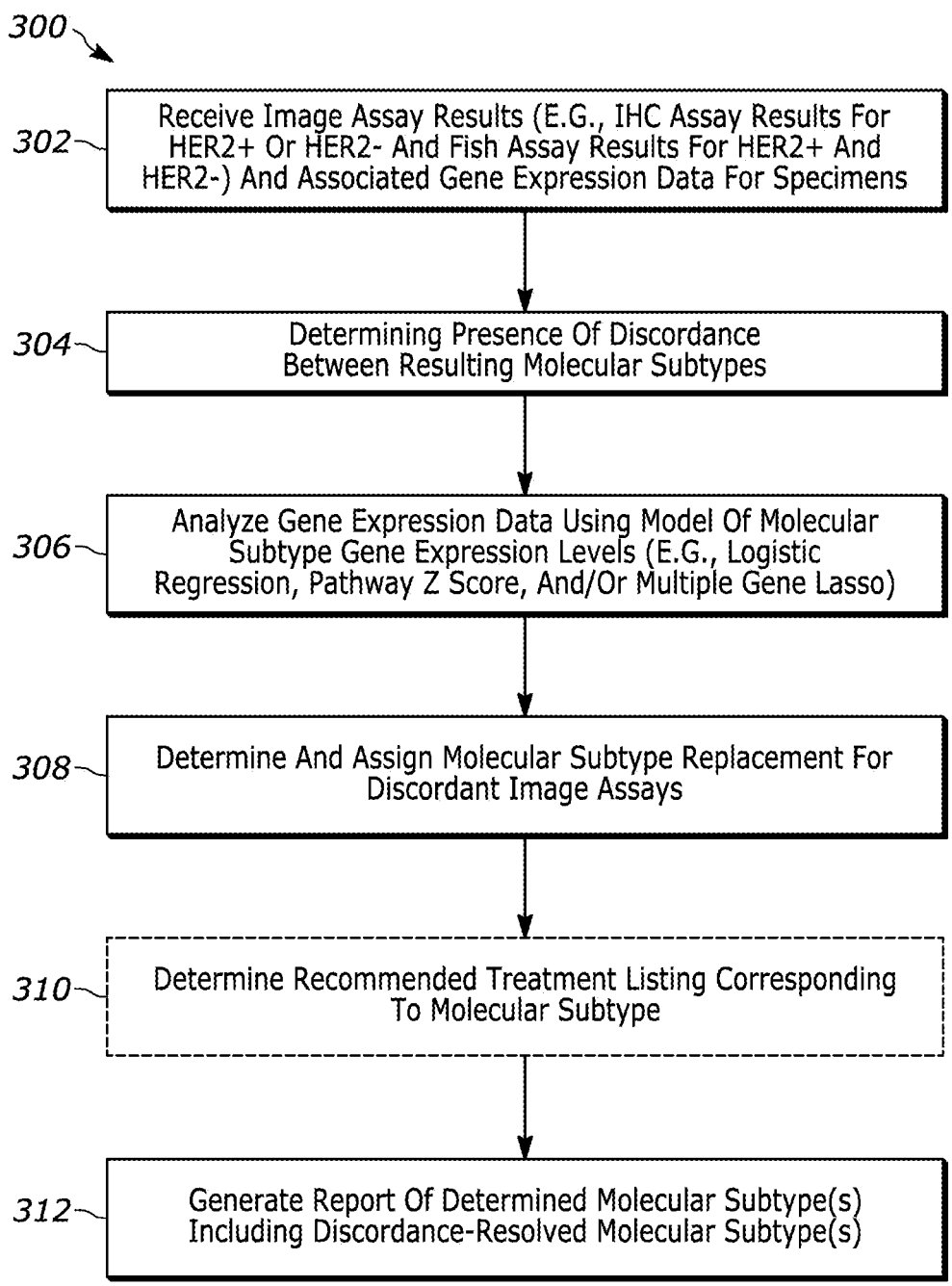
FIG. 3A is a block diagram of an example process for performing image assay replacement analysis and molecular subtype identification from RNA-seq data, as performed by the processing system of FIG. 1, in accordance with an example.

In contrast to the pipeline 140, the pipeline 130 in FIG. 1 is an image-replacement—analysis pipeline. An example implementation of the pipeline is shown in FIG. 3 and the process 300. At a block 302, the process 300 receives image assay results data, e.g., IHC image results and/or FISH image results with molecular subtype conclusions. For example, these image assay results may come from pathologist labeled IHC stain images and FISH stain images, labeled with HER2 status, HER2+ or HER2−. In some examples, as discussed herein, these image assay results may result from a trained image-based molecular subtype classification model, such as the model 136. At a block 304, the image assay results data are compared and discordance is examined for. For example, at the block 304, a comparison is made of resulting molecular subtypes of the different image assay results to determine if there is discordance between the results, where discordance includes a disagreement between molecular subtype, for example, one image set (e.g., IHC) resulting in identification of the presence of HER2+ while another image set (e.g., FISH) resulting in a negative presence of HER2+ or an equivocal determination of HER2.

At block 306, in response to a determination of discordance between resulting molecular subtypes, a gene expression data (e.g., RNA-seq data) corresponding to specimens associated with the image assay results, is analyzed to determine molecular subtype. In various embodiments, for example, associated RNA-seq data is analyzed by the block 306 configured with a linear regression model trained on gene expression data training data, such as RNA expression training data. For example, the linear regression model may be trained to examine for HER2+ and HER2− results in gene expression data. The block 306 may analyze the RNA-seq data with a logistic regression model of HER2 gene expression levels. For other molecular subtypes of IHC targets, the logistic regression model would be for gene expression levels for that molecular subtype or expression levels for the gene(s) associated with the IHC target(s).

In various other examples, the block 306 is configured to use a pathway analysis, for example implementing the pipeline 140, to examine RNA-seq data, determine which pathway best matches that data using a trained model, and identify the molecular subtype based on that pathway analysis. For example, in response to identifying a discordance of molecular subtype classification among the image assay results, the block 306 may provide the molecular subtype data and patient data to a gene expression-based pipeline for analysis, such as using process 200 in FIG. 2.

These various processes of block 306 and 308 may be performed by the subtype discordance resolver 138 in accordance with other features, such as the pipeline 140 and processes thereof.

In yet various other examples, the block 306 implements a multiple gene lasso model that looks at the expression levels of multiple genes in RNA-seq data, and using a trained classification model, applying a LASSO linear regression process to examiner whether the RNA-seq data is closer to one gene expression group (for example, gene expression levels associated with one molecular subtype) versus other gene expression groups (for example, gene expression levels associated with another molecular subtype). From the comparison a determination of molecular subtype is made, e.g., HER2+ or HER2−. For example, the process 306 may compare gene expression data using genes in prediction models for different molecular subtypes: estrogen receptors (ER) for ER+ breast cancer, progesterone receptors (PR)/PGR gene for PR-positive cancers, and HER2 for HER2+ breast cancers, with the corresponding gene lists as follows. For each gene, the ensembl_gene_id is provided, along with a coefficient value that is a weighting factor corresponding to the particular molecular subtype, and the hgnc_symbol. For example, a LASSO regression model may be applied to the following gene listings.

| | HER2 | | |
|---|---|---|---|
| | ensembl_gene_id | coef | hgnc_symbol |
| 22 | ENSG00000141736 | 1.6136 | ERBB2 |
| 23 | ENSG00000141741 | 1.4235 | MIEN1 |
| 61 | ENSG00000203870 | 0.6690 | SMIM9 |
| 15 | ENSG00000126091 | −0.6135 | ST3GAL3 |
| 46 | ENSG00000174151 | −0.4714 | CYB561D1 |
| 68 | ENSG00000243477 | −0.4498 | NAT6 |
| 17 | ENSG00000131748 | 0.4464 | STARD3 |
| 12 | ENSG00000124786 | 0.4145 | SLC35B3 |
| 2 | ENSG00000025796 | 0.4116 | SEC63 |
| 56 | ENSG00000185436 | −0.4102 | IFNLR1 |
| 21 | ENSG00000137522 | 0.3728 | RNF121 |
| 11 | ENSG00000116704 | 0.3054 | SLC35D1 |
| 37 | ENSG00000166341 | 0.2797 | DCHS1 |
| 35 | ENSG00000162849 | 0.2665 | KIF26B |
| 38 | ENSG00000166923 | 0.2564 | GREM1 |
| 14 | ENSG00000125686 | 0.2338 | MED1 |
| 63 | ENSG00000205281 | −0.2321 | GOLGA6L10 |
| 55 | ENSG00000184434 | −0.2051 | LRRC19 |
| 4 | ENSG00000055163 | −0.2017 | CYFIP2 |
| 32 | ENSG00000159239 | −0.1993 | C2orf81 |
| 60 | ENSG00000198842 | −0.1907 | DUSP27 |
| 48 | ENSG00000174938 | −0.1764 | SEZ6L2 |
| 1 | ENSG00000009709 | 0.1750 | PAX7 |
| 7 | ENSG00000090920 | −0.1614 | FCGBP |
| 64 | ENSG00000221869 | −0.1584 | CEBPD |
| 54 | ENSG00000181754 | −0.1425 | AMIGO1 |
| 51 | ENSG00000177483 | −0.1370 | RBM44 |
| 3 | ENSG00000040487 | −0.1268 | PQLC2 |
| 6 | ENSG00000075035 | −0.1168 | WSCD2 |
| 20 | ENSG00000136710 | −0.1121 | CCDC115 |
| 71 | ENSG00000269711 | 0.1103 | 8.061285857045354 |
| 41 | ENSG00000168928 | 0.1049 | CTRB2 |
| 26 | ENSG00000151320 | −0.1012 | AKAP6 |

| | ER | | | |
|---|---|---|---|---|
| | ensembl_transcript_id | coef | ensembl_gene_id | hgnc_symbol |
| 2 | ENST00000406599 | 1.1785 | ENSG00000091831 | ESR1 |
| 1 | ENST00000354189 | 0.0332 | ENSG00000118307 | CASC1 |
| 3 | ENST00000486448 | 0.0212 | ENSG00000173467 | AGR3 |

| | PR/PGR | | |
|---|---|---|---|
| | ensembl_gene_id | coef | hgnc_symbol |
| 2 | ENSG00000082175 | 1.2832 | PGR |
| 9 | ENSG00000134830 | 0.4349 | C5AR2 |
| 17 | ENSG00000173467 | 0.3320 | AGR3 |
| 8 | ENSG00000134352 | 0.1936 | IL6ST |
| 11 | ENSG00000159556 | −0.1595 | ISL2 |
| 18 | ENSG00000186910 | 0.1335 | SERPINA11 |
| 1 | ENSG00000004838 | 0.1134 | ZMYND10 |
| 7 | ENSG00000133019 | −0.1056 | CHRM3 |
| 16 | ENSG00000172771 | 0.1019 | EFCAB12 |
| 3 | ENSG00000091831 | 0.0976 | ESR1 |
| 6 | ENSG00000126010 | 0.0570 | GRPR |
| 15 | ENSG00000170743 | 0.0455 | SYT9 |

-continued

PR/PGR

| | ensembl_gene_id | coef | hgnc_symbol |
|---|---|---|---|
| 5 | ENSG00000124159 | −0.0382 | MATN4 |
| 10 | ENSG00000146857 | −0.0251 | STRA8 |
| 4 | ENSG00000124134 | −0.0133 | KCNS1 |
| 13 | ENSG00000164434 | −0.0118 | FABP7 |
| 14 | ENSG00000170054 | 0.0059 | SERPINA9 |
| 12 | ENSG00000163879 | 0.0025 | DNALI1 |

At a block 308, a determination of the gene-expression based molecular subtype is made, e.g., from the linear regression analysis, and assigned as a replacement molecular subtype for the discordant image assay results. For example, if an IHC image assay result indicates HER2+, FISH indicated HER2−, and the processes of blocks 306 and 308 determine HER2−, then the IHC image assay results may be replaced in the RWD/RWE data for the sample with the replacement determination of HER2−.

Advantageously, in various embodiments herein, discordance between image assay results may result in process 306 and 308 identifying an entirely different molecular subtype from either of the image assay results. For example, the processes 306 and 308 may supplement a HER2 determination with an ER determination (ER+/−) or a PR determination (PR+/−). Indeed, in various embodiments, the processes 306 and 308 may be implemented even if there is no discordance identified at the block 304. For example, the processes 306 and 308 may be performed before receiving image assay results. Indeed, in some examples, the processes 306 and 308 may be initially performed before any image analysis or where image analysis is not available. The processes 306 and 308 could be performed and only if a particular result is determined, such as HER2+, would the computer device send a request for an image-based analysis. Indeed, in these ways the process 300 may be used to predict other biomarkers in IHC results, by examining gene expression levels in associated RNA-seq data. That is, the process 300 may be used to identify ER, PR, or Ki67 (for example, to determine Luminal A vs. Luminal B), and then determine molecular subtypes such as HER2+/−, ER+/−, PR+/−, or triple negative. And further determine, if the molecular subtype if ER+ or PR+, whether that subtype is Luminal A/B. Example discussions of biomarkers that may be identified by these image assay replacement techniques are described in U.S. application Ser. No. 16/888,357, filed May 29, 2020, entitled "A pan-cancer model to predict the pd-I1 status of a cancer cell sample using RNA expression data and other patient data," incorporated by reference herein in its entirety for all purposes.

Optionally, in some examples the replacement molecular subtype is provided to a block 310 that determines a recommended set of treatments/therapies, from a larger universe of available treatments/therapies, that corresponds to the replacement molecular subtype. For example, available treatments generally associated with molecular subtypes may be stored in the computing device 102 in a ranked manner. A report is generated at block 312 indicating the determined molecular subtype including the resolved subtype from the analysis, as well as, in some examples, the image-based discordant subtypes. In various embodiments, the report may include a report element that indicates one or more treatments/therapies that are likely to work for a given molecular subtype base on stored associations between the two, or known associations (for example, published research studies and/or clinical trials, or NCCN or FDA guidelines). In various embodiments, the reports may be ranked by the best match for the determined molecular subtype.

Figure 3B:
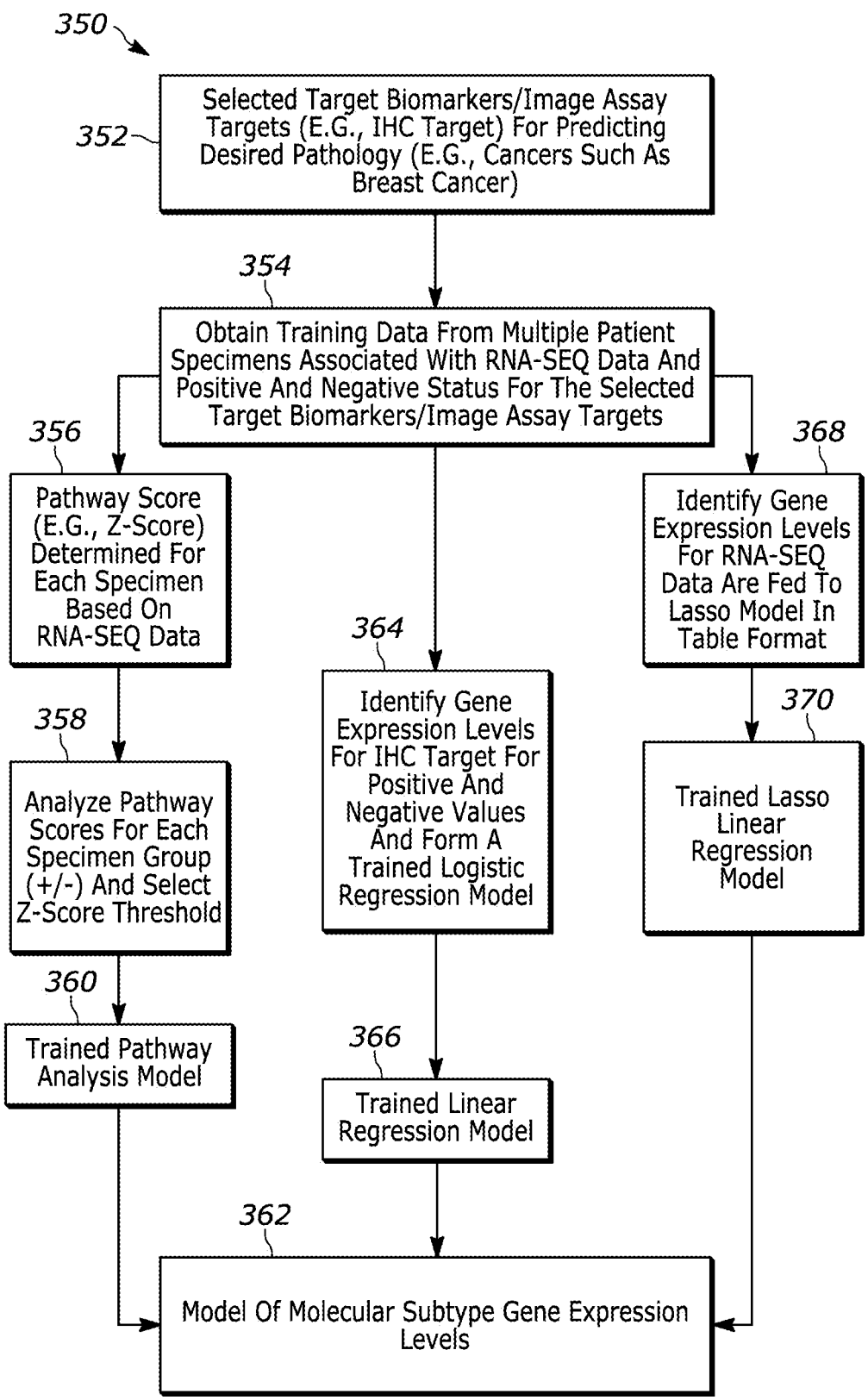
FIG. 3B is a block diagram of example classification model training processes as may be used to train classification processes of the example process of FIG. 3B, in accordance with an example.

FIG. 3B illustrates another example implementation a training process 350 that may be performed by the computing device 102, e.g., using the resolver 138 to train a molecular subtype model 136, for use in implementing the processes of block 306. At a block 352, target biomarker(s) and/or IHC target classifications are selected, such as, biomarkers/targets for predicting cancer types and/or cancer molecular subtypes. For breast cancer, for example, IHC results of the following biomarkers are known for use, HER2, ER, PR/PGR, and Ki67. At a block 354, training data with multiple patient specimens each associated with RNA-seq data and a positive or negative status for that biomarker/target is obtained. At an optional block 356, a pathway score (z-score) is calculated for each specimen based on the RNA-seq data (RNA-seq data could be whole transcriptome or targeted panel). At a block 358, the pathway scores for each specimen group (positive vs negative) is analyzed to select a z-score threshold that separates positive from negative values. The result is a trained pathway analysis model 360 that may be stored as the model of molecular subtype gene expression levels 362 of process 306. Or, in training a logistic regression model, at a block 364, gene expression levels for the IHC target after separating the specimens into positive vs negative values are used to train a logistic regression model. The resulting linear regression model 366 is stored as the model 362. Or, in training a multiple gene model, at a block 368, to train a LASSO model, the gene expression levels of the RNA-seq data are fed into a LASSO model as a table where each row is a specimen, one column is the IHC status, each other column is a gene with a gene expression level for that specimen. The resulting trained LASSO model 370 is stored as the model 362. As will be appreciated, which each of these training paths is shown separately, depending on the sufficiency of the training data, the model 362 may collectively include classification models trained by all of these training pathways.

Example implementations of a gene expression pathway analysis pipeline in accordance with the processes 200 and 300 are described below.

EXAMPLES

In an example implementation, a cohort selection was performed to identify patient data for analysis using the techniques herein, including the processes of FIG. 2. For cohort selection, two retrospective breast cancer cohorts were randomly selected from a clinicogenomic database after applying clinically relevant inclusion criteria. All data were de-identified in accordance with the Health Insurance Portability and Accountability Act (HIPAA). Dates used for analyses were relative to the breast cancer primary diagnosis (pdx) date, and year of pdx was randomly off-set. Pdx within the cohorts spanned from 1990-2018.

The first data group was a clinical abstraction (CA) cohort of 4,000 breast cancer patients randomly selected as a representative sample of RWD structured in the oncology database. To be included in the cohort, records were required to have data for a breast cancer pdx, pdx date, age, race, sex, stage, histological subtype, and estrogen receptor (ER), progesterone receptor (PR), and human epidermal growth factor receptor 2 (HER2) status. The recorded stage and histological subtype were required to fall within 30 days relative to the pdx date, while the receptor statuses may have been recorded within 30 or 50 days, depending on the testing modality.

A second cohort was also randomly selected, the molecular sequenced (MLC) cohort, which included 400 primary breast cancer patients with pdx dates and whose tumor biopsy underwent RNA-seq and targeted DNA sequencing (DNA-seq) with either a whole exome panel or one of two targeted sequencing panels between 2017-2019. While only patients with reported variants were included in the cohort, less than 1% of all breast cancer cases in the database have no DNA variants reported.

As a part of an image-based pipeline, abstracted molecular markers were determined from histopathology image data using the first cohort. Protein expression from immunohistochemistry (IHC) results for ER and PR, as well as IHC and fluorescence in-situ hybridization (FISH) results for HER2 were curated during clinical data abstraction. Receptor results included abstracted equivocal, positive, or negative statuses. Hormone receptor (HR) status was classified by combinations of ER and PR statuses. When available, Ki-67 indices were determined from the categorical interpretation of expression levels reported from routine clinical work in pathology reports and/or progress notes. Normalized Ki67 results included indeterminant, low, equivocal, moderate, or high statuses. A chi-squared test assessed the significance of Ki67 test result distribution differences. Fisher's exact tests were performed for post-hoc analyses, and P-values were adjusted for multiple hypothesis testing using Bonferroni correction.

Molecular subtype determination was performed as follows. The molecular subtype of each CA patient was classified as HR+/HER2−, HR+/HER2+, HR−/HER2+, or triple-negative breast cancer (TNBC) based on their receptor statuses at diagnosis. HR statuses were determined from the most recent IHC results or physician notes recorded within 30 days of the pdx date. HR+ status included ER+/PR+, ER+/PR−, and ER−/PR+. HER2 status was determined from the most recent FISH results recorded within 50 days of the pdx date. In the absence of HER2 FISH data, the most recent IHC result or physician note within 30 days of the pdx date was utilized. References to results at "initial diagnosis" imply these 30- and 50-day time frames. Molecular subtypes in the MLC cohort were determined from IHC or FISH results associated with the patient pathology report.

RWE or clinical data abstraction was performed as follows. Clinical data were extracted from the real-world oncology database of longitudinal structured and unstructured data from geographically diverse oncology practices, including integrated delivery networks, academic institutions, and community practices. Many of the records included in this study were obtained in partnership through ASCO CancerLinQ. Structured data from electronic health record systems were integrated with unstructured data collected from patient records via technology-enabled chart abstraction and corresponding molecular data, if applicable. Data were harmonized and normalized to standard terminologies from MedDRA, NCBI, Nat, NCIm, RxNorm, and SNOMED.

In an example, a menopausal status determination was made. Menopausal status was determined using relevant abstracted text fields when available. A patient was considered premenopausal if a single, undated menopause-negative (perimenopausal, premenopausal, or menstruating) status was recorded on or prior to the pdx date and no menopause-positive (menopausal or postmenopausal) status was indicated before diagnosis. Patients were also considered premenopausal at pdx if a menopausal event was recorded after a year from the pdx date.

Likewise, patients with an undated menopause-positive status, and patients with a menopausal or postmenopausal status recorded on or prior to the pdx date, were considered postmenopausal. A patient was also considered postmenopausal if no menopausal information was available on or prior to the pdx date, but a menopausal or postmenopausal status was indicated within one year after.

Menopausal status circumstances beyond the scope of these criteria were denoted as "Unknown."

With that data intake and analysis, an overall survival analysis was performed. Overall survival (OS) was calculated for all stage I-IV CA cohort patients with invasive breast cancer (n=3,952). Patients without known relative death dates were right censored at their most recent relative clinical interaction date. Survival curves were generated in R using the survival (v2.43-4) and survminer (v0.4.3) packages with P-values calculated by log-rank tests. Results depict the percentage of surviving patients per year, and are stratified based on stage and HER2, ER, and triple-negative status.

For genomic testing pipeline the second data cohort was used. In particular, MLC cohort reported variants were generated from targeted DNA-seq of formalin-fixed, paraffin-embedded (FFPE) slides of primary breast tumor biopsies and, when possible, matched saliva or blood samples. Whole-transcriptome RNA-seq was performed on samples from the same tissue block. Most samples were sequenced with one of two targeted DNA-seq assays, which detect oncologic targets in solid tumors and hematological malignancies as previously described. Two patient samples were sequenced with an updated and refined version of the xT panel targeting clinically relevant exons in 596 genes, and their reported variants were merged for analyses. Additionally, one sample in the MLC cohort was sequenced with a whole-exome panel targeting 19,396 genes over a 39 megabase (Mb) genomic region.

Because each assay targets different gene sets, MLC cohort variant analyses only included genes tested across all 400 samples. Variants were classified and reported according to previously established clinical guidelines. Reported variants were categorized as alterations, fusions, or copy number variation amplifications or deletions. Alterations include variants of unknown significance (VUS), biologically relevant or potentially actionable alterations, and both germline VUS and pathogenic variants.

Tumor mutational burden (TMB): TMB was calculated by dividing the number of non-synonymous mutations by the adjusted panel size of each assay (2.4 Mb, 5.86 Mb, and 36 Mb, respectively). All non-silent somatic coding mutations, including missense, indel, and stop-loss variants with coverage greater than 100× and an allelic fraction greater than 5% were counted as non-synonymous mutations.

RNA-based prediction of molecular subtypes: Transcriptome models were used to predict receptor statuses for the MLC cohort, including for patients lacking IHC or FISH data. In this example, single-gene logistic models were trained on an independent set of RNA-sequenced breast cancer samples according to the normalized gene expression of ESR1, PGR, or ERBB2 using the R glm package v2.0-16. In contrast to the MLC cohort, this independent training set contained both primary and metastatic breast cancer samples. Model performances were assessed separately for primary samples, metastatic samples, and a combined set using 10-fold cross-validation (Table 1). Performance was evaluated on a testing set comprised of RNA-sequenced samples from the MLC cohort with abstracted IHC or FISH results in the database (ER n=308, PR n=306, HER2 n=261), which were withheld from the training set. The abstracted results from clinical IHC or FISH testing were derived from the same tissue as the subsequent RNA-seq data. Positivity thresholds for IHC prediction models were selected using Youden's J statistic to optimize sensitivity and specificity. Normalized values greater than or equal to 2.36 for ESR1, 1.20 for PGR, and 3.59 for ERBB2 expression were considered positive for ER, PR, and HER2 receptor statuses, respectively.

Gene Expression Collection, Processing, and Normalization: Gene expression was generated through RNA-seq of FFPE tumor samples using an exome capture-based protocol. Transcript-level quantification to GRCh37 was performed using Kallisto 0.44. Transcript counts were then corrected for GC content and length using quantile normalization and adjusted for sequencing depth via a size factor method. Normalized counts in protein coding transcripts covered by the exome panel were then summed to obtain gene-level counts. Subsequent expression analyses were performed on $\log_{10}$-transformed counts.

RNA-seq Pathway Analyses: Gene sets were downloaded from the MSigDB website (http://software.broadinstitute-.orq/qsea/msiqdb/index.jsp), and pathway enrichment scores were calculated from normalized gene expression using the ssGSEA function in Gene Set Variation Analysis (GSVA) R Bioconductor package v1.0.6. ER- and HER2-related pathways were identified as those containing the terms "ESR1" or "Estrogen" and "ERBB2" or "HER2," respectively. Z-scores were calculated for each set of enrichment scores and the sign was reversed for any pathway containing "DN" (down) or "repressed." For select analyses, the mean of the z-score across pathways was calculated to produce a patient pathway metascore, as an example summary score, as an example summary score. With the exception of the HER2 and ER signaling pathway metascore analyses, receptor status was derived from both abstracted and predicted protein expression. Significance was determined by a Wilcoxon test for any comparison between two groups, and a Kruskal-Wallis test for comparisons between three or more groups, with P<0.05 considered significant. A separate gene set analysis was conducted to test the difference in enrichment among the four molecular subtypes relative to the 50 Hallmark pathways, a highly curated list from the MSigDB database. To determine how patients clustered by pathway scores, a second UMAP analysis was performed with enrichment scores for each Hallmark pathway as features.

The results of these examples were as follows.

First, we demonstrate results for the real-world evidence from a clinical abstraction (CA) breast cancer cohort, i.e., the first cohort.

Figure 4:
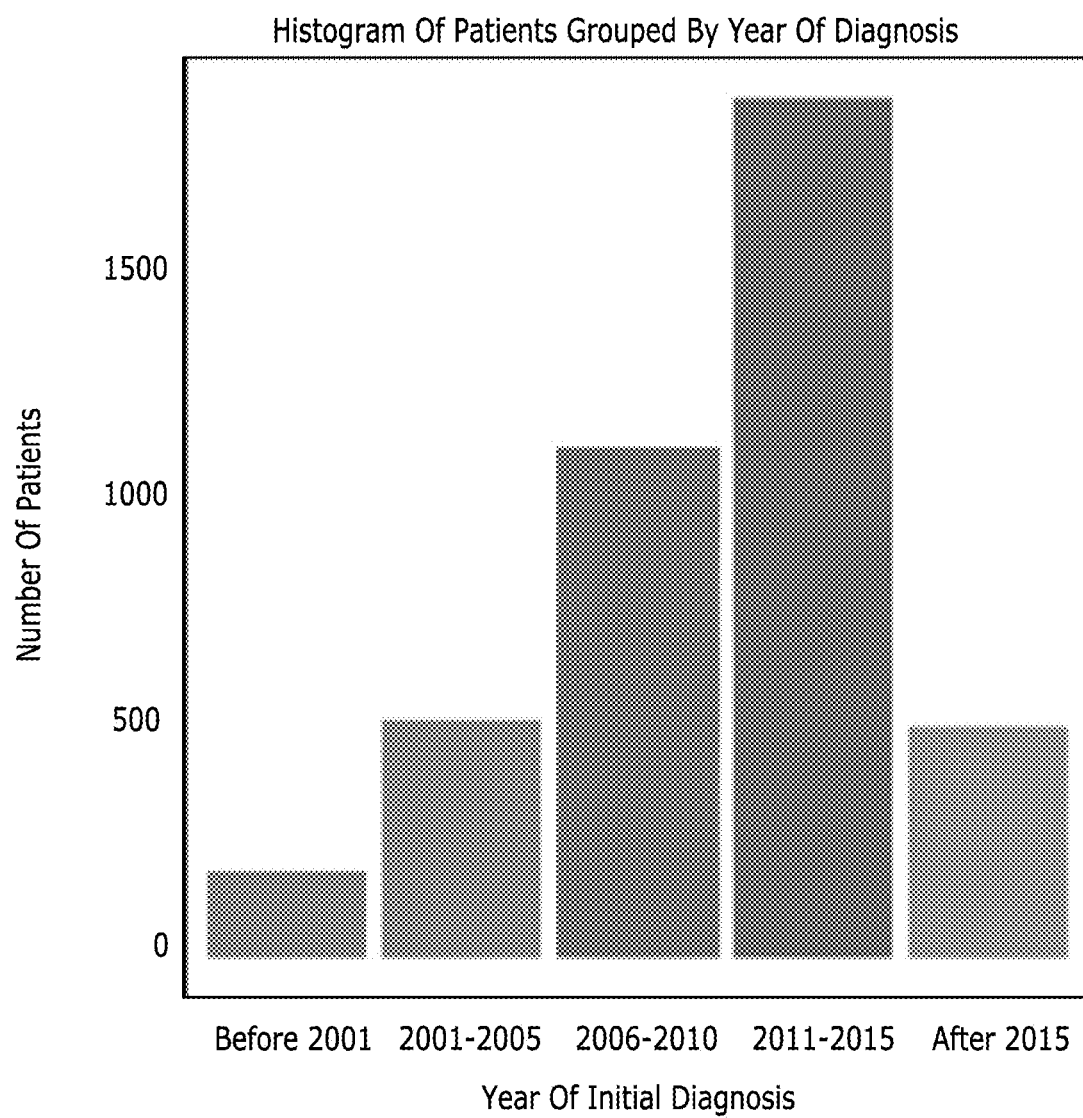
FIG. 4 is a plot of patients grouped by year of initial diagnosis, showing distribution of patients by year of initial diagnosis across the clinical abstraction cohort, in accordance with an example.

Patient demographics and clinical characteristics in the CA cohort: We first determined whether key demographic and clinical characteristics captured in RWD replicate clinical studies, and found the deidentified data were consistent with previous large-scale breast cancer cohort studies (Table 2). The cohort mostly comprised females (99.3%, n=3,970) with a median age at diagnosis of 61.0 years. Year of diagnosis among the cohort ranged from 1990 to 2018 (FIG. 4). The self-reported race was 83.3% White (n=3,332), 13.1% Black or African American (n=523), and 3.6% Asian or Pacific Islander (n=145). In 2,042 females with menopausal data, 87.4% (n=1,784) were postmenopausal. Abstracted stage at initial diagnosis primarily consisted of stage I (49.6%, n=1,986) and II (33.3%, n=1,333), followed by III (10.5%, n=420), IV (5.5%, n=219), and 0 (1.1%, 42). Most tumors had a histological classification of invasive ductal carcinoma (77.4%, n=3,095), and 9.5% (n=378) had an invasive ductal component or were NOS. Several rare cancer types were also represented.

Figure 5A:
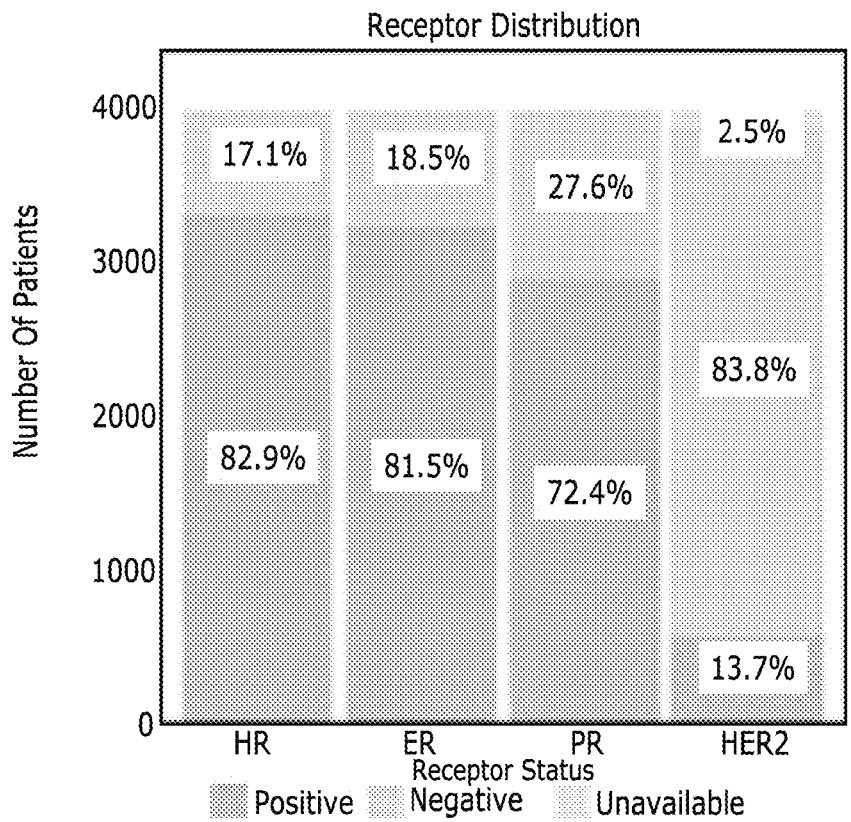
FIG. 5A-5D illustrate plots of breast cancer molecular biomarkers and subtypes in the clinical abstraction cohort, in accordance with an example.
Figure 5B:
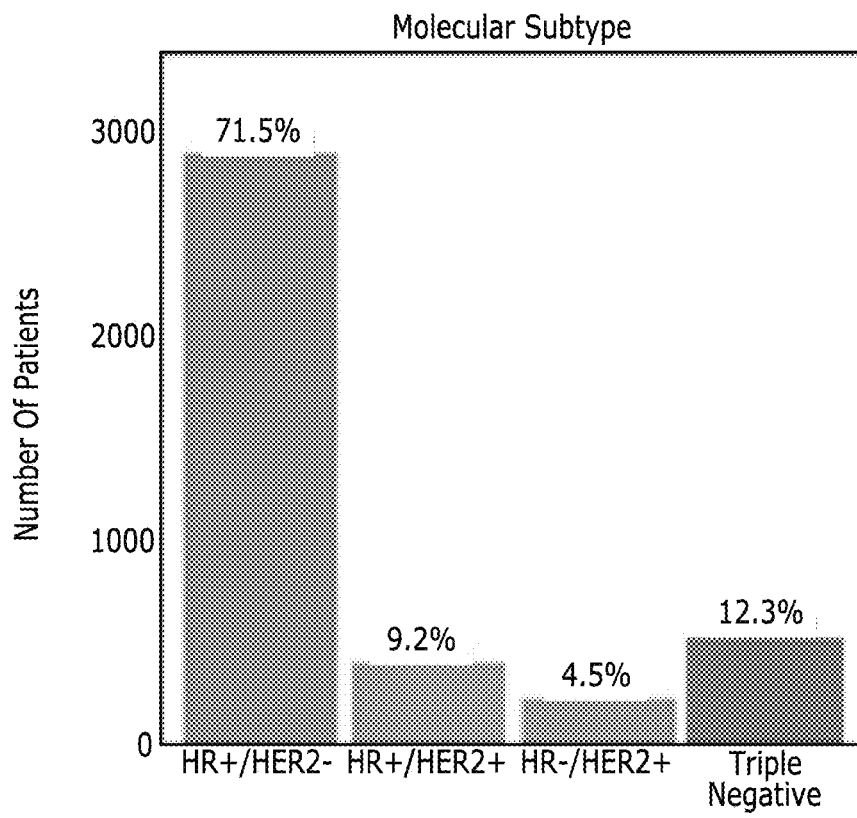
Figure 5C:
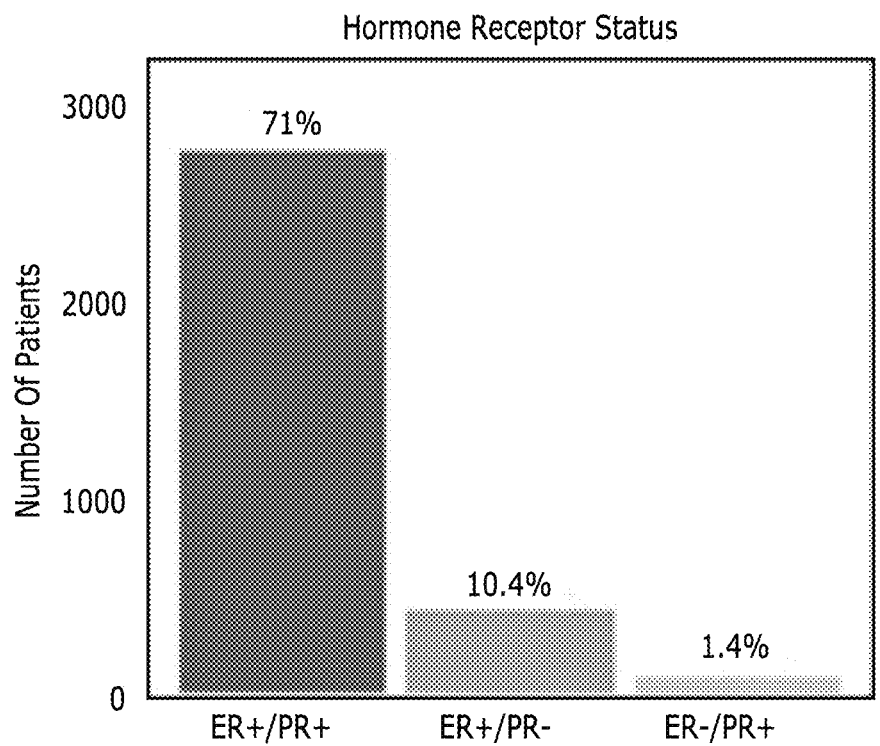
Figure 5D:
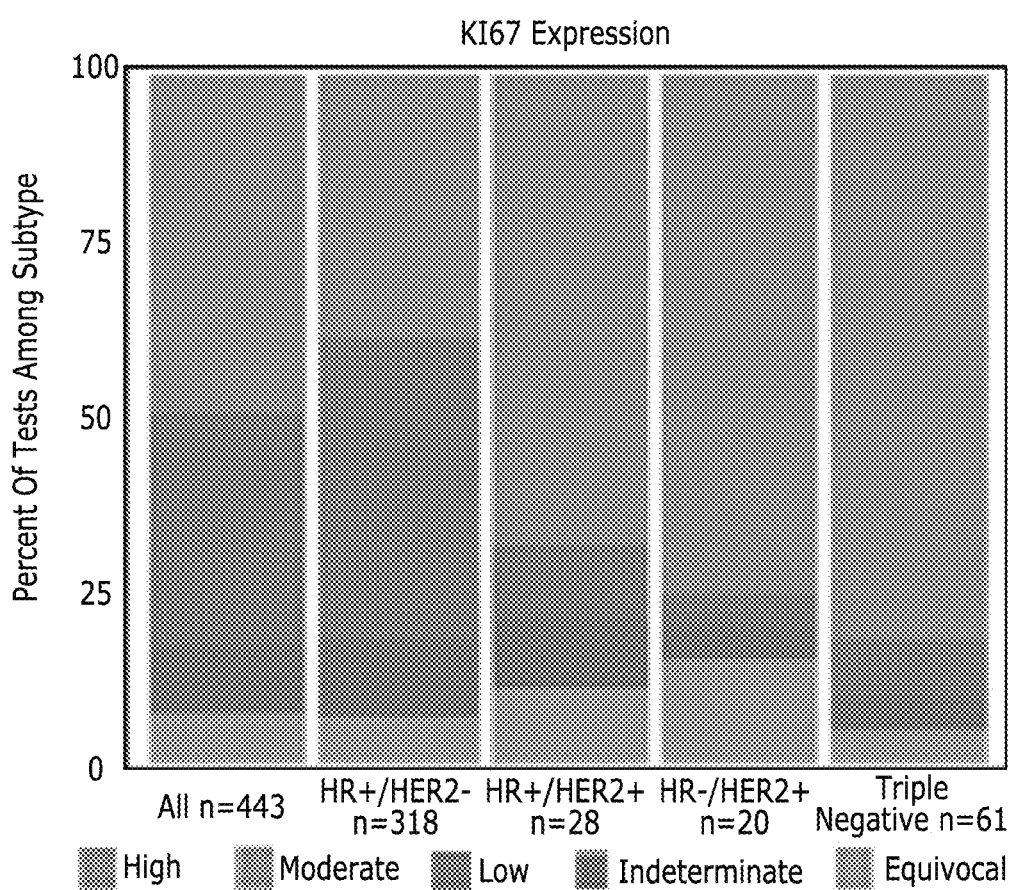

Molecular subtype determination in the CA cohort: We assessed the extent to which RWD captures molecular marker information from clinical testing results. The distributions of all abstracted receptor testing results at initial diagnosis are shown in FIG. 5A. Consistent with previous U.S. breast cancer statistics, the most prevalent molecular subtype was HR+/HER2- (71.5%, n=2,859), followed by TNBC (12.3%, n=491) (FIG. 5B). Among HR+ patients with non-equivocal statuses, most were ER+/PR+ (71.0%, 2,839 of 3,996) followed by ER+/PR- (10.4%, n=417) and ER-/PR+(1.4%, n=57) (FIG. 5C). Lastly, abstracted Ki67 IHC test results were consistent with the Ki67 expression levels typically indicative of specific breast cancer subtypes (FIG. 5D). The distribution of Ki67 results differed significantly among molecular subtypes (chi-squared, P=1 0.7 $5\times10^{-9}$), particularly between HR+/HER2- versus HR+/HER2+ patients (P=0.015) and TNBC versus HR+/HER2- patients (P=$6.38\times10^{-9}$). The largest proportions of high Ki67 IHC test results were in TNBC (82.0%, n=50 of 61) and HR-/HER2+ patients (75.0%, n=15 of 20), while most low Ki67 results were in HR+/HER2- patients (44.0%, n=140 of 318).

Figure 6A:
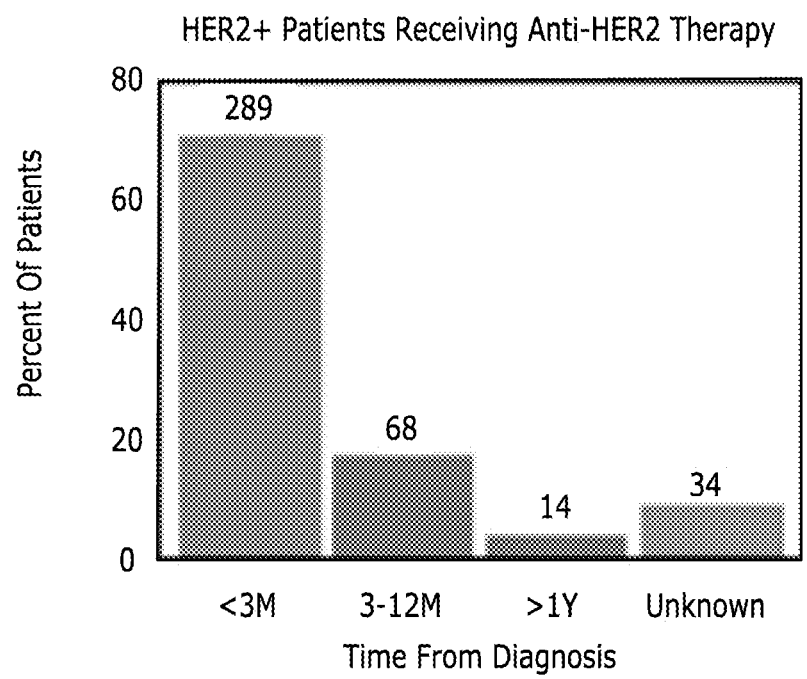
FIGS. 6A and 6B are plots showing anti-HER2 treatment by HER2 status in the clinical abstraction cohort, in accordance with an example. Anti-HER2 treatment initiation patterns among HER2+(FIG. 6A) and HER2− (FIG. 6B) patients who received anti-HER2 therapy at some point in their clinical care. M, month; Y, year.
Figure 6B:
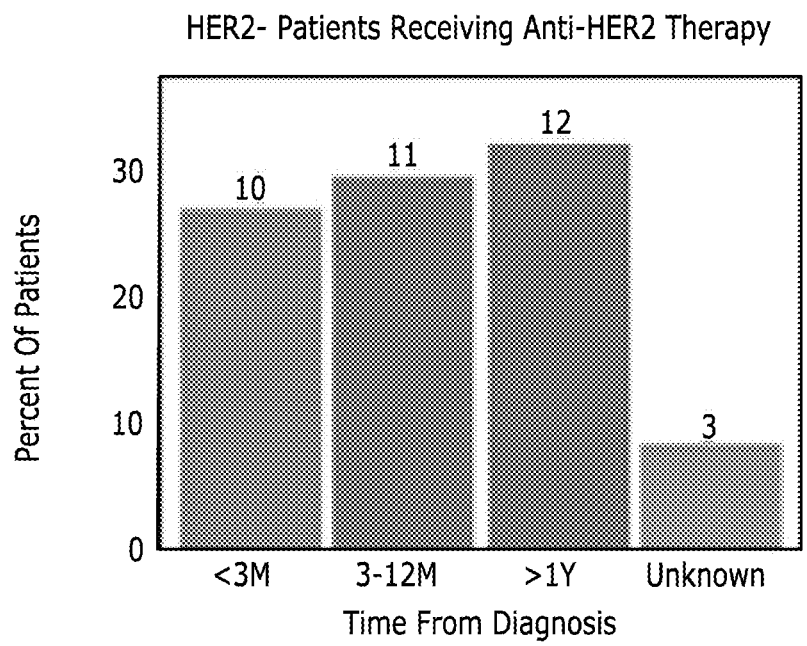

Anti-HER2 therapy analysis in the CA cohort: We next examined anti-HER2 therapy treatment patterns from longitudinal RWD. Curated anti-HER2 therapies included trastuzumab, ado-trastuzumab emtansine, neratinib, lapatinib and pertuzumab. Among CA cohort patients, 13.7% (n=546) were HER2+ at initial diagnosis, of whom 74.2% (n=405) received anti-HER2 therapy at some point in their clinical care. Approximately 70.0% of patients who received anti-HER2 therapy did so within 3 months of a positive test result and the majority (73.5%) had early-stage cancer (FIG. 6A). These results are consistent with previous breast cancer cohort studies. Moreover, a small portion of HER2- patients exhibited evidence of receiving an anti-HER2 therapy (1.1%, 36 of 3,352 HER2- patients). Among those patients, 27.8% received anti-HER2 therapy less than three months after the initial diagnosis (n=10), 30.6% between 3-12 months from initial diagnosis (n=11), and 33.3% after more than one year from the initial diagnosis (n=12), while 8.3% did not have a recorded anti-HER2 therapy start date (n=3) (FIG. 6B). Additionally, 33.3% (n=12) had evidence of a discordant result at initial diagnosis, 44.4% (n=16) had only HER2- results, and 22.2% (n=8) had a HER2-equivocal or positive result recorded beyond initial diagnosis. A small portion of patients (n=37) were not assigned a HER2 treatment time frame due to date quality issues.

HER2 test result analyses in the CA cohort: To evaluate inter- and intra-test concordance, we compared HER2 IHC and FISH results among patients with both tests conducted near initial diagnosis (17.7%, n=709). Among patients with HER2+ IHC results and subsequent FISH testing, 62.2% (n=51 of 82) were inter-test concordant (Table 3), however, 31.7% with HER2+ IHC were HER2- by FISH (n=26 of 82). This discordance is larger than a previously reported meta-analysis of IHC and FISH HER2 testing worldwide.[54] Four of those 26 patients had received an anti-HER2 therapy in their clinical timeline. Among patients with HER2-IHC results, 3.9% (n=7 of 182) were HER2+ by FISH, similar to historical reports.[54] The majority of these patients (n=6 of 7) received anti-HER2 therapy. HER2-equivocal IHC results (HER2 IHC 2+) were observed in 62.8% (n=445 of 709) of the cohort. Among these patients with equivocal results, 7.8% (n=35 of 445) were later confirmed equivocal by FISH testing. However, 80.7% (n=359 of 445) had subsequent HER2− and 11.5% (n=51 of 445) HER2+ FISH results.

Additionally, intra-test discordance was analyzed in patients with multiple HER2 results at initial diagnosis. Among patients with multiple HER2 IHC results at diagnosis (7.1%, n=253 of 3,561 with HER2 IHC), 18.6% (n=47) exhibited intra-test discordance. Of patients with multiple HER2 FISH results (4.5%, n=52 of 1,157), 21.2% (n=11) exhibited intra-test discordance.

Figure 7A:
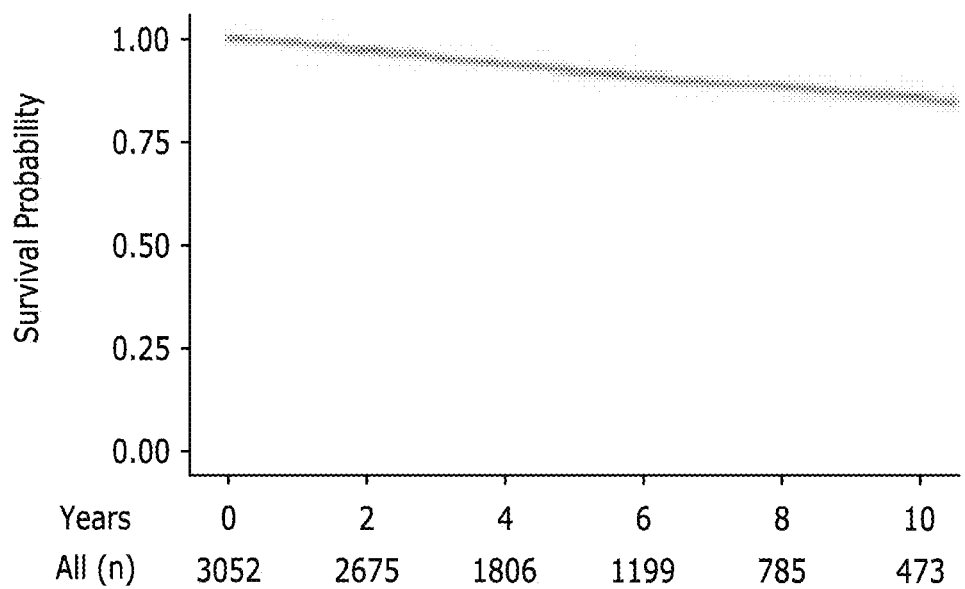
FIGS. 7A-7H are plots of overall survival from primary diagnosis dates in the clinical abstraction cohort, in accordance with an example. Ten-year survival probability in stage I-IV patients stratified by FIG. 7A stage and FIG. 7B subtype. Five-year survival probabilities stratified by HER2 status in FIG. 7C all patients and FIG. 7D stage IV patients, ER status in FIG. 7E all patients and FIG. 7F stage IV patients, and TNBC status in FIG. 7G all patients and FIG. 7H stage IV patients.
Figure 7B:
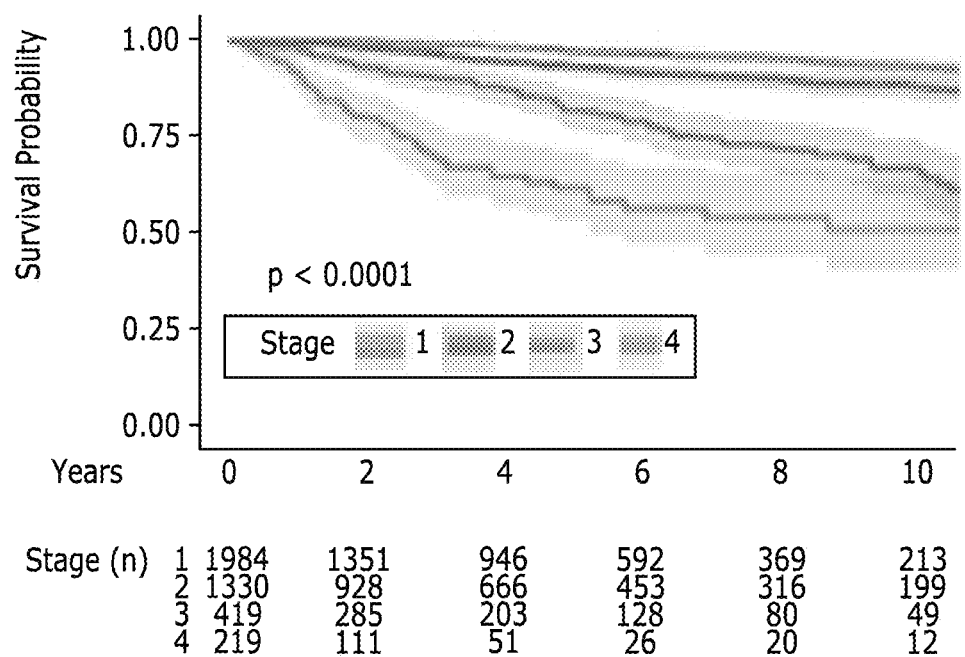
Figure 7C:
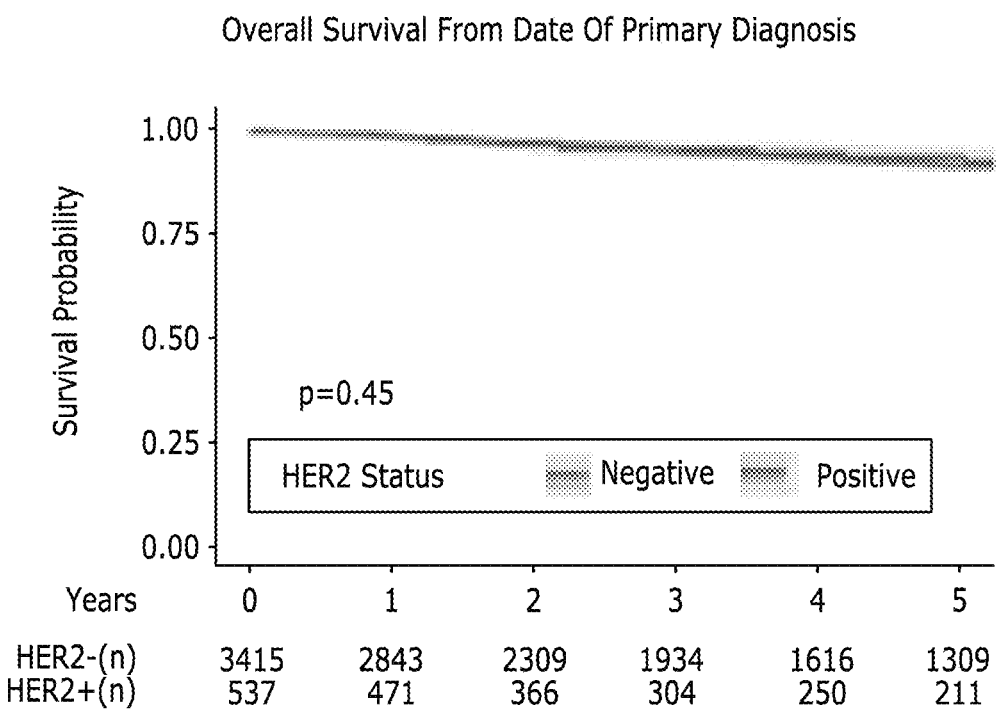
Figure 7D:
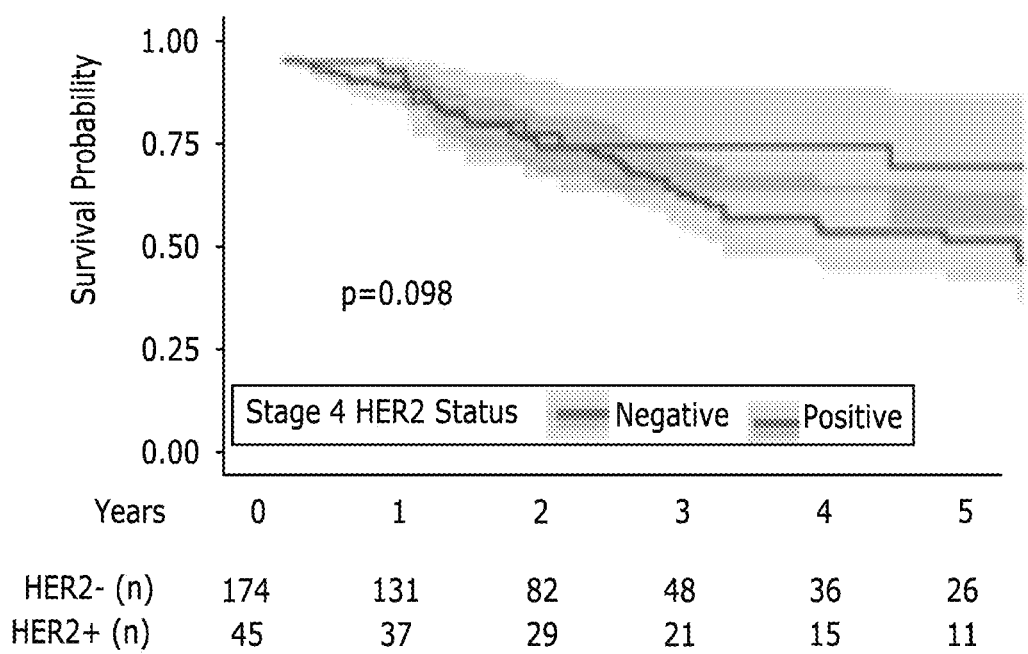
Figure 7E:
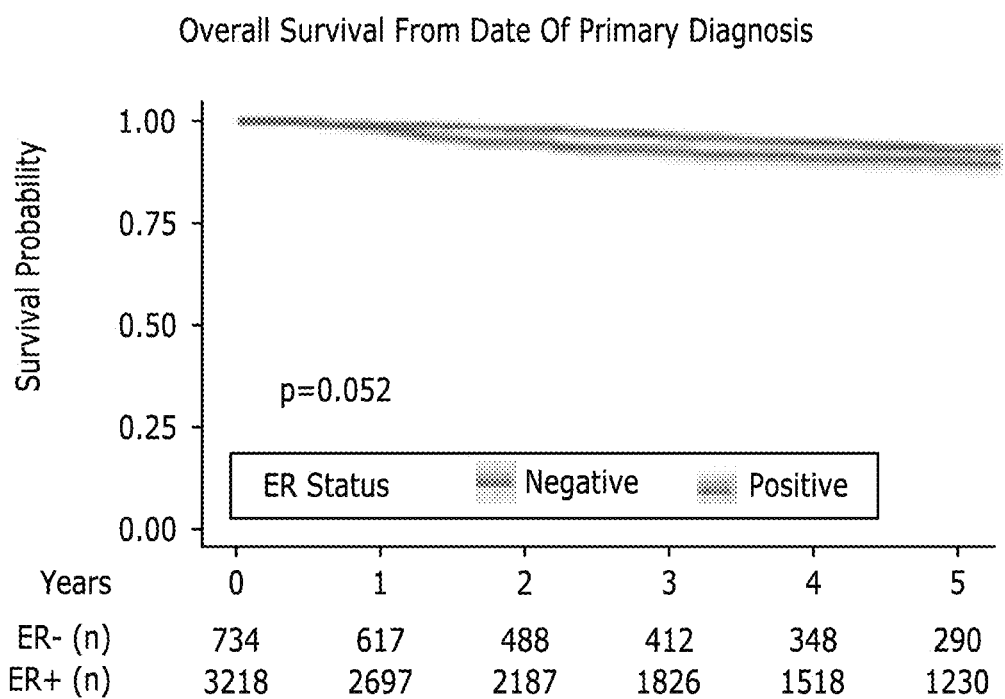
Figure 7F:
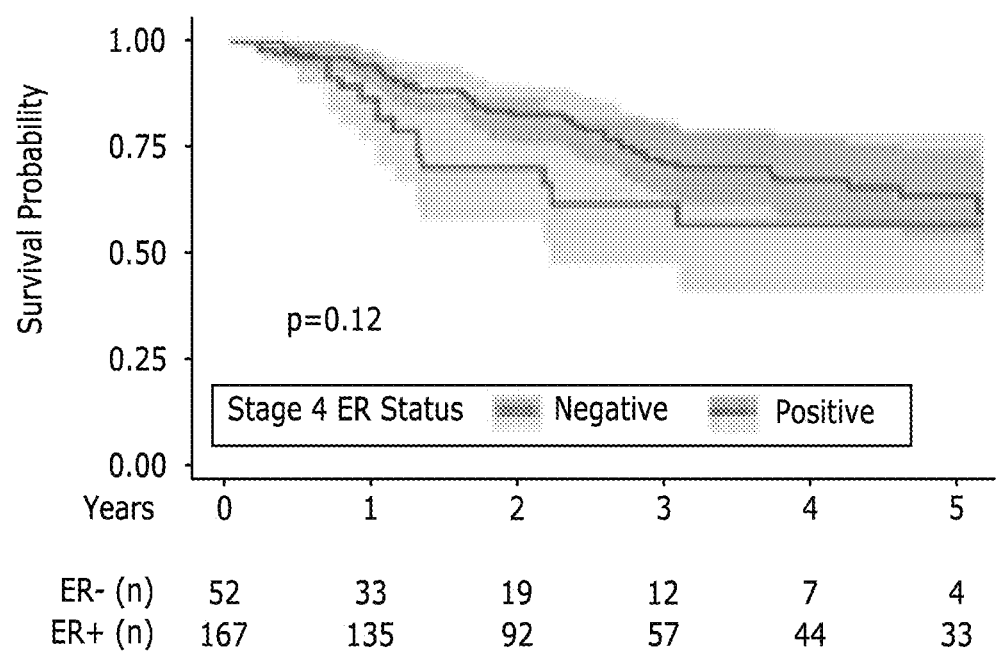
Figure 7G:
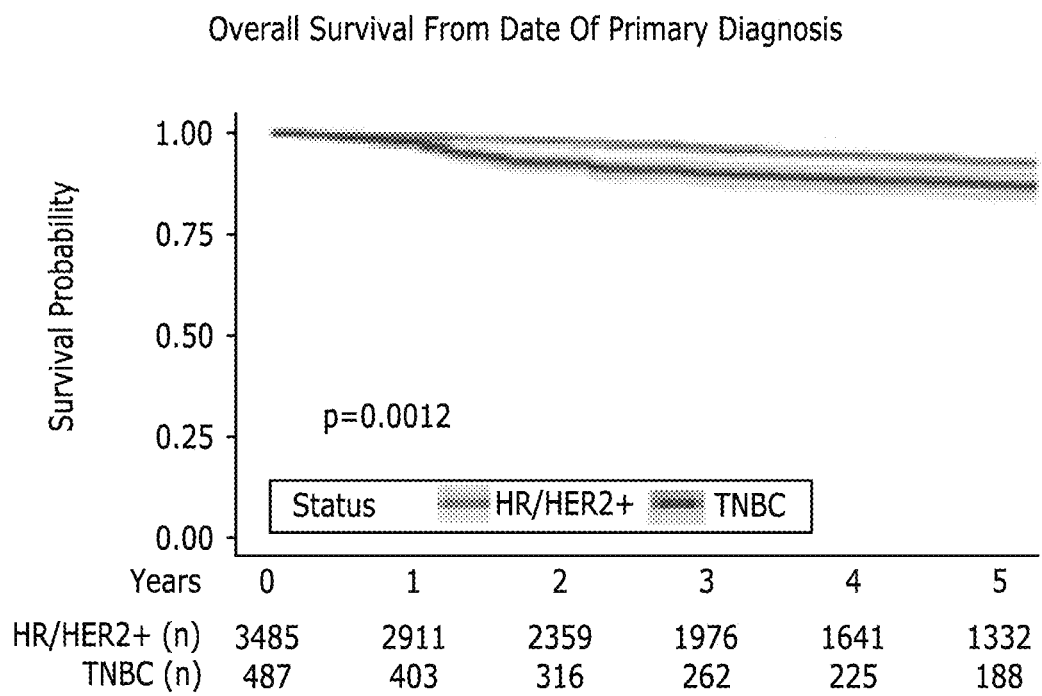
Figure 7H:
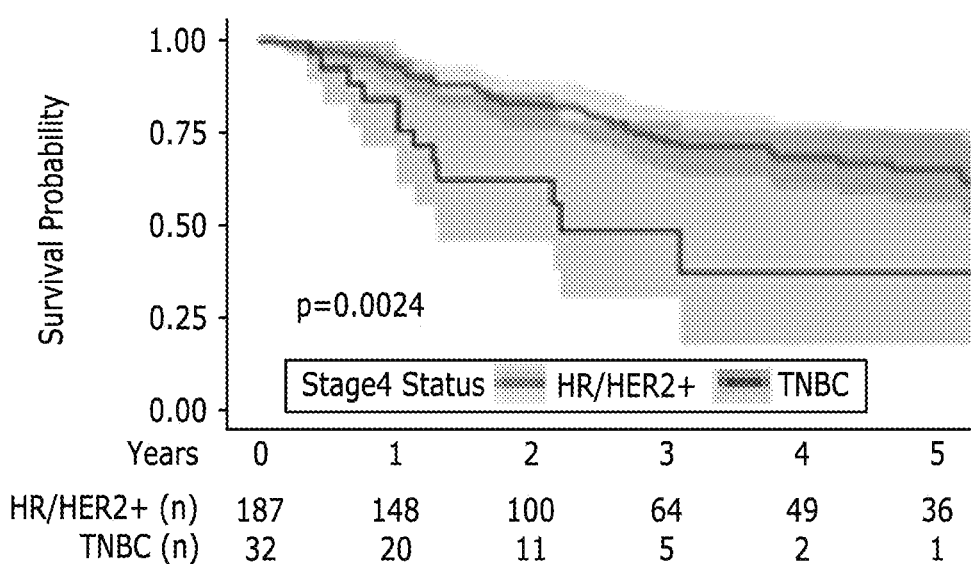

Overall survival in the CA cohort: OS analyses from longitudinal RWD revealed overall 5-year and 10-year survival rates (92.2% and 85.7%, respectively) relatively consistent with average U.S. percentages. Survival rates were expectedly high, varying as anticipated by stage (P<0.0001) (FIG. 7A) and receptor status (P=0.016) (FIG. 7B). The 5-year survival rate was 93.5% in stage I-IV HER2+ patients and 92.0% in HER2− patients (P=0.45), with rates of 74.3% and 57.1%, respectively, among stage IV patients (P=0.098) (FIG. 7C, FIG. 7D). The 5-year survival rate was 92.7% among stage I-IV ER+ patients and 89.8% in ER− patients (P=0.052), with rates of 63.7% and 55.5%, respectively, among stage IV patients (P=0.12) (FIG. 7E, FIG. 7F). TNBC patients had significantly worse OS compared to other subtypes, with a 36.3% 5-year survival rate in stage IV TNBC patients compared with 65.1% among stage IV non-TNBC patients (P=0.0024) (FIG. 7G, FIG. 7H).

Second, we demonstrate results for the genomic testing insights from the molecular sequenced cohort, i.e., the second cohort.

Patient demographics and clinical characteristics in the MLC cohort: Abstracted clinical characteristics and patient demographics from the 400 MLC cohort patients were assessed (Table 2), and found to be relatively consistent with the CA cohort and other large-scale breast cancer cohort studies. The cohort had a slightly younger median age at diagnosis of 55.8 years (45.2-66.4), and higher percentage of Black or African American (14.6%, n=35) and Asian or Pacific Islander patients (5.4%, n=13) than the CA cohort. Patients with known stage information were mostly stage II at diagnosis (38.4%, n=83), followed by stages IV (26.4%, n=57), III (21.3%, n=46), and I (13.9%, n=30), indicating an overall higher risk population compared with the CA cohort. A total of 75.0% (n=267) of tumors were invasive ductal carcinoma, with several rare cancer types also represented in the cohort.

Figure 8A:
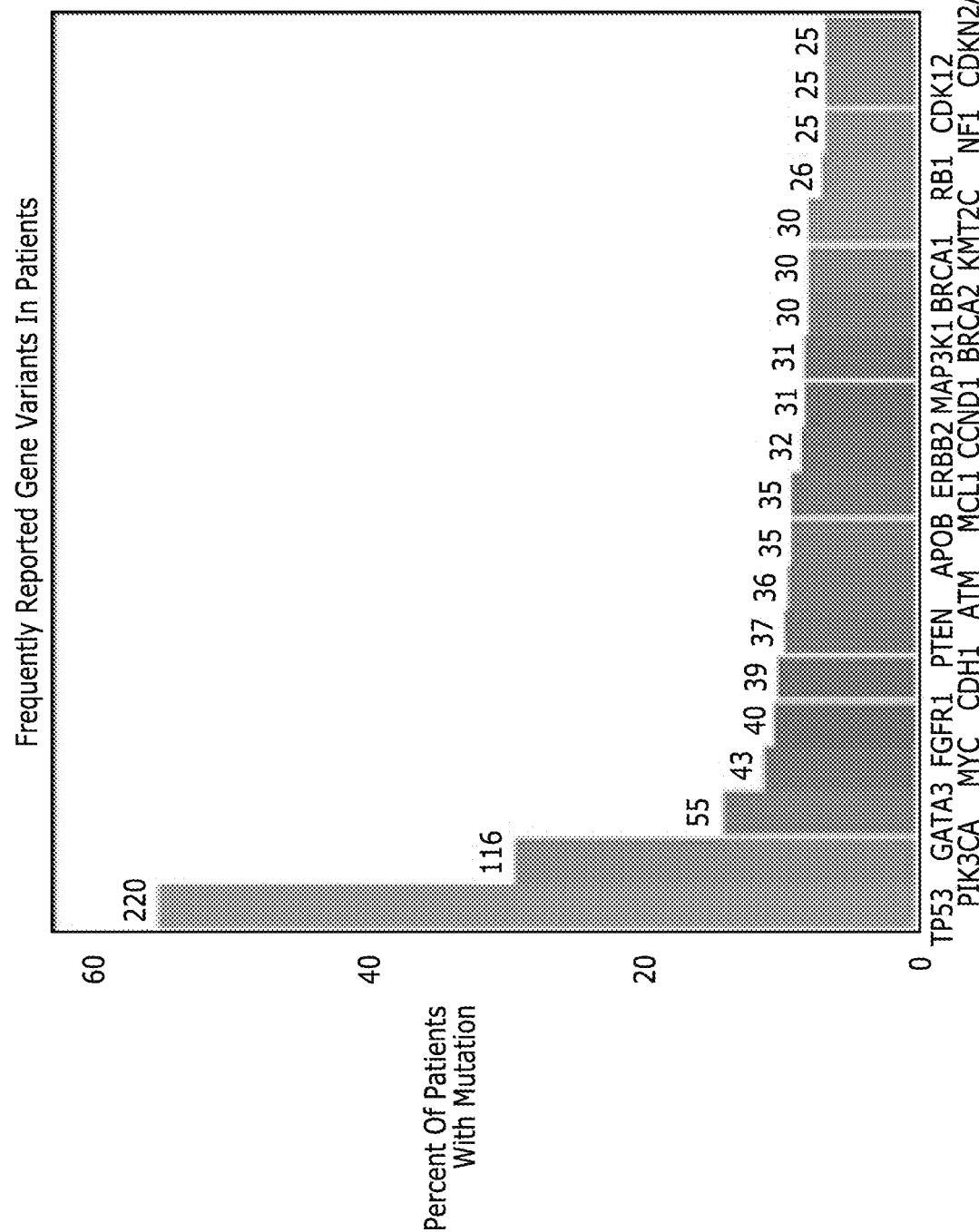
FIGS. 8A-8D illustrate molecular characteristics of the molecular sequenced cohort, in accordance with an example.
Figure 8B:
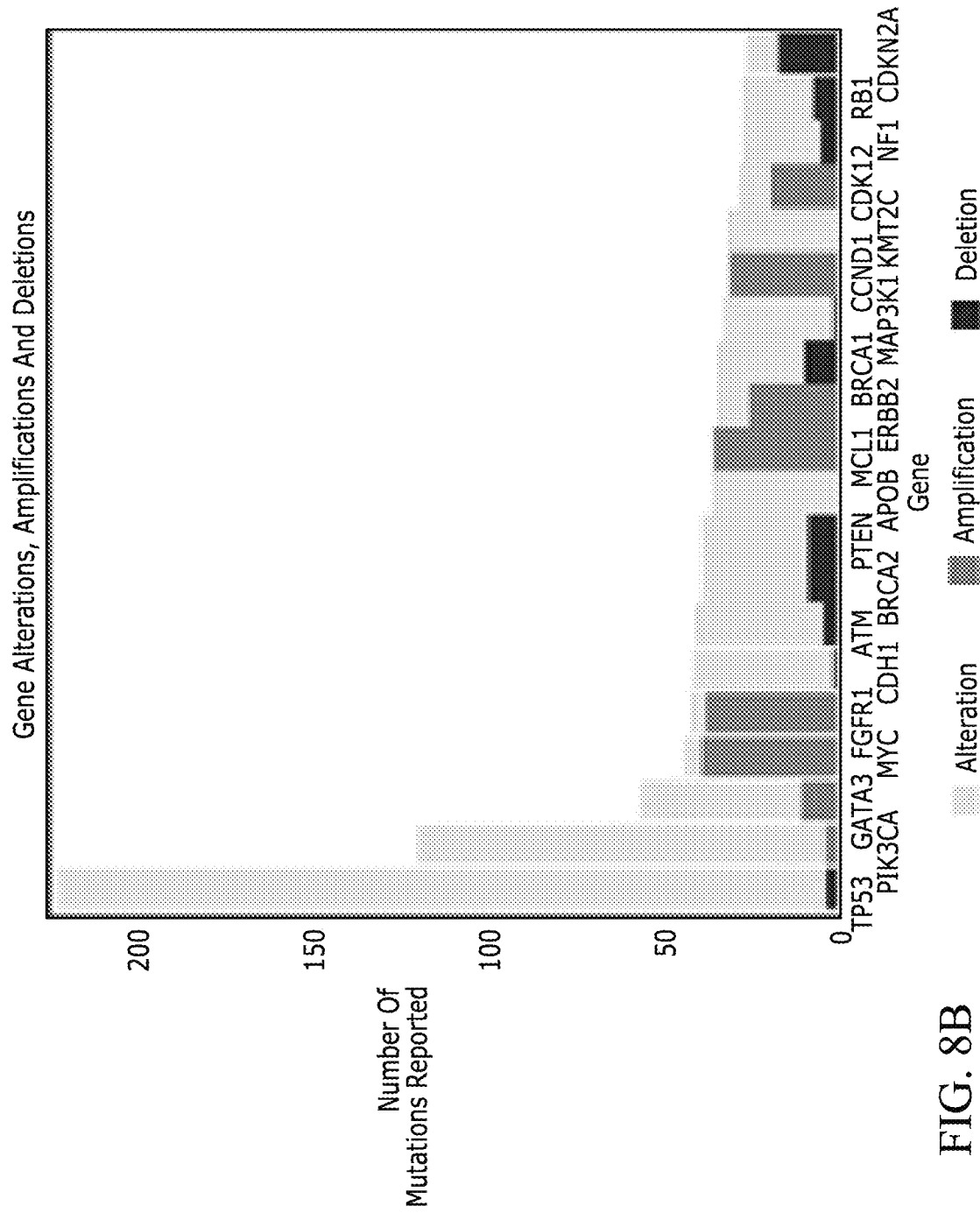
Figure 8C:
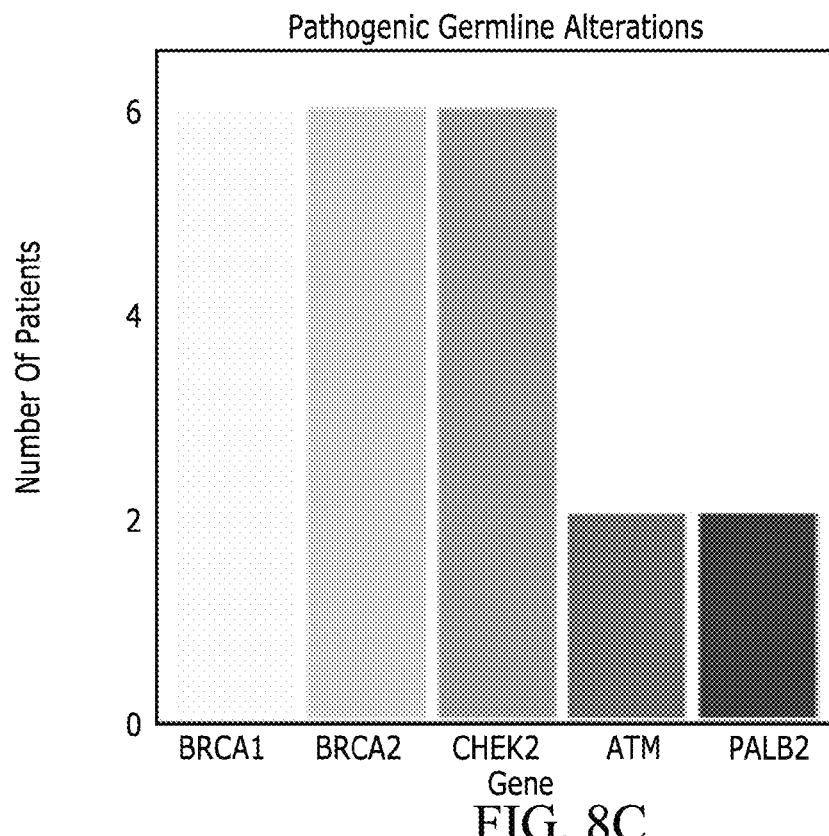
Figure 8D:
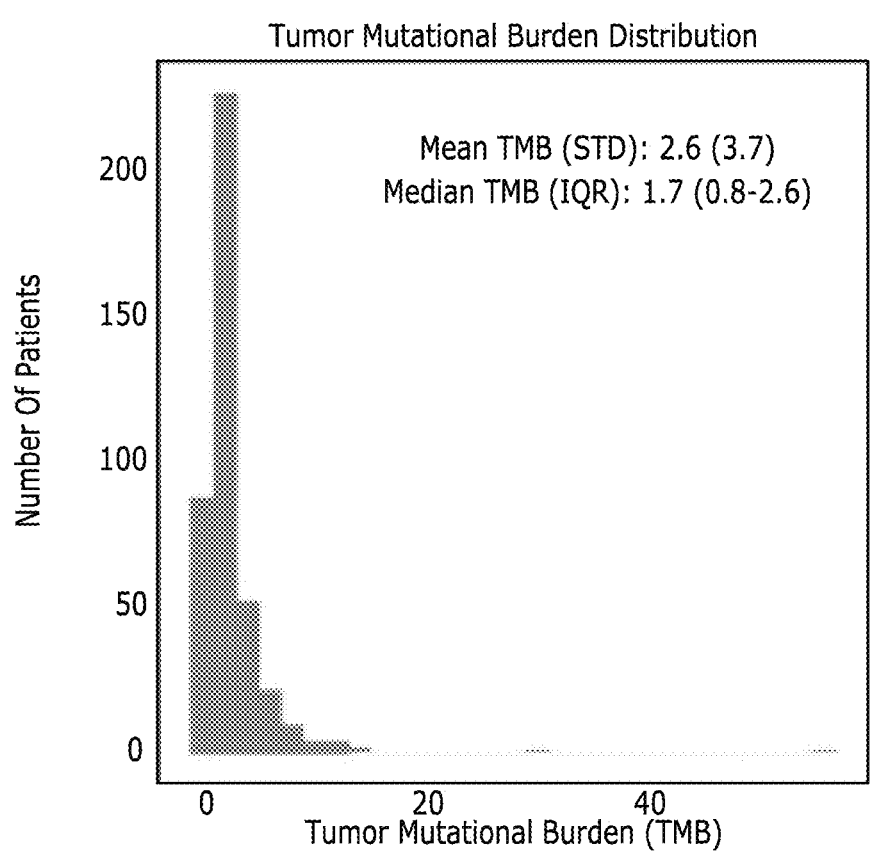

DNA sequencing analysis of the MLC cohort: The top three genes with reported alterations were TP53, PIK3CA, and GATA3, which were found in 55.0% (n=220), 29.0% (n=116), and 13.8% (n=55) of the MLC cohort, respectively (FIG. 8A). These findings are consistent with a previous analysis of The Cancer Genome Atlas breast cancer data. FIG. 8B shows the distribution of variant types in the 20 most frequently reported genes. Assessment of patients with tumor/normal-matched DNA-seq (n=356) identified 18 patients (5.1%) with pathogenic germline variants in 12 NCCN-designated familial high-risk genes (FIG. 8C). This sub-population may be underrepresented as exon-level duplications or deletions were not included. Among the 18 patients harboring a pathogenic germline variant in any of those 12 genes, most contained variants in BRCA1 (n=6), BRCA2 (n=6), CHEK2 (n=6), ATM (n=2), and/or PALB2 (n=2). Because TMB and MSI status are integrated biomarker measurements in this embodiment, we observed a wide range of TMB across the cohort with a median of 1.7 mutations/Mb (FIG. 8D). Consistent with previous studies, the majority of patients (84.7%, n=339) were MSI stable, while only 0.3% (n=1) were MSI high and 0.5% (n=2) were MSI low.

Figure 9A:
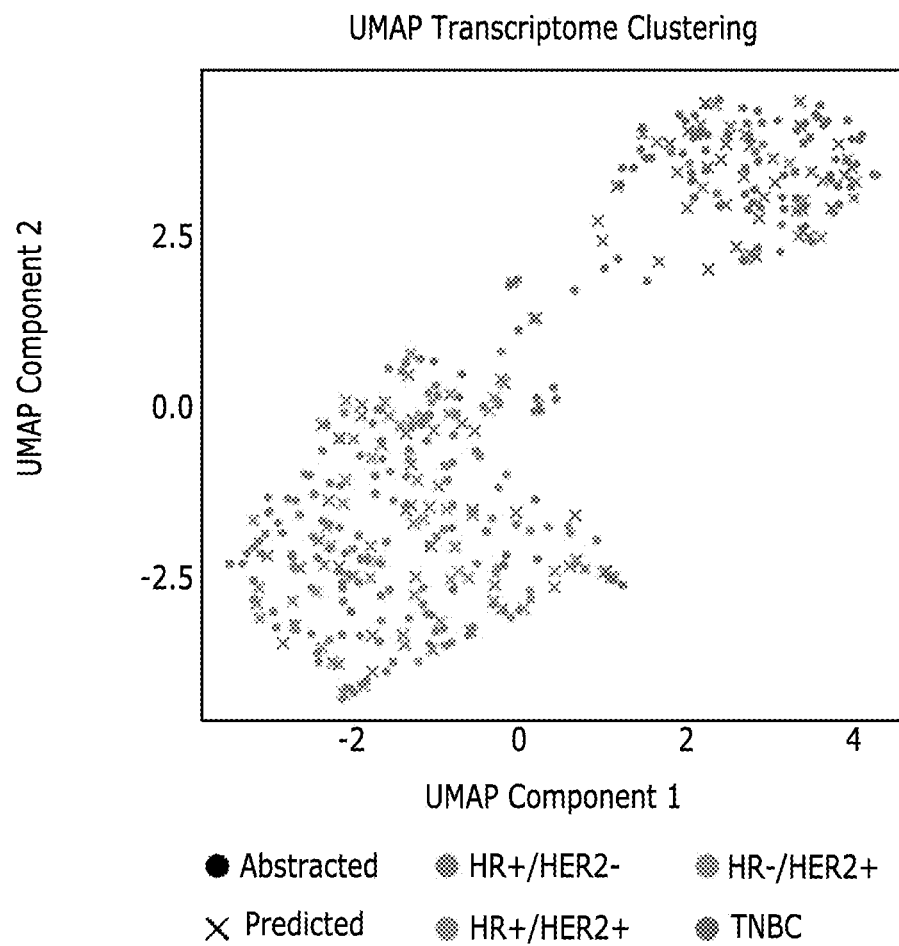
FIGS. 9A and 9B are plots related to RNA-based receptor status prediction analysis of the molecular sequenced cohort, in accordance with an example.
Figure 9B:
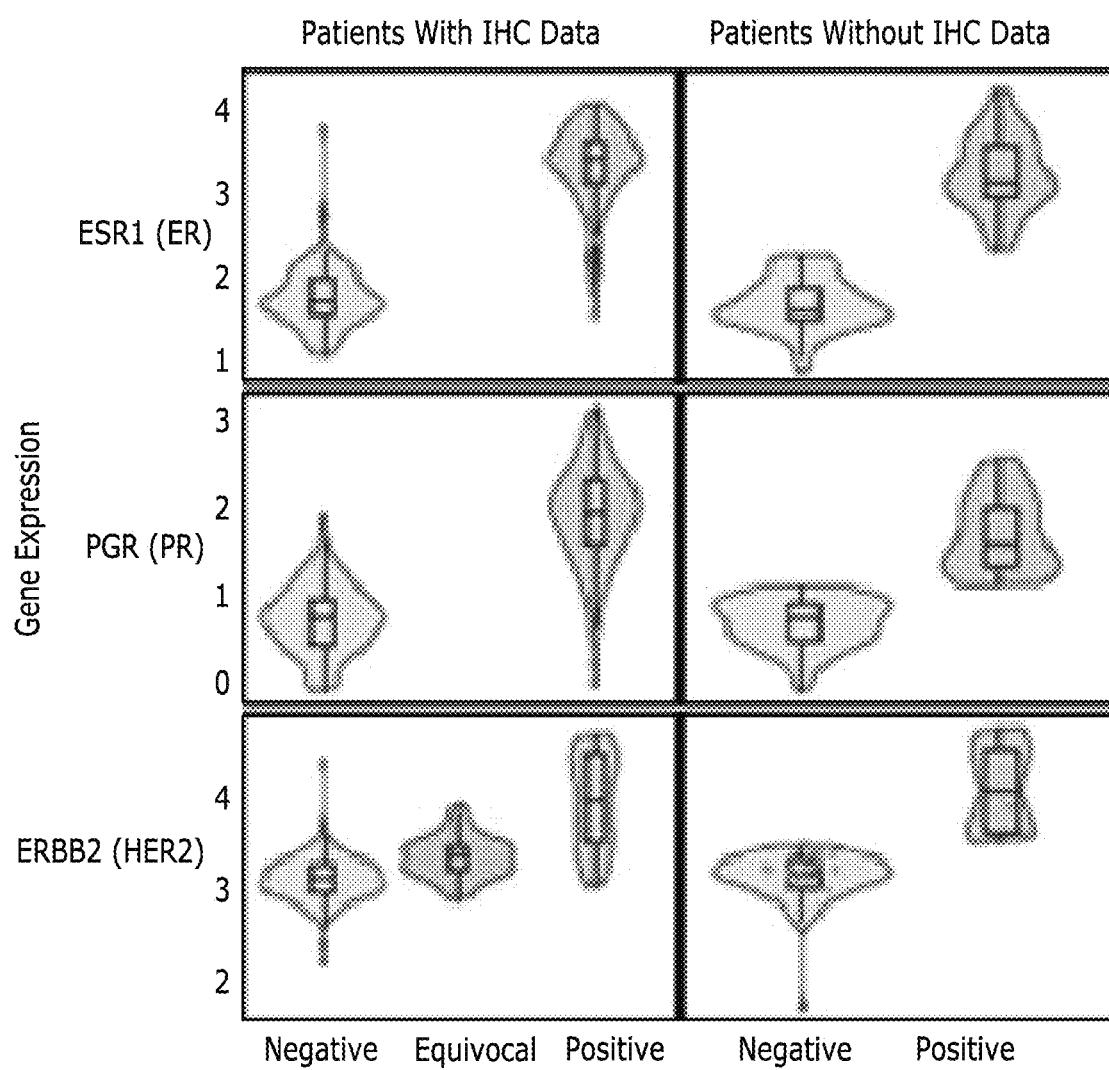

RNA-based prediction of receptor status for molecular subtypes: We developed a whole-transcriptome model based on 19,147 genes to predict IHC receptor status and resolve molecular subtypes in the MLC cohort. Predicted RNA-based subtypes largely aligned with abstracted IHC-based subtypes (FIG. 9A). Similar to the literature, transcriptome signatures differed between molecular subtypes with TNBC clustering separately. Seventeen samples clustered with TNBC but were predicted or abstracted as another subtype, suggesting samples that cluster outside of their groups may benefit from further testing or analysis. ESR1, PGR, and ERBB2 gene expression correlated with their respective abstracted and predicted receptor statuses (FIG. 9B).

Figure 10B:
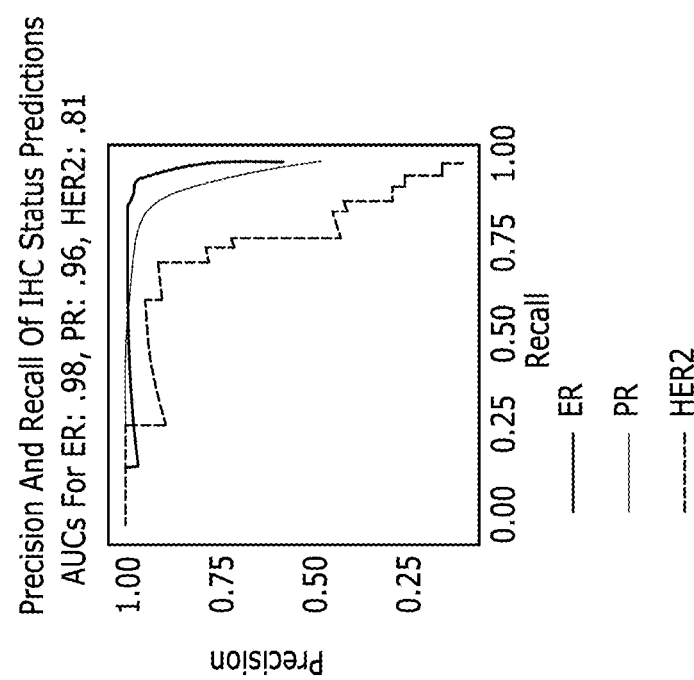
FIGS. 10A-10C are plots related to single-gene logistic model performance for ER, PR, and HER2 status prediction in the molecular sequenced cohort, in accordance with an example.
Figure 10A:
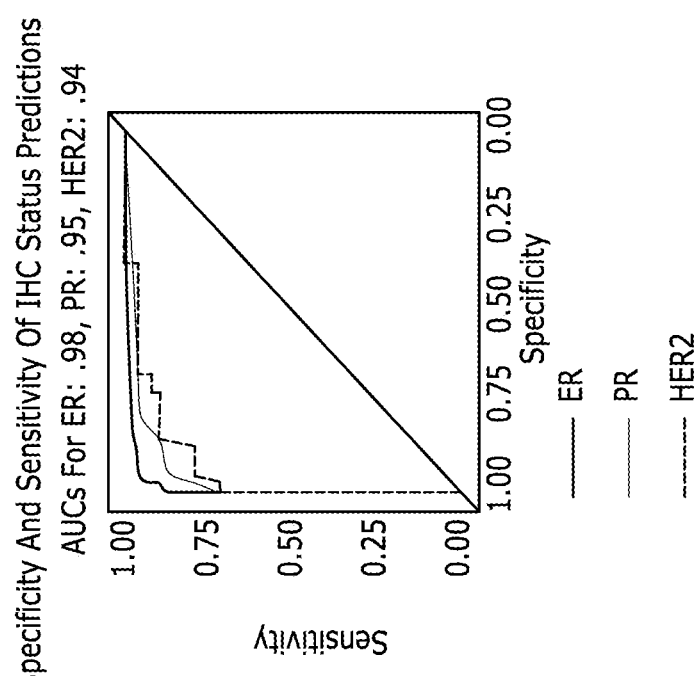
Figure 10C:
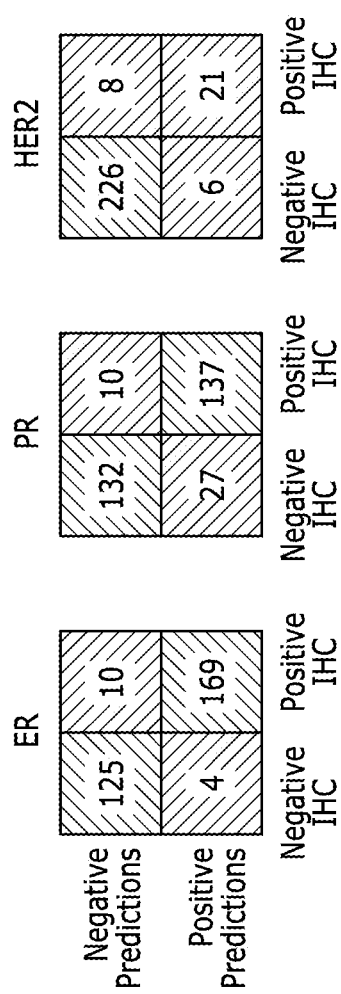

RNA-based receptor status predictions were highly accurate for ER (95.5%, AUROC 98.1%) and HER2 (94.6%, AUROC 93.8%) relative to abstracted status, while PR status was predicted with slightly lower accuracy (87.9%, AUROC 95.2%) (FIG. 10). Prediction accuracy for all receptors was 92.7%. A detailed overview of the validation data and model performance are available in Table 1. Patients with incompletely abstracted molecular subtypes (n=150) were classified by predicted receptor statuses from the transcriptomic model. Importantly, patients with equivocal HER2 statuses abstracted from IHC and/or FISH results (n=36) were predicted HER2+(n=7) or HER2− (n=29) by the model.

Figure 11A:
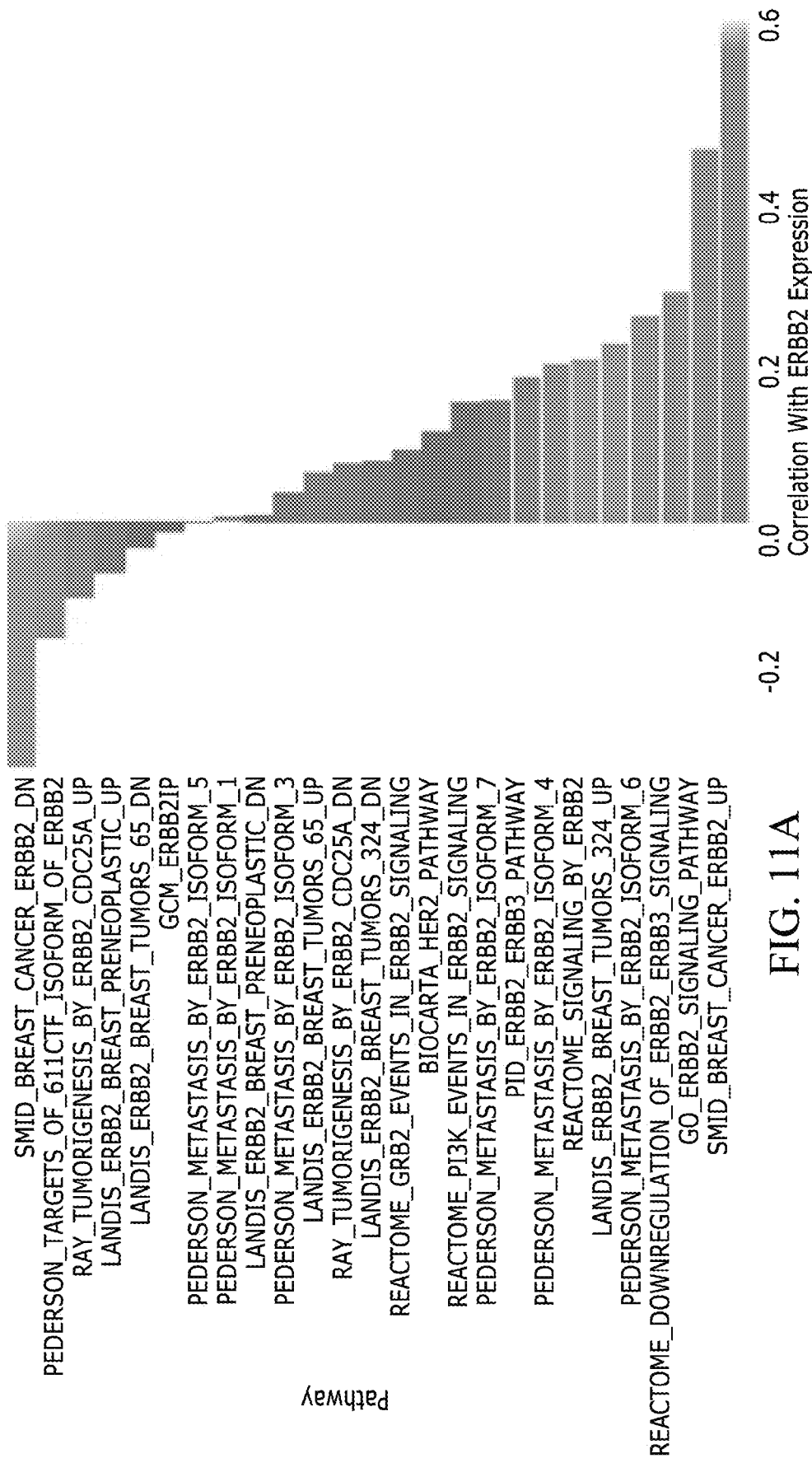
FIGS. 11A and 11B illustrated breast cancer pathway analyses from RNA-seq data of the molecular sequenced cohort according to MSigDB and Hallmark pathways, in accordance with an example.
Figure 11B:
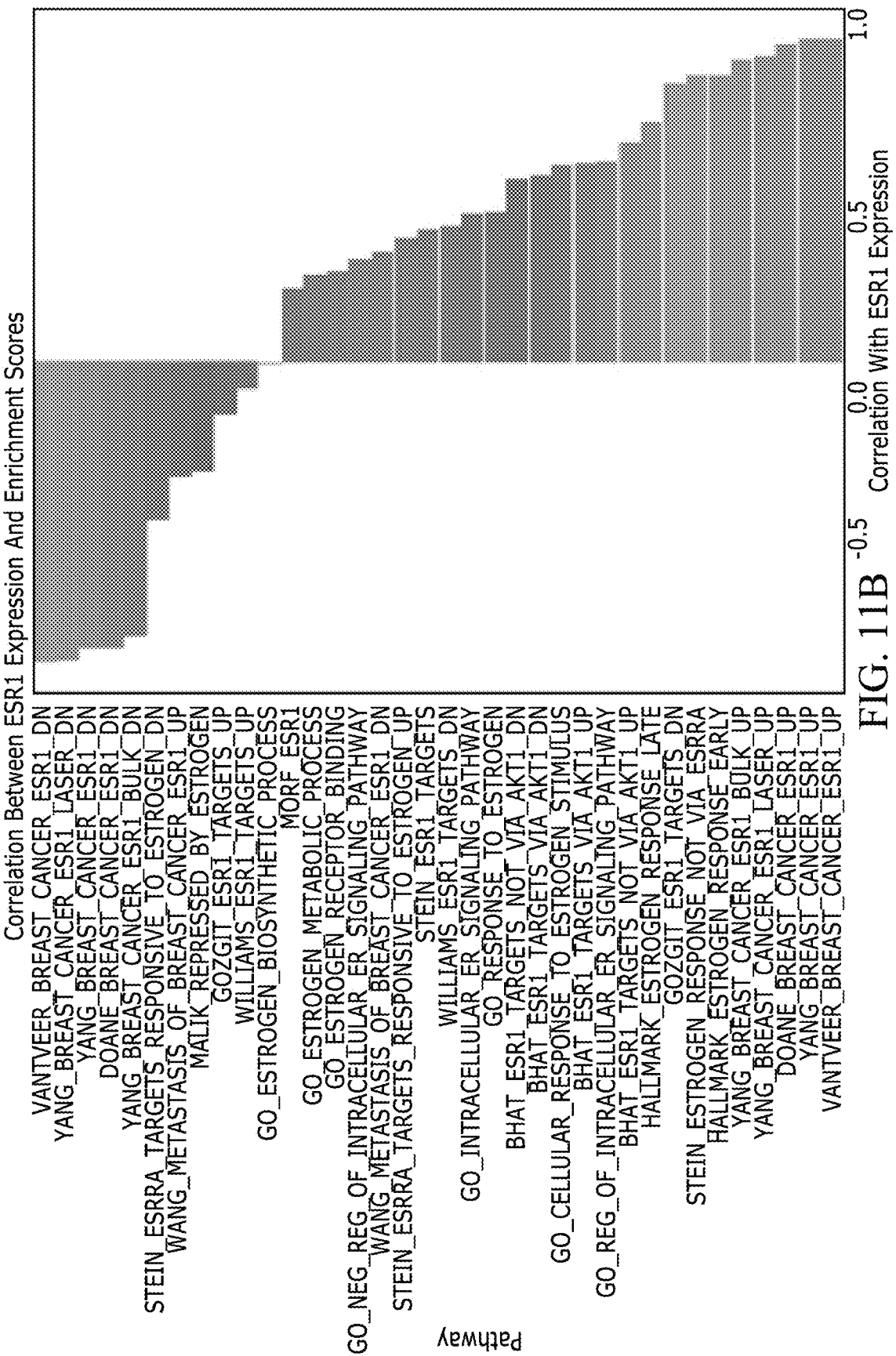
Figure 12A:
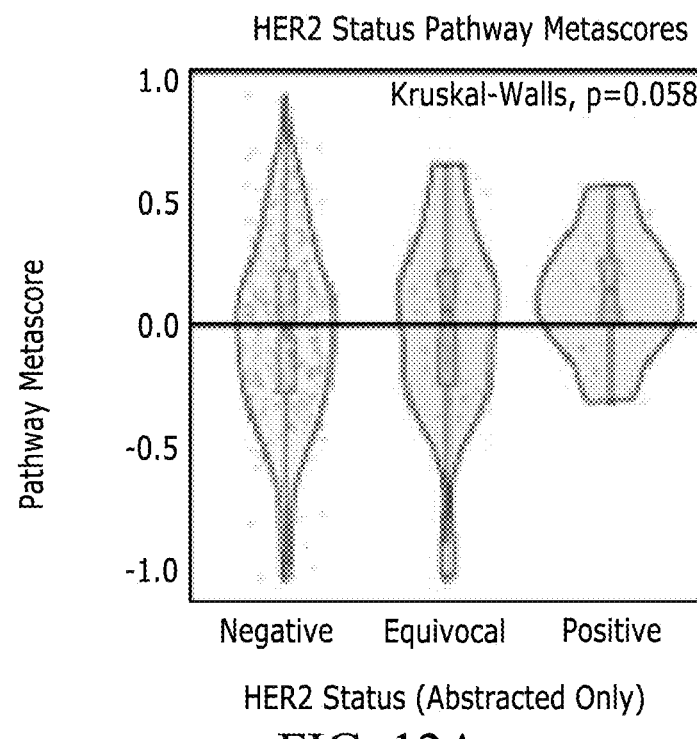
FIGS. 12A-12E are plots related to RNA-seq breast cancer pathway analyses of the molecular sequenced cohort, in accordance with an example. HER2 (FIG. 12A) and ER (FIG. 12B) pathway metascores for patients with abstracted HER2 IHC or FISH test results are shown.
Figure 12B:
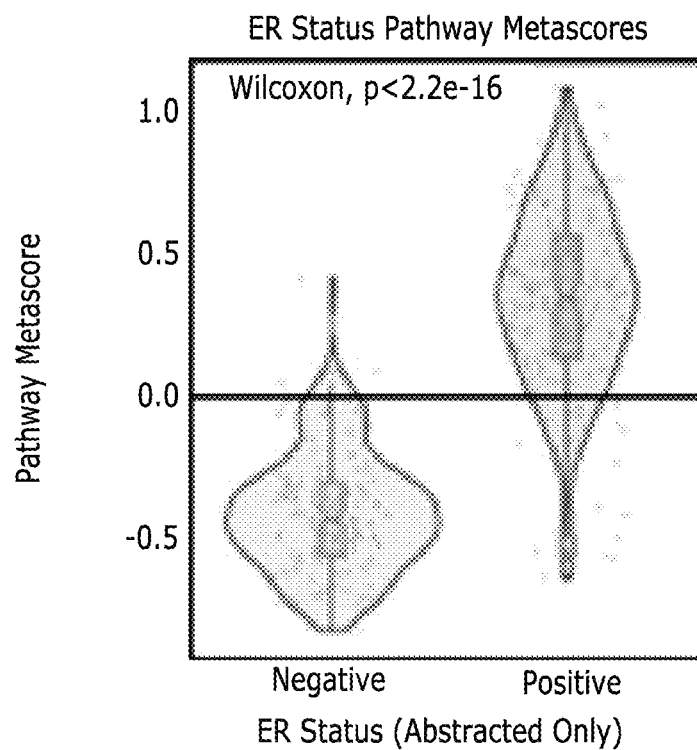
Figure 13:
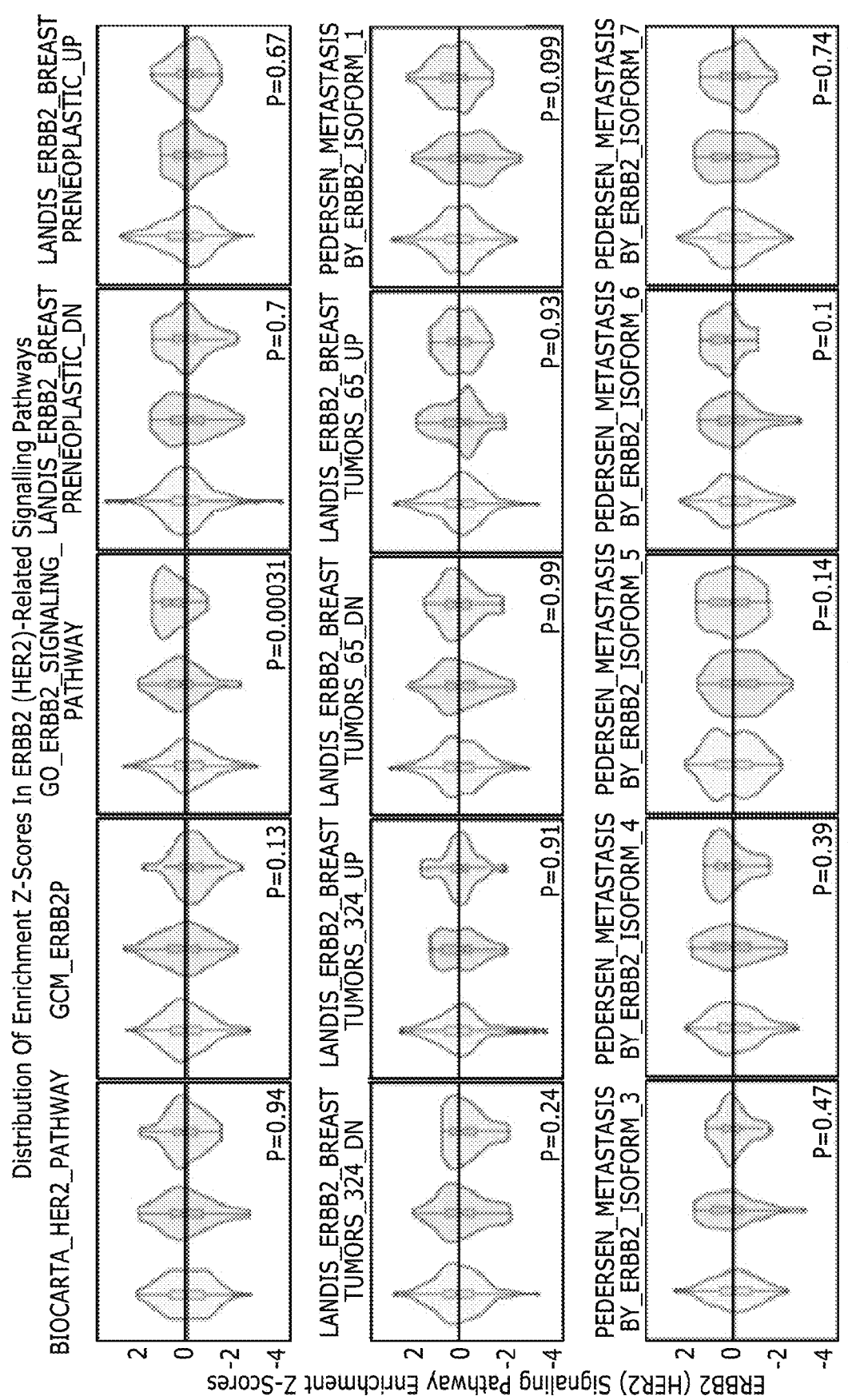
FIG. 13 illustrates plots of distribution of enrichment z-scores for each HER2− related pathway in MSigDB among patients in the molecular sequenced cohort. Patients with negative (blue), equivocal (orange), or positive (green) abstracted or predicted HER2 test results are shown. The P-values listed for each pathway represent the results of a Kruskal-Wallis test for the difference between enrichment scores from HER2−, HER2− equivocal, and HER2+ patients.
Figure 13:
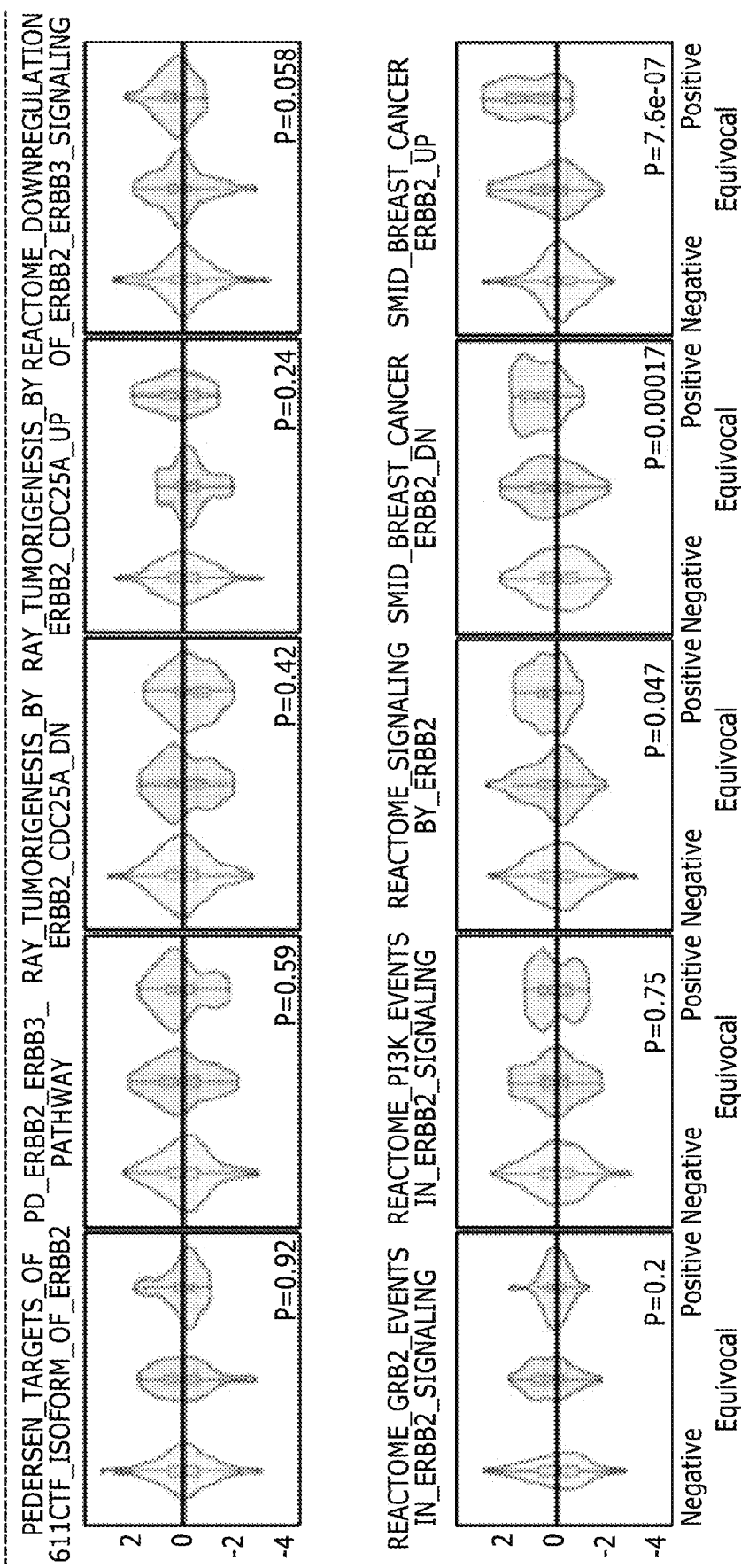
Figure 14:
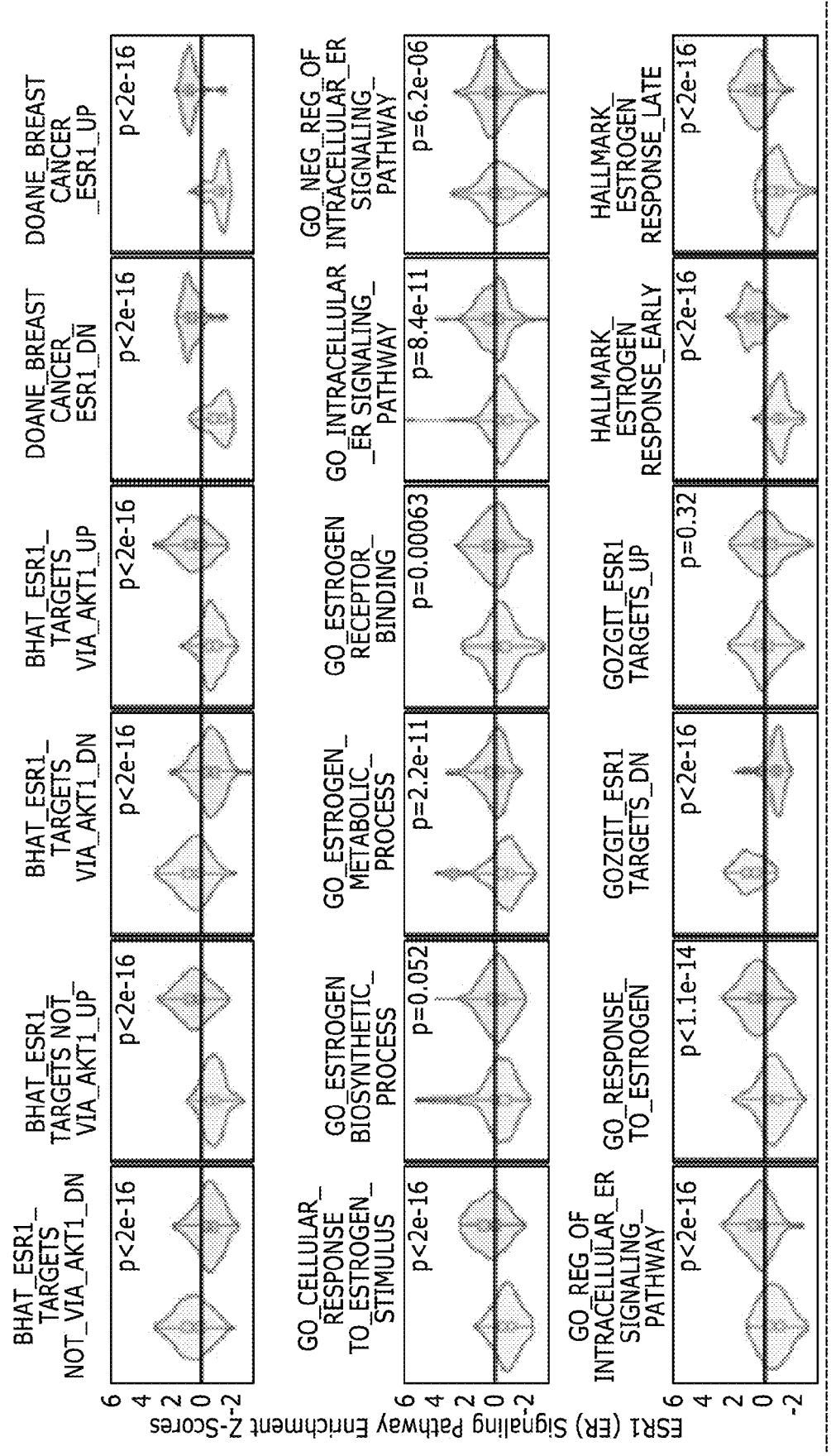
FIG. 14 illustrates plots of distribution of enrichment z-scores for each ER-related pathway in MSigDB among patients in the molecular sequenced cohort. Patients with negative (blue) or positive (green) abstracted or predicted ER test results are shown. The P-values listed for each pathway represent the results of a Wilcox rank sum test for the difference between enrichment z-scores from ER+ and ER− patients.
Figure 14:
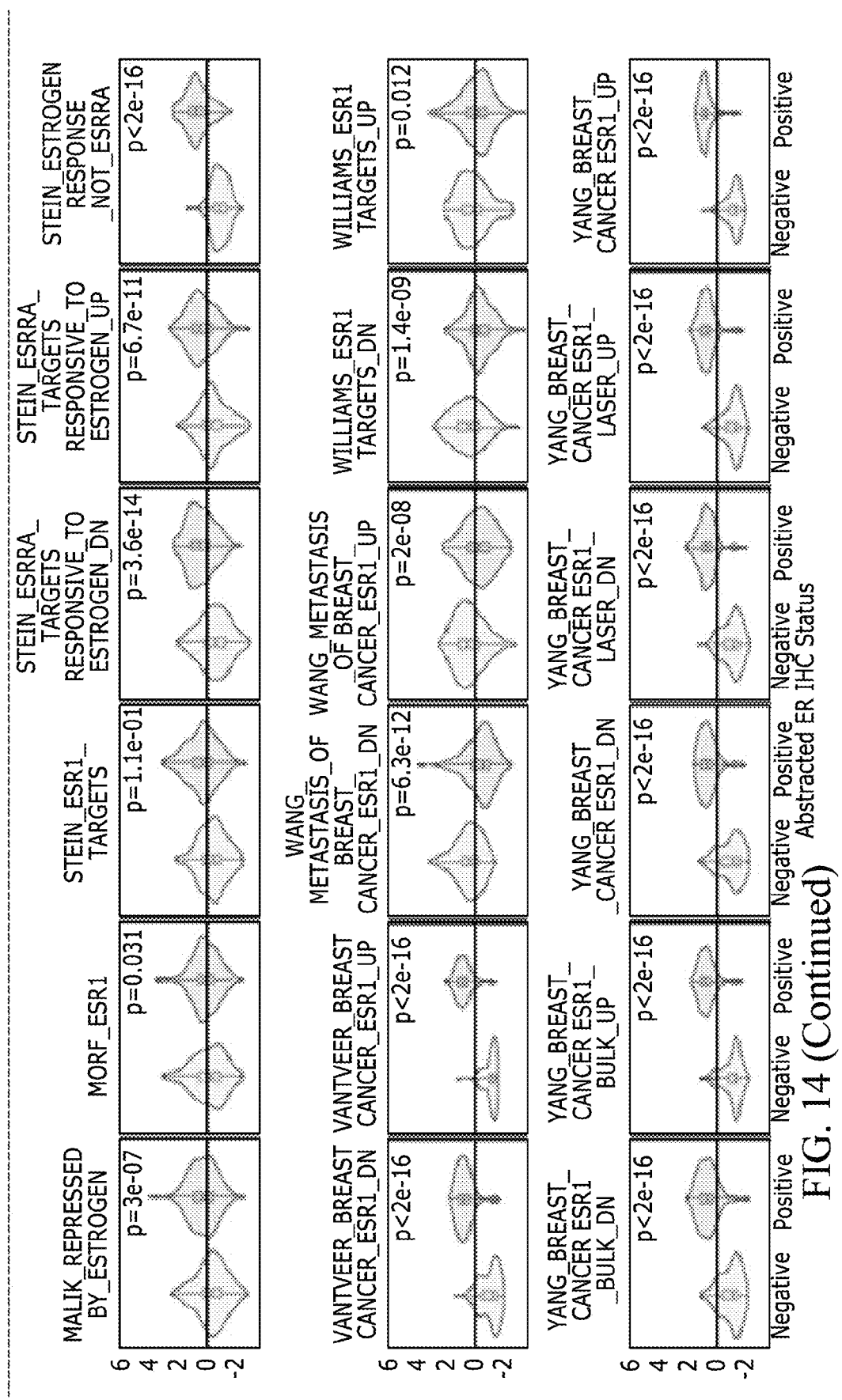

RNA-based HER2 and ER pathway analyses: To further evaluate the potential for RNA-seq to enhance breast cancer clinical data, a gene set enrichment analysis was conducted using the MSigDB database. First, we assessed whether measuring the activity of signaling pathways may resolve ambiguous or equivocal IHC and FISH test results. Multiple gene sets that putatively measure such pathway activity were identified by searching for "ERBB2," "HER2," "ESR1," or "Estrogen" in the MSigDB database (FIG. 11A and FIG. 11B). Results of the pathway analyses were expressed as metascores to avoid the bias introduced when selecting a single pathway. HER2 IHC-positive and FISH-positive samples were enriched for HER2 activity metascores as expected, but the HER2 signaling results contained substantial variability in pathway activity (FIG. 12A). Notably, the GO_ERBB2_SIGNALING_PATHWAY, which directly measures HER2 activity, exhibited a robust correlation with HER2 expression (r=0.453) (FIG. 11A) and significantly different enrichments between HER2 statuses (P=0.00031) (FIG. 13). While ER enrichment scores were more distinct between IHC-positive and IHC-negative patients, consistent with the relatively higher reliability of ER IHC compared with HER2 tests, variability was also observed in the ER signaling results (FIG. 12B, FIG. 14).

Figure 12C:
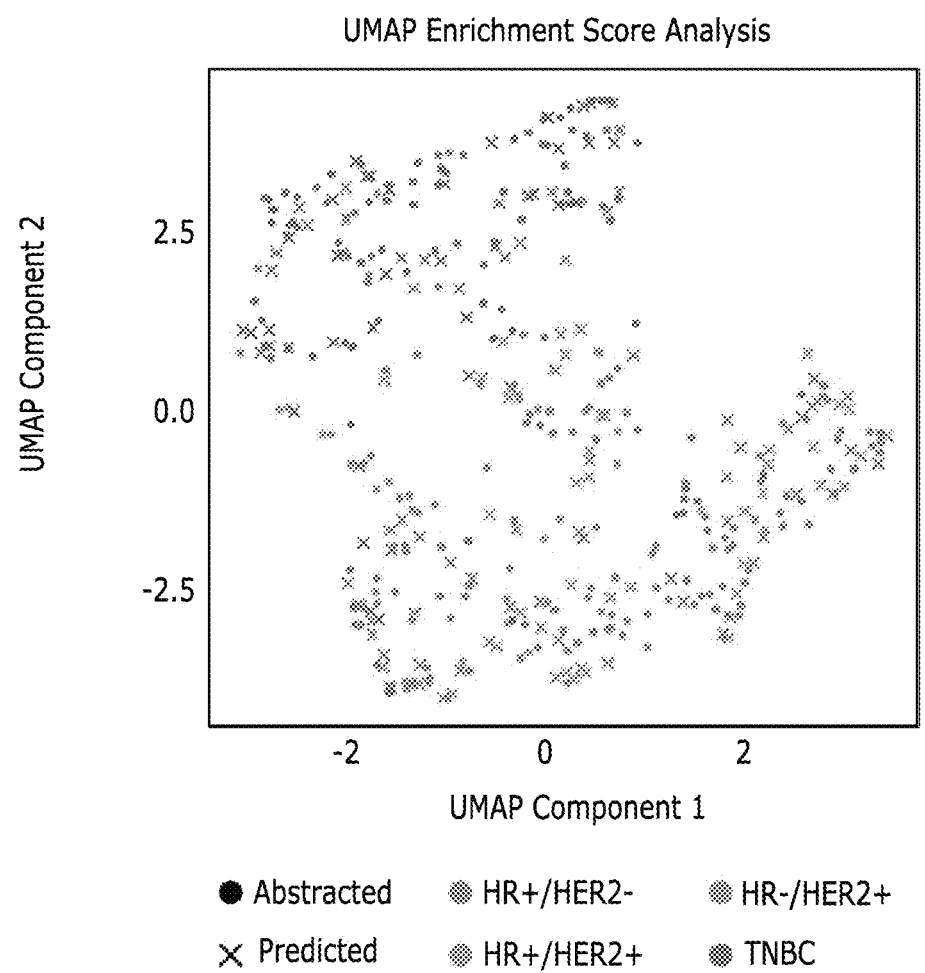
Figure 12D:
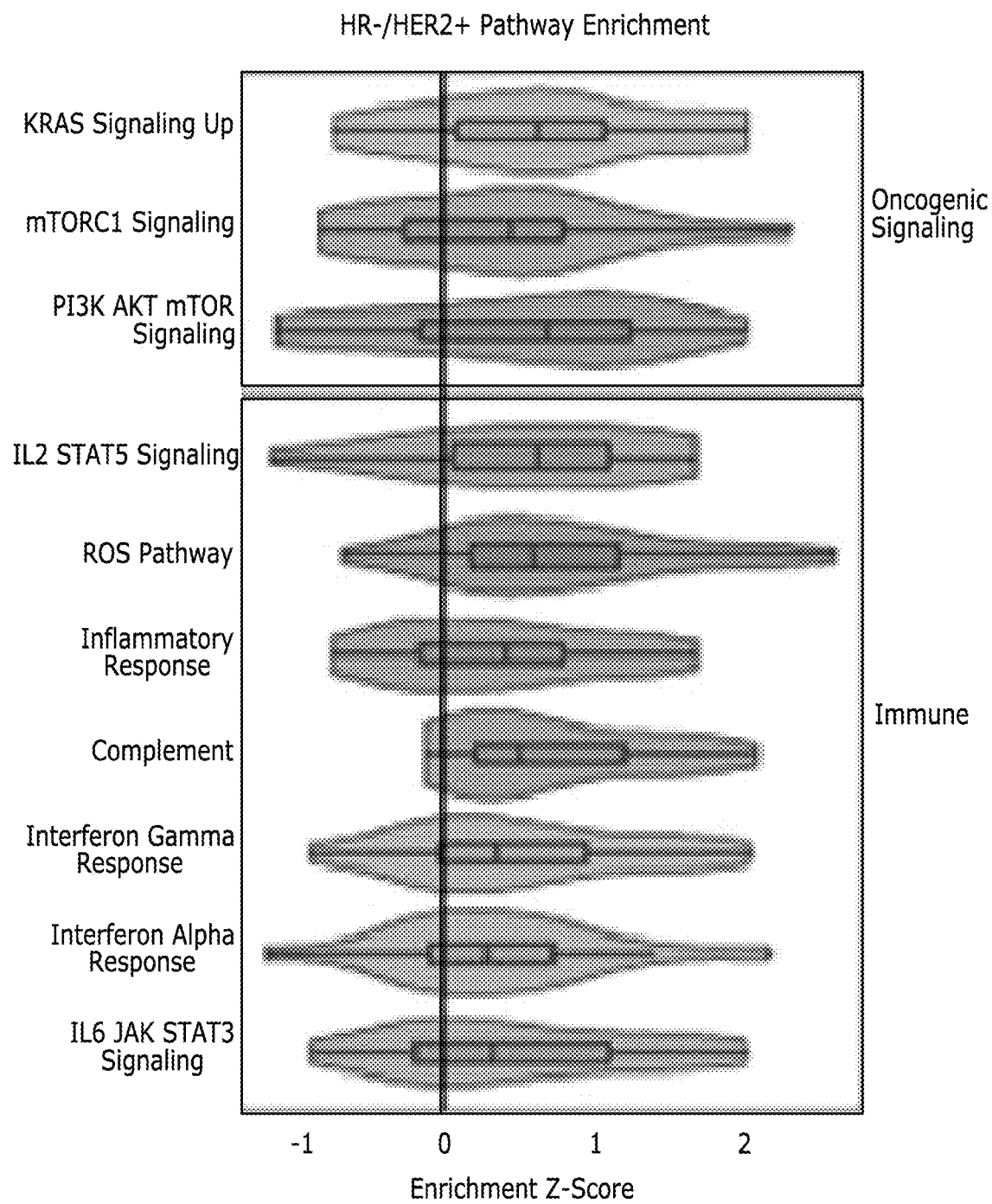
Figure 12E:
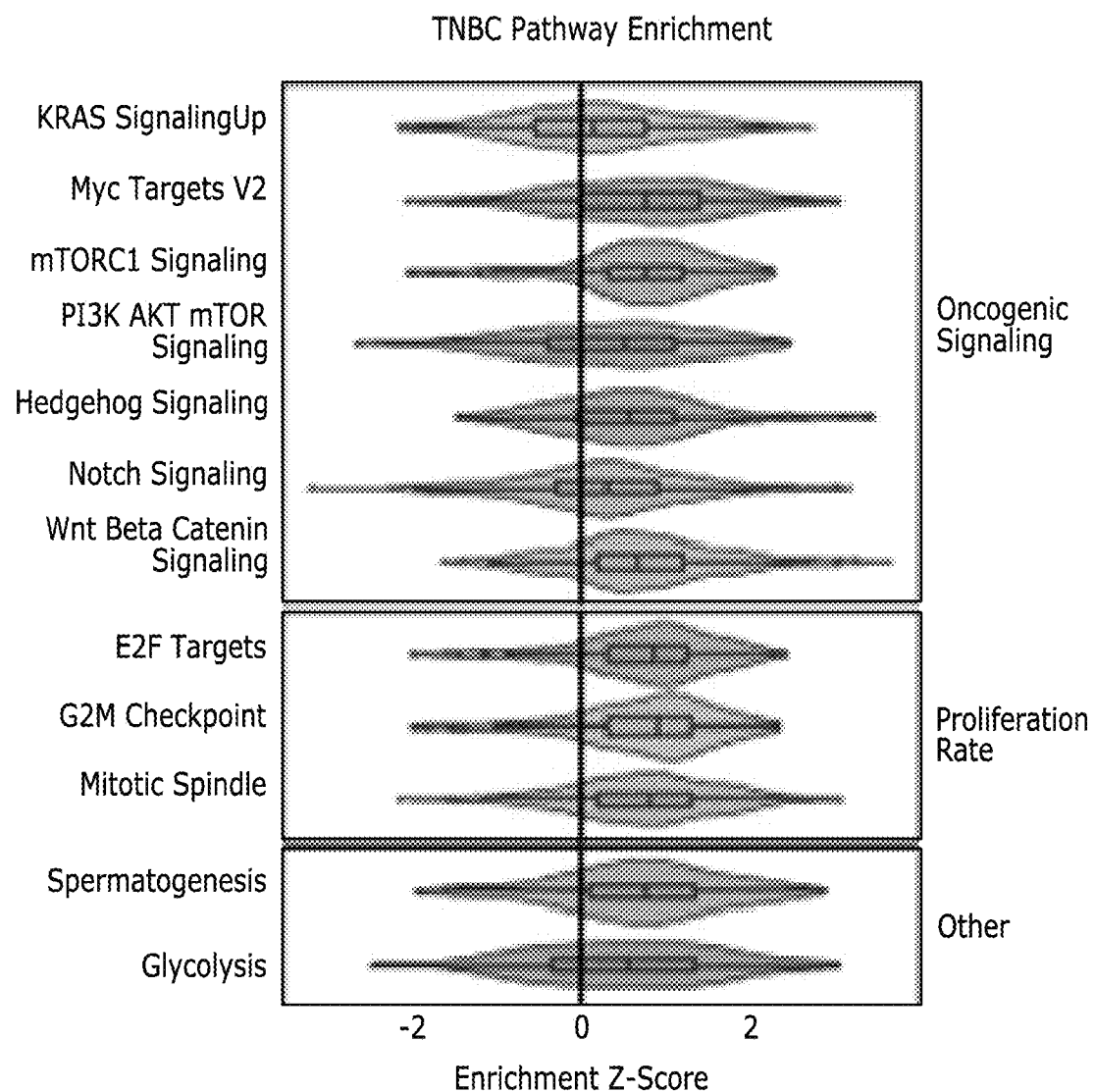
Figure 15A:
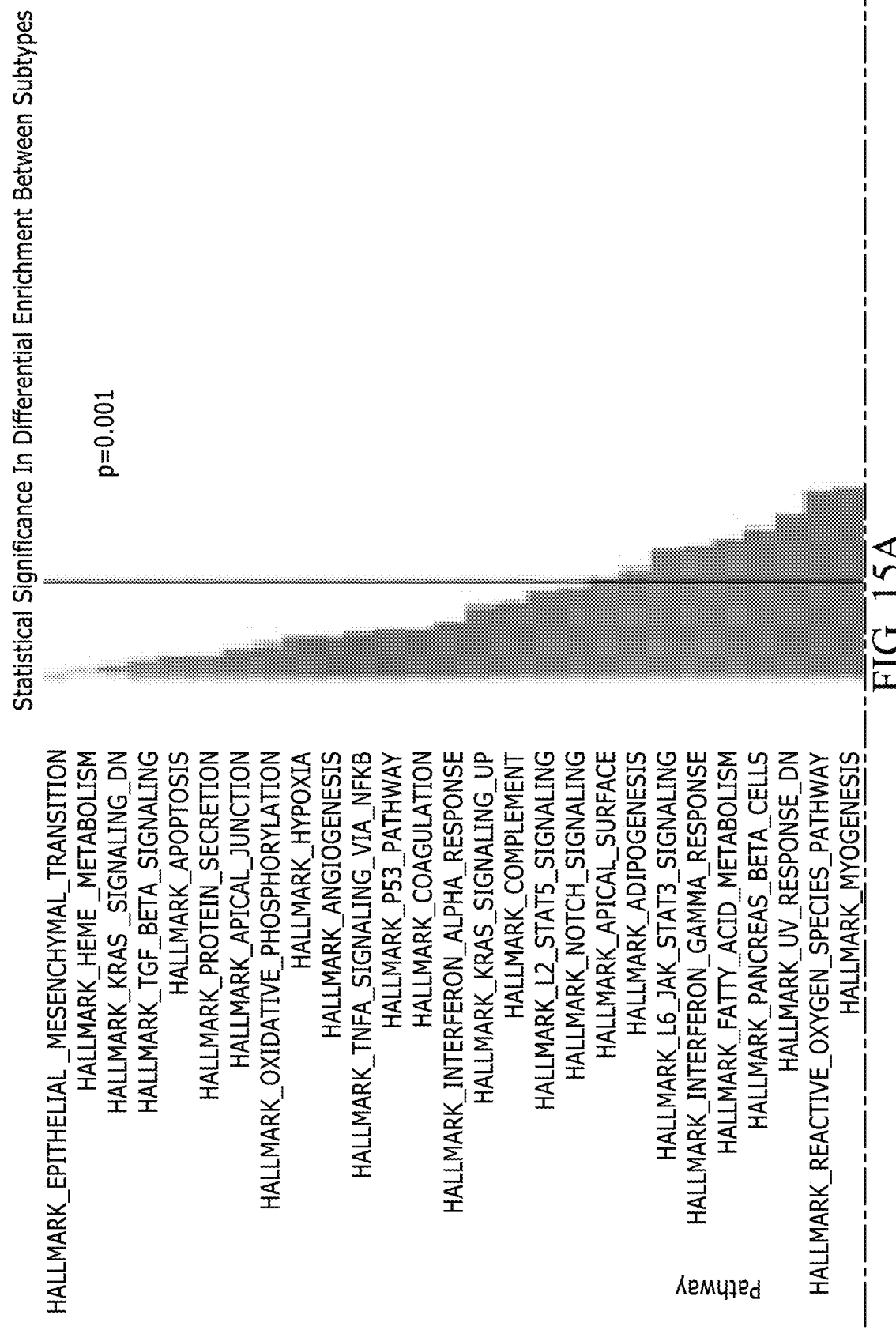
FIG. 15A is a plot illustrating, for each Hallmark pathway, the significance of differential enrichment between molecular subtypes was determined by a Kruskal-Wallis test of the enrichment scores. The vertical line indicates P=0.001 and any value to the right of the line was considered significant.
Figure 15A:
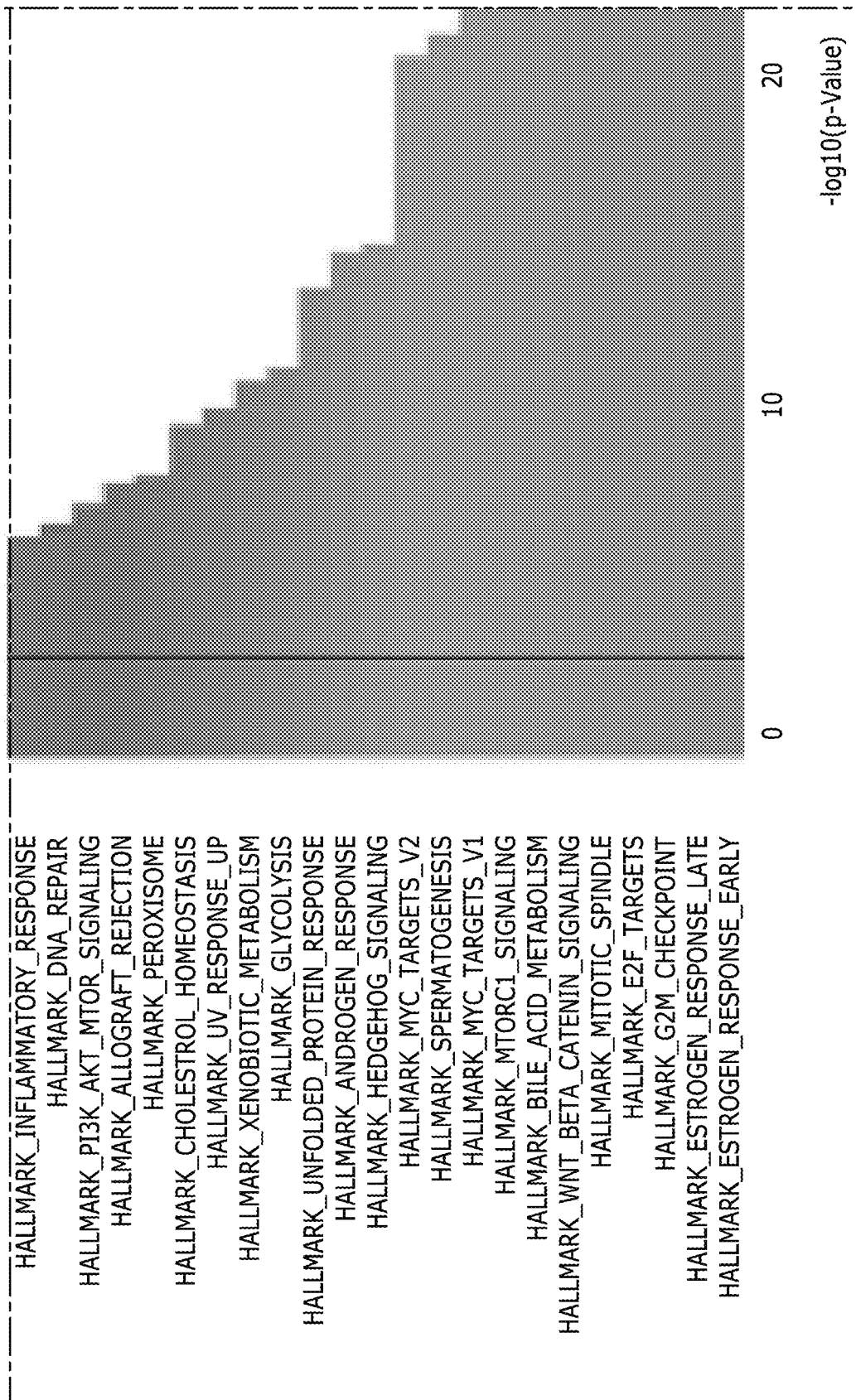
Figure 15B:
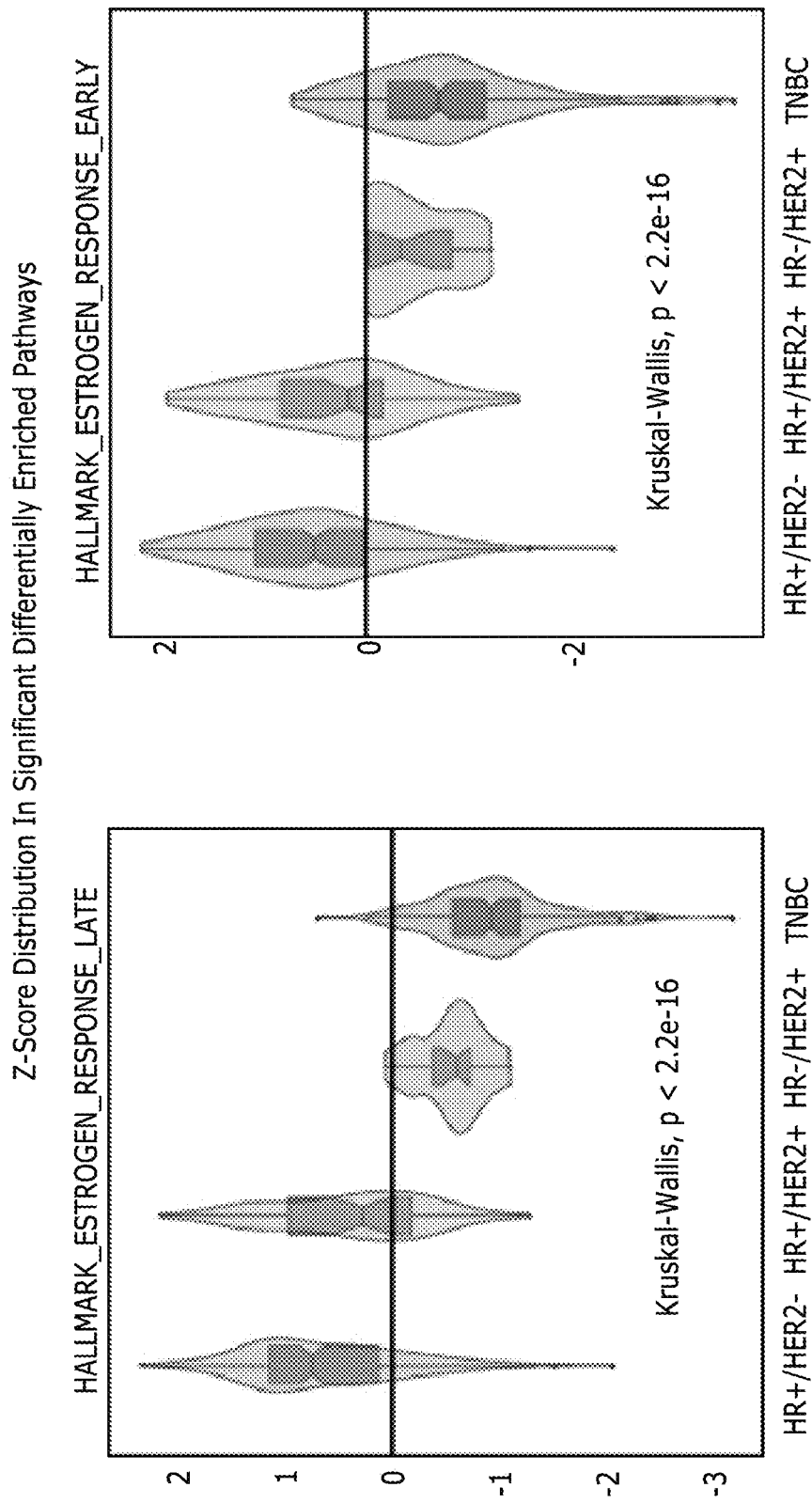
FIG. 15B illustrates distributions of z-scores among HR+/HER2− (blue), HR+/HER2+ (green), HR−/HER2+ (orange), and TNBC (grey) patients for the two estrogen response Hallmark pathways with the most significant differential enrichments between molecular subtypes.

Next, RNA-seq data were analyzed in relation to the highly curated Hallmark pathway gene sets to determine the differential activation of biological pathways between breast cancer subtypes. Most Hallmark pathways (32 of 50) exhibited significantly different enrichment scores between molecular subtypes (FIG. 15A). A UMAP using only scores from these 50 pathways recapitulated the TNBC clustering observed in the full-transcriptome UMAP (FIG. 12C). As expected, HR+ samples, but not HR− or TNBC samples, were highly enriched for two pathways related to estrogen signaling (FIG. 15B). Among HR−/HER2+ cancers, we observed enrichment for pathways known to be downstream of HER2, RAS, and mTOR (FIG. 12D). HER2-driven tumors also showed enrichment for all immune-related Hallmark pathways, a finding consistent with the literature. Many oncogenic signaling pathways were enriched in TNBC (FIG. 12E), including Wnt, mTOR, PI3K, Hedgehog, and Notch, consistent with TNBC tumors' reliance on ER−, PR−, and HER2-independent pathways. TNBC samples were also enriched for pathways related to mitotic index, as expected due to their relatively high growth rate, glycolysis, which is consistent with their elevated Warburg effect and potentially targetable, and cancer/testis antigens.

Figure 16:
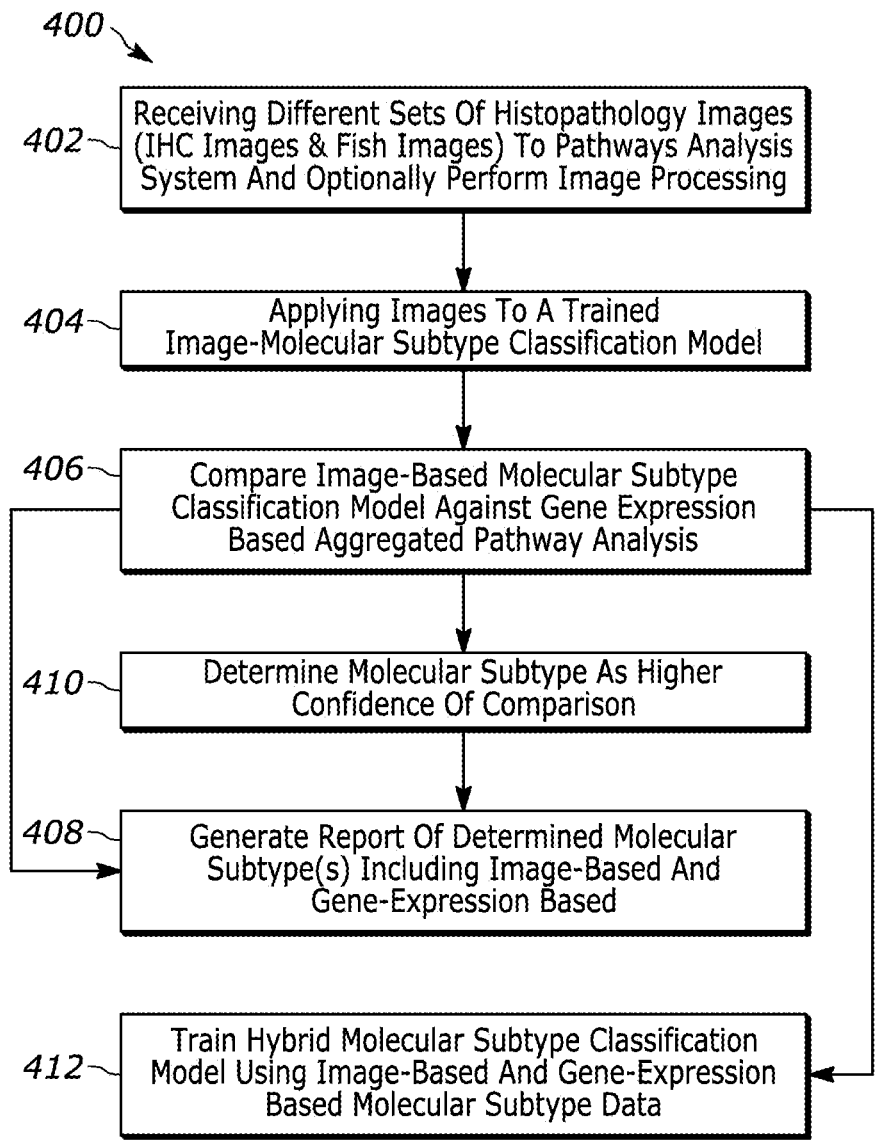
FIG. 16 is a block diagram of an example process for performing a hybrid pathway analysis and molecular subtype identification from gene expression and image data as performed by the processing system of FIG. 1, in accordance with an example.

The third type of pipeline in the computing device 102, is the hybrid pipeline 150 uses pathway data obtained from gene expression data and molecular subtype data obtained from histopathology analysis to inform one another to generate an aggregated pathway scores that can be used for more accurate assessment of molecular subtype. An example implementation of the pipeline 150 is shown in FIG. 16 and the process 400. At a block 402, histopathology images, such as IHC and/or FISH images, are obtained at a pathways analysis system. In some examples, image processing is performed similar to that of process 302 in FIG. 3. At a block 404, the images are provided to a trained image-molecular subtype classification model, which may be implemented by the trained molecular subtype neural network 158. In the process 400, however, instead of examining for discordance between different image set, the classification model of process 404 may be trained to classify one or multiple types of image sets. For example, the classification model may be trained to classify IHC images only or trained to classify FISH images only. In this way, existing image classification models may be used. In some examples, the classification model of the process 404 contains classification models for numerous different histopathology image set types.

For example, in various embodiments, different sets of histopathology images may be received, each set determined using a different image generation process, such as a first set of images are IHC stain images and a second set of images are FISH images. Other image set types include Hematoxylin and eosin (H&E) stained images. At the block 404, initial image processing may be performed on these received images, for example, by the imaging processing stage 154. For example, the images may be analyzed on a whole slide basis or on a tile basis. For the latter, in some examples, the images are segmented into a plurality of tile images by applying a tiling mask to the digital images, where each tile image contains a portion of the digital image. These tile masks may generate tiles of the same size or different sizes, tiles that may be rectangular in shape, square in shape, or other, etc.

At the block 404, the images, whole slide or tile, may be provided to a trained image-based molecular subtype classification model, such as the model 158. The classification model may be a neural network, such as convolutional neural network. In some examples, the classification model is tile-resolution Fully Convolutional Network (FCN) classification model. In some examples, the classification model is a tissue classification model, trained using a set of training images annotated identifying different tissue types, where those training images include histopathology images fed to a deep learning framework that trains the tissue classification model using a convolution neural network. In some examples, the classification model is a cell segmentation classification model, trained using a set of training images annotated identifying cell borders, cell interiors, and cell exteriors, the training images being histopathology images fed to a deep learning framework that trains the cell seg-mentation classification model using a convolution neural network. In some examples, the classification model is a UNet classification model.

At a block 406, the resulting molecular subtype from the classification process 404 is compared against a gene-expression derived, aggregated pathway analysis data and molecular subtype determination, for example, as may be performed by the process 200 of FIG. 2. The comparison of block 406 allows for comparison of generally less accurate determinations, such as HER2+ or HER2− determinations made from IHC classification models, to highly accurate results based on aggregated pathway analysis using a gene expression based pipeline. That comparison applies to FISH analysis of HER2, as well, even though FISH based classification models are generally more accurate than IHC based ones. At the block 406, the comparison may identify discordance between the resulting molecular subtype data and pass the differing determinations to a report generator block 408. The resulting report may include data from both histopathology image derived determinations and gene-expression derived determinations. In some examples, the block 406 passes pathway aggregation scoring, molecular subtype, and gene expression data for one or more of the set of pathways to the block 408 for report generation.

In some examples, a block 410 performs a quantitative comparison between the determinations to determine if one of the determinations, more likely the gene-expression derived one, has a high level of confidence over the other. In such examples, the block 406 may determine the molecular subtype as the one with the highest confidence level value, for example by generating a probability of each pathway prediction using a softmax function. This molecular subtype value is transmitted to process 408 for inclusion in a generated report.

In various embodiments, the pathways, pathway scores, and gene expression values from the gene-expression pipeline are provided by the block 406 to train a hybrid molecular subtype classification model at a block 4. The hybrid classification model may be trained with histopathology images (e.g., IHC images and/or FISH images) and gene expression and pathway scores from gene expression data (e.g., from RNA-seq data) corresponding to the same cohort samples. The hybrid classification model may perform multiple gene classifications on subsequently received histopathology images, for example, allowing for multiple different subtypes to be classified. The hybrid classification model may be a neural network, such as convolutional neural network, configured as a whole image classifier or a tile-based classifier, like that of the classification model in block 304.

Figure 17:
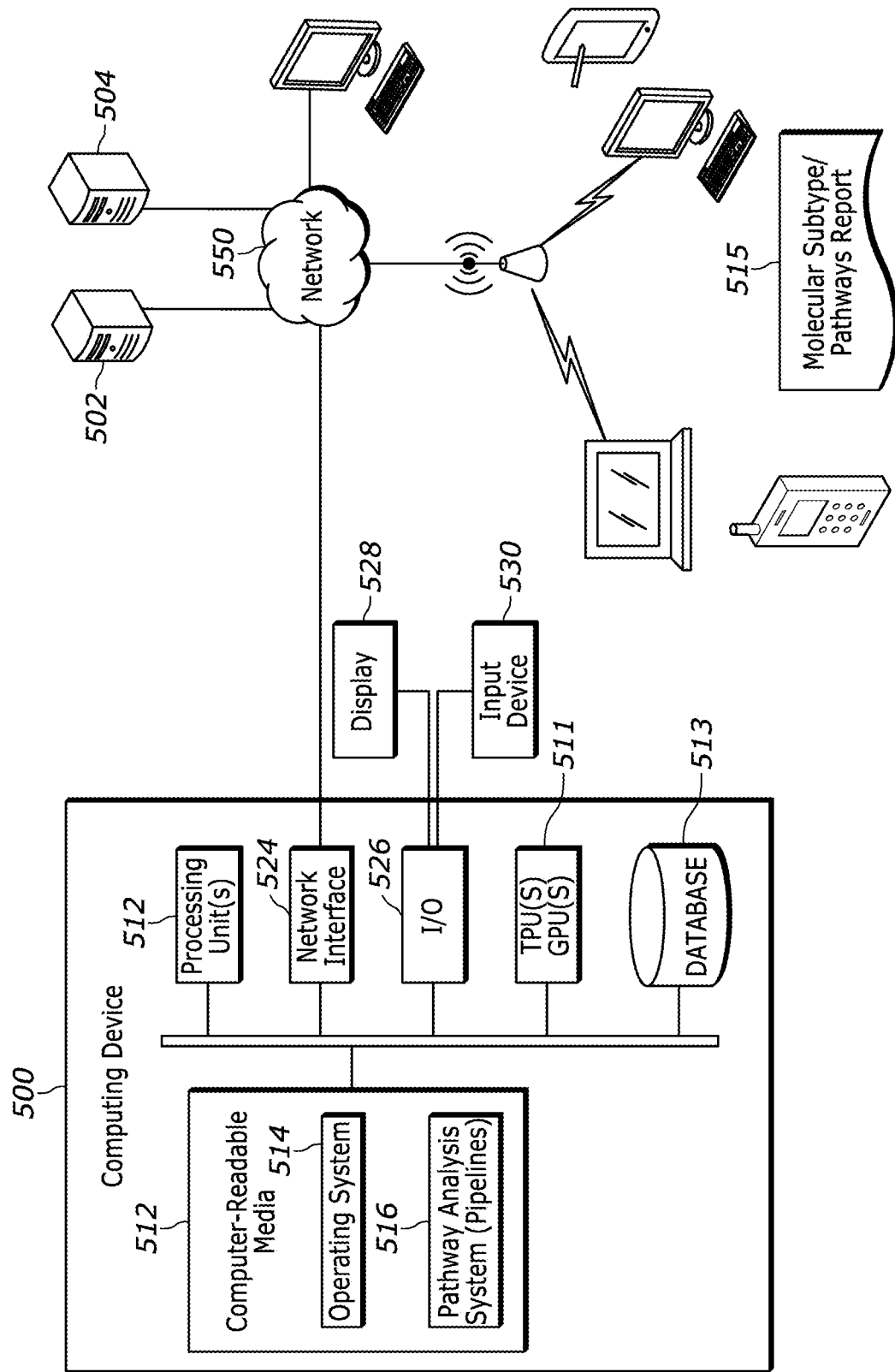
FIG. 17 illustrates an example computing device for implementing the system of FIG. 1 and the processes of FIGS. 2, 3, and 16, in accordance with an example.

FIG. 17 illustrates an example computing device 500 for implementing the pathway analysis computing device 100 of FIG. 1. As illustrated, the computing device 100 may be implemented on the computing device 500 and in particular on one or more processing units 510, which may represent Central Processing Units (CPUs), and/or on one or more or Graphical Processing Units (GPUs) 511, including clusters of CPUs and/or GPUs, and/or one or more tensor processing units (TPU) (also labeled 511), any of which may be cloud based. Features and functions described for the computing device 100 may be stored on and implemented from one or more non-transitory computer-readable media 512 of the computing device 500. The computer-readable media 512 may include, for example, an operating system 514 and a pathway analysis system (e.g., pipelines, etc.) 516 having elements corresponding to that of the pipelines 130, 140, and 150, and pre-processing layer 120 and molecular subtype layer 160. More generally, the computer-readable media 512 may store trained classification models, executable code, etc. used for implementing the techniques herein. The computer-readable media 512 and the processing units 510 and TPU(S)/GPU(S) 511 may store histopathology images, gene expression data, pathway expression data, pathway scores, aggregated pathway scores, enrichment scores, molecular subtype classification data, and other data herein in one or more databases 513.

The computing device 500 includes a network interface 524 communicatively coupled to the network 550, for communicating to and/or from a portable personal computer, smart phone, electronic document, tablet, and/or desktop personal computer, or other computing devices. The computing device further includes an I/O interface 526 connected to devices, such as digital displays 528, user input devices 530, etc. In some examples, as described herein, the computing device 500 generates molecular subtype/pathway data as an electronic document 515 that can be accessed and/or shared on the network 550.

In the illustrated example, the system 100 is implemented on a single server 500. However, the functions of the system 100 may be implemented across distributed devices 500, 502, 504, etc. connected to one another through a communication link. In other examples, functionality of the system 100 may be distributed across any number of devices, including the portable personal computer, smart phone, electronic document, tablet, and desktop personal computer devices shown. In other examples, the functions of the computing device 100 may be cloud based, such as, for example one or more connected cloud TPU (s) customized to perform machine learning processes. The network 550 may be a public network such as the Internet, private network such as research institution's or corporation's private network, or any combination thereof. Networks can include, local area network (LAN), wide area network (WAN), cellular, satellite, or other network infrastructure, whether wireless or wired. The network can utilize communications protocols, including packet-based and/or datagram-based protocols such as internet protocol (IP), transmission control protocol (TCP), user datagram protocol (UDP), or other types of protocols. Moreover, the network can include a number of devices that facilitate network communications and/or form a hardware basis for the networks, such as switches, routers, gateways, access points (such as a wireless access point as shown), firewalls, base stations, repeaters, backbone devices, etc.

The computer-readable media may include executable computer-readable code stored thereon for programming a computer (e.g., comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units of the computing device 1300 may represent a CPU-type processing unit, a GPU-type processing unit, a TPU-type processing unit, a field-programmable gate array (FPGA), another class of digital signal processor (DSP), or other hardware logic components that can be driven by a CPU.

It is noted that while example classification models and neural networks herein have been described as configured with example machine learning architectures (FCN configurations and UNET configurations), any number of suitable convolutional neural network architectures may be used. Broadly speaking, the classification models herein may implement any suitable statistical model (e.g., a neural network or other model implemented through a machine learning process) that will be applied to each of the received images. As discussed herein, that statistical model may be implemented in a variety of manners. In some examples, machine learning is used to evaluate training images and/or corresponding gene expression data to develop classifiers that correlate predetermined image features to specific categories of gene expressions or molecular subtypes. In some examples, image features can be identified as training classifiers using a learning algorithm such as Neural Network, Support Vector Machine (SVM) or other machine learning process. Once classifiers within the statistical model are adequately trained with a series of training images, the statistical model may be employed in real time to analyze subsequent images provided as input to the statistical model for predicting biomarker status. In some examples, when a statistical model is implemented using a neural network, the neural network may be configured in a variety of ways. In some examples, the neural network may be a deep neural network and/or a convolutional neural network. In some examples, the neural network can be a distributed and scalable neural network. The neural network may be customized in a variety of manners, including providing a specific top layer such as but not limited to a logistics regression top layer. A convolutional neural network can be considered as a neural network that contains sets of nodes with tied parameters. A deep convolutional neural network can be considered as having a stacked structure with a plurality of layers. The neural network or other machine learning processes may include many different sizes, numbers of layers and levels of connectedness. Some layers can correspond to stacked convolutional layers (optionally followed by contrast normalization and max-pooling) followed by one or more fully-connected layers. For neural networks trained by large datasets, the number of layers and layer size can be increased by using dropout to address the potential problem of overfitting. In some instances, a neural network can be designed to forego the use of fully connected upper layers at the top of the network. By forcing the network to go through dimensionality reduction in middle layers, a neural network model can be designed that is quite deep, while dramatically reducing the number of learned parameters.

A system for performing the methods described herein may include a computing device, and more particularly may be implemented on one or more processing units, for example, Central Processing Units (CPUs), and/or on one or more or Graphical Processing Units (GPUs), including clusters of CPUs and/or GPUs. Features and functions described may be stored on and implemented from one or more non-transitory computer-readable media of the computing device. The computer-readable media may include, for example, an operating system and software modules, or "engines," that implement the methods described herein. More generally, the computer-readable media may store batch normalization process instructions for the engines for implementing the techniques herein. The computing device may be a distributed computing system, such as an Amazon Web Services cloud computing solution.

The computing device includes a network interface communicatively coupled to network, for communicating to and/or from a portable personal computer, smart phone, electronic document, tablet, and/or desktop personal computer, or other computing devices. The computing device further includes an I/O interface connected to devices, such as digital displays, user input devices, etc.

The functions of the engines may be implemented across distributed computing devices, etc. connected to one another through a communication link. In other examples, functionality of the system may be distributed across any number of devices, including the portable personal computer, smart phone, electronic document, tablet, and desktop personal computer devices shown. The computing device may be communicatively coupled to the network and another network. The networks may be public networks such as the Internet, a private network such as that of a research institution or a corporation, or any combination thereof. Networks can include, local area network (LAN), wide area network (WAN), cellular, satellite, or other network infrastructure, whether wireless or wired. The networks can utilize communications protocols, including packet-based and/or datagram-based protocols such as Internet protocol (IP), transmission control protocol (TCP), user datagram protocol (UDP), or other types of protocols. Moreover, the networks can include a number of devices that facilitate network communications and/or form a hardware basis for the networks, such as switches, routers, gateways, access points (such as a wireless access point as shown), firewalls, base stations, repeaters, backbone devices, etc.

The computer-readable media may include executable computer-readable code stored thereon for programming a computer (for example, comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units of the computing device may represent a CPU-type processing unit, a GPU-type processing unit, a field-programmable gate array (FPGA), another class of digital signal processor (DSP), or other hardware logic components that can be driven by a CPU.

The methods and systems described above may be utilized in combination with or as part of a digital and laboratory health care platform that is generally targeted to medical care and research. It should be understood that many uses of the methods and systems described above, in combination with such a platform, are possible. One example of such a platform is described in U.S. patent application Ser. No. 16/657,804, titled "Data Based Cancer Research and Treatment Systems and Methods", and filed Oct. 18, 2019, which is incorporated herein by reference and in its entirety for all purposes.

In one example, where the platform includes a genetic analyzer system, the genetic analyzer system may include targeted panels and/or sequencing probes. An example of a targeted panel is disclosed, for example, in U.S. Prov. Patent Application No. 62/902,950, titled "System and Method for Expanding Clinical Options for Cancer Patients using Integrated Genomic Profiling", and filed Sep. 19, 2019, which is incorporated herein by reference and in its entirety for all purposes. An example of the design of next-generation sequencing probes is disclosed, for example, in U.S. Prov. Patent Application No. 62/924,073, titled "Systems and Methods for Next Generation Sequencing Uniform Probe Design", and filed Oct. 21, 2019, which is incorporated herein by reference and in its entirety for all purposes.

In one example, where the platform includes a bioinformatics pipeline, the methods and systems described above may be utilized after completion or substantial completion of the systems and methods utilized in the bioinformatics pipeline. As one example, the bioinformatics pipeline may return a set of binary files, such as one or more BAM files, reflecting RNA read counts aligned to a reference genome. The methods and systems described above may be utilized, for example, to ingest the RNA read counts and produce cellular pathway activation and/or predicted protein expression information as a result. Other inputs, such as DNA read counts, could also be used as explained herein.

As noted above, the pipeline may include an RNA data normalizer, for example, as disclosed in U.S. patent application Ser. No. 16/581,706, titled "Methods of Normalizing and Correcting RNA Expression Data", and filed Sep. 24, 2019, which is incorporated herein by reference and in its entirety for all purposes. The pipeline may include a genetic data deconvoluter, for example, as disclosed in U.S. Prov. Patent Application No. 62/786,756, titled "Transcriptome Deconvolution of Metastatic Tissue Samples", and filed Dec. 31, 2018, and U.S. Prov. Patent Application No. 62/924,054, titled "Calculating Cell-type RNA Profiles for Diagnosis and Treatment", and filed Oct. 21, 2019, which are incorporated herein by reference and in their entirety for all purposes. The deconvoluted information may then be passed on to other aspects of the platform, such as variant calling, RNA expression calling, or insight engines.

The pipeline may include an automated RNA expression caller. An example of an automated RNA expression caller is disclosed, for example, in U.S. Prov. Patent Application No. 62/943,712, titled "Systems and Methods for Automating RNA Expression Calls in a Cancer Prediction Pipeline", and filed Dec. 4, 2019, which is incorporated herein by reference and in its entirety for all purposes.

In another example, the methods and systems disclosed herein may be executed in one or more micro-services operating on the platform. In another example, one or more of such micro-services may be part of an order management system in the platform that orchestrates the sequence of events needed to conduct the disclosed methods at the appropriate time and in the appropriate order of events needed to execute genetic sequencing, such as the sequencing of a patient's tumor tissue or normal tissues for precision medicine deliverables to cancer patients. In another example, a bioinformatics microservice may include one or more sub-microservices for provisioning and executing various stages of a bioinformatics pipeline. One such stage of a bioinformatics pipeline includes the methods and systems described herein. A micro-services based order management system is disclosed, for example, in U.S. Prov. Patent Application No. 62/873,693, titled "Adaptive Order Fulfillment and Tracking Methods and Systems", filed Jul. 12, 2019, which is incorporated herein by reference and in its entirety for all purposes.

In another example, where the platform includes a report generation engine, the methods and systems described above may be utilized to create a summary report of information for presentation to a physician. For instance, the report may provide to the physician information about cellular pathway activation statuses and/or predicted protein expression levels. The report may include therapies and/or clinical trials matched based on a portion or all of the information. For example, the therapies may be matched according to the systems and methods disclosed in U.S. Prov. Patent Application No. 62/804,724, titled "Therapeutic Suggestion Improvements Gained Through Genomic Biomarker Matching Plus Clinical History", filed Feb. 12, 2019, which is incorporated herein by reference and in its entirety for all purposes. For example, the clinical trials may be matched according to the systems and methods disclosed in U.S. Prov. Patent Application No. 62/855,913, titled "Systems and Methods of Clinical Trial Evaluation", filed May 31, 2019, which is incorporated herein by reference and in its entirety for all purposes. The report may include a comparison of the results to a database of results from many specimens. An example of methods and systems for comparing results to a database of results are disclosed in U.S. Prov. Patent Application No. 62/786,739, titled "A Method and Process for Predicting and Analyzing Patient Cohort Response, Progression and Survival", and filed Dec. 31, 2018, which is incorporated herein by reference and in its entirety for all purposes. The information may be further used, sometimes in conjunction with similar information from additional specimens and/or clinical response information, to discover biomarkers or design a clinical trial.

In a third example, the methods and systems described above may be applied to organoids developed in connection with the platform. In this example, the methods and systems may be used to analyze genetic sequencing data derived from an organoid to provide information about cellular pathway activation statuses and/or predicted protein expression levels associated with the organoid. The report may include therapies matched based on a portion or all of the deconvoluted information. These therapies may be tested on the organoid, derivatives of that organoid, and/or similar organoids to determine an organoid's sensitivity to those therapies. For example, organoids may be cultured and tested according to the systems and methods disclosed in U.S. Prov. patent application Ser. No. 16/693,117, titled "Tumor Organoid Culture Compositions, Systems, and Methods", filed Nov. 22, 2019; U.S. Prov. Patent Application No. 62/924,621, titled "Systems and Methods for Predicting Therapeutic Sensitivity", filed Oct. 22, 2019; and U.S. Prov. Patent Application No. 62/944,292, titled "Large Scale Phenotypic Organoid Analysis", filed Dec. 5, 2019, which are incorporated herein by reference and in their entirety for all purposes.

In a fourth example, the systems and methods described above may be utilized in combination with or as part of a medical device or a laboratory developed test that is generally targeted to medical care and research. An example of a laboratory developed test, especially one that is enhanced by artificial intelligence, is disclosed, for example, in U.S. Patent Application No. 62/924,515, titled "Artificial Intelligence Assisted Precision Medicine Enhancements to Standardized Laboratory Diagnostic Testing", and filed Oct. 22, 2019, which is incorporated herein by reference and in its entirety for all purposes.

It should be understood that the examples given above are illustrative and do not limit the uses of the systems and methods described herein in combination with a digital and laboratory health care platform.

The feasibility of real-world data (RWD) analysis has increased alongside technological advances and regulatory support to continuously capture and integrate healthcare data sources. Several studies demonstrate the ability for real-world evidence (RWE) to guide clinical development strategies, expand product labels, and address knowledge gaps by examining clinical aspects not captured in clinical trials.

Despite recent advances and growing regulatory support, RWD from heterogenous structured and unstructured sources is often challenged by various technical barriers. Lack of standardization between electronic records, underpowered natural language processing tools, and uncontrolled extraneous variables may affect the validity of well-sourced RWE.

Our RWD analyses followed strict qualitative criteria to produce RWE of demographics, clinical characteristics, molecular subtype, treatment history, and survival outcomes from a large, heterogeneous database. Importantly, the results were mostly consistent with data from previous clinical studies, suggesting feasibility of generating valid RWE.

We also demonstrate the value of integrating omics data with RWD through the use of whole-transcriptome analyses in relevant breast cancer signaling pathways and a predictive model for receptor statuses.

These data provide rationale for use of the clinicogenomic database to generate RWE and conduct real-time, hypothesis-driven analyses of large RWD cohorts in the future. Clinicians may utilize these large-scale databases to circumvent the restrictive exclusion criteria of controlled studies, clarify real-world patient needs, and aid the development of clinical trials. Furthermore, our results suggest molecular data may bolster deficiencies in standard breast cancer diagnostic tests.

TABLE 1

Single-gene logistic model performance results for RNA-based predictions of ER, PR, and HER2 status in the Tempus molecular sequenced cohort.

| | Estrogen receptor (ER) | | | | Progesterone receptor (PR) | | | | Human epidermal growth factor receptor 2 (HER2) | | | |
|---|---|---|---|---|---|---|---|---|---|---|---|---|
| | Testing set Samples from this study (n = 308) | 10-fold cross-validation set | | | Testing set Samples from this study (n = 306) | 10-fold cross-validation set | | | Testing set Samples from this study (n = 261) | 10-fold cross-validation set | | |
| | | Primary and meta-static (n = 652) | Primary (n = 138) | Meta-static (n = 513) | | Primary and meta-static (n = 625) | Primary (n = 139) | Meta-static (n = 485) | | Primary and meta-static (n = 565) | Primary (n = 134) | Meta-static (n = 430) |
| Accuracy | 0.9545 | 0.8959 | 0.8900 | 0.8940 | 0.8791 | 0.8330 | 0.8268 | 0.8342 | 0.9464 | 0.9089 | 0.9267 | 0.9025 |
| Sensitivity | 0.9441 | 0.9360 | 0.8940 | 0.9428 | 0.9320 | 0.8890 | 0.7738 | 0.9160 | 0.7241 | 0.9301 | 0.9554 | 0.9194 |
| Specificity | 0.9690 | 0.8747 | 0.8845 | 0.8702 | 0.8302 | 0.7545 | 0.8755 | 0.7150 | 0.9741 | 0.7684 | 0.6667 | 0.7882 |

TABLE 1-continued

Single-gene logistic model performance results for RNA-based predictions of ER, PR, and HER2 status in the Tempus molecular sequenced cohort.

| | Estrogen receptor (ER) | | | | Progesterone receptor (PR) | | | | Human epidermal growth factor receptor 2 (HER2) | | | |
|---|---|---|---|---|---|---|---|---|---|---|---|---|
| | Testing set Samples from this study (n = 308) | 10-fold cross-validation set | | | Testing set Samples from this study (n = 306) | 10-fold cross-validation set | | | Testing set Samples from this study (n = 261) | 10-fold cross-validation set | | |
| | | Primary and meta-static (n = 652) | Primary (n = 138) | Meta-static (n = 513) | | Primary and meta-static (n = 625) | Primary (n = 139) | Meta-static (n = 485) | | Primary and meta-static (n = 565) | Primary (n = 134) | Meta-static (n = 430) |
| Precision | 0.9769 | 0.8046 | 0.8449 | 0.7850 | 0.8354 | 0.8348 | 0.8832 | 0.8217 | 0.7778 | 0.9613 | 0.9529 | 0.9626 |
| Recall | 0.9441 | 0.9360 | 0.8940 | 0.9428 | 0.9320 | 0.8890 | 0.7738 | 0.9160 | 0.7241 | 0.9301 | 0.9554 | 0.9194 |
| F1 | 0.9602 | 0.8620 | 0.8580 | 0.8537 | 0.8810 | 0.8597 | 0.8189 | 0.8643 | 0.7500 | 0.9450 | 0.9531 | 0.9399 |
| AUROC | 0.9811 | 0.9580 | 0.9718 | 0.9580 | 0.9517 | 0.8848 | 0.9178 | 0.8786 | 0.9388 | 0.9394 | 0.9656 | 0.9307 |
| Training sample size (pos./neg.) | — | 422/230 | 78/60 | 343/170 | — | 261/364 | 61/78 | 199/286 | — | 83/482 | 17/117 | 66/364 |
| Testing sample size (pos./neg.) | 179/129 | 10% | 10% | 10% | 147/159 | 10% | 10% | 10% | 29/232 | 10% | 10% | 10% |

TABLE 2

Patient demographics and clinical characteristics of the clinical abstraction and molecular sequenced cohorts at initial diagnosis

| | | Clinical Abstraction Cohort (N = 4,000) | Molecular Sequenced Cohort (N = 400) |
|---|---|---|---|
| Gender, n (%) | Female | 3,970 (99.3%) | 396 (99.0%) |
| | Male | 30 (0.7%) | 4 (1.0%) |
| Race, n (%)* | White | 3,332 (83.3%) | 185 (77.1%) |
| | Black/AA | 523 (13.1%) | 35 (14.6%) |
| | Asian or PI | 145 (3.6%) | 13 (5.4%) |
| | Other | 0 | 7 (2.9%) |
| | Unknown | 0 | 160 |
| Medium age (IQR) | | 61 (51.8-70.2) | 55.8 (45.2-68.4) |
| Stage, n (%)* | 0 | 42 (1.1%) | 0 |
| | I | 1,986 (49.6%) | 30 (13.9%) |
| | II | 1,333 (33.3%) | 83 (38.4%) |
| | III | 420 (10.5%) | 46 (21.3%) |
| | IV | 219 (5.5%) | 57 (26.4%) |
| | Unknown | 0 | 184 |
| Histological subtype, n (%)* | Invasive ductal | 3,095 (77.4%) | 267 (75.0%) |
| | Invasive lobular | 345 (8.6%) | 23 (6.5%) |
| | Invasive carcinoma NOS | 214 (5.4%) | 20 (5.6%) |
| | Invasive ductal/lobular | 167 (4.2%) | 20 (5.6%) |
| | Mucinous (colloid) | 61 (1.5%) | 0 |
| | Ductal in situ | 45 (1.1%) | 4 (1.1%) |
| | Tubular | 31 (0.8%) | 1 (0.3%) |
| | Papillary | 15 (0.4%) | 1 (0.3%) |
| | Inflammatory | 8 (0.2%) | 3 (0.8%) |
| | Metaplastic | 6 (0.1%) | 12 (3.4%) |
| | Other | 6 (0.1%) | 3 (0.8%) |
| | Medullary | 4 (0.1%) | 0 |
| | Lobular in situ | 1 (0.03%) | 1 (0.3%) |
| | Unmapped malignancy | 1 (0.03%) | 0 |
| | Phyllodes | 1 (0.03%) | 1 (0.3%) |
| | Unknown | 0 | 44 |
| Menopausal status, n (%)* | Postmenopausal | 1,784 (87.4%) | 67 (91.8%) |
| | Premenopausal | 258 (12.6%) | 6 (8.2%) |
| | Unknown | 1,928 | 313 |
| | Not applicable† | 30 | 4 |

IQR, interquartile range;
AA, African American;
PI, Pacific Islander;
NOS, not otherwise specified
*Patients with unknown, unreported, or not applicable characteristics/demographic data were not included in population percentage comparisons.
†Represents male patients in the cohort.

TABLE 3

Inter-test comparison of HER2 status from IHC and FISH results among patients in the clinical abstraction cohort with both tests conducted at initial diagnosis (N = 709).

| HER2 Status | IHC Positive (n = 82) | IHC Equivocal (n = 445) | IHC Negative (n = 182) |
|---|---|---|---|
| FISH Positive | 51 (62.2%) | 51 (11.5%) | 7 (3.9%) |
| FISH Equivocal | 5 (6.1%) | 35 (7.9%) | 9 (4.9%) |
| FISH Negative | 26 (31.7%) | 359 (80.7%) | 166 (91.2%) |
| Total Discordant | 31 (37.8%) | 410 (92.1%) | 16 (8.8%) |

HER2, human epidermal growth factor receptor 2;
IHC, immunohistochemistry;
FISH, fluorescence in situ hybridization.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components or multiple components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a microcontroller, field programmable gate array (FPGA) or an application-specific integrated circuit (ASIC)) to perform certain operations. A hardware module may also comprise programmable logic or circuitry (e.g., as encompassed within a processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a processor configured using software, the processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein can be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method can be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternative embodiments, using either current technology or technology developed after the filing date of this application.

What is claimed is:

1. A computer-implemented method of diagnosing HER2 status for a patient, the method comprising:
    obtaining human epidermal growth factor receptor 2 (HER2) status for a specimen from analysis of immunohistochemistry (IHC) image from a first sample of the patient by applying the IHC image to a trained IHC classification model;
    obtaining HER2 status for a specimen from analysis of fluorescence in-situ hybridization (FISH) image from a second sample of the patient by applying the FISH image to a trained FISH classification model;
    identifying discordant HER2 status result between the HER2 status obtained from the IHC image and the HER2 status obtained from the FISH image; and
    in response to the identification of discordant HER2 status, diagnosing HER2 status based on at least gene expression data from a third sample of the patient, wherein the trained IHC classification model and the trained FISH classification model are machine learning models.

2. The computer-implemented method of claim 1, further comprising generating a HER2 discordance status report indicating biologic pathways in gene expression data.

3. The computer-implemented method of claim 1, further comprising generating a HER2 discordance status report including an indication of a model of molecular subtype gene expression used to identify the discordant HER2.

4. The computer-implemented method of claim 3, wherein the model of molecular subtype gene expression comprises a linear gene expression model.

5. The computer-implemented method of claim 3, wherein the model of molecular subtype gene expression comprises a pathway gene expression model.

6. The computer-implemented method of claim 5, further comprising generating the HER2 discordance status report including a listing of pathways identified by the pathway gene expression model.

7. The computer-implemented method of claim 3, wherein the model of molecular subtype gene expression comprises a multiple gene linear regression gene expression model.

8. The computer-implemented method of claim 7, further comprising generating the HER2 discordance status report including a listing of genes identified by the multiple gene linear regression gene expression model.

9. The computer-implemented method of claim 1, further comprising generating a HER2 discordance status report indicating a molecular subtype determined from the gene expression data.

10. The computer-implemented method of claim 9, wherein the molecular subtype is a HR+subtype, a HR+/HER2+subtype, a HR−/HER2+subtype, or a HER2-subtype.

11. The computer-implemented method of claim 9, wherein the molecular subtype is a ER+, ER−, PR+, or PR−.

12. The computer-implemented method of claim 9, wherein the molecular subtype is a triple negative subtype.

13. The computer-implemented method of claim 1, further comprising adjusting a therapeutic treatment protocol based on the patterns in gene expression data.

14. The computer-implemented method of claim 1, wherein diagnosing HER2 status based on at least gene expression data from a third sample of the patient comprises:
    for each of a plurality of biological pathways in the gene expression data, determining a pathway score;
    preparing a summary score for the plurality of biological pathways, based upon the pathway score for each biological pathway; and
    comparing the summary score to one or more enrichment scores each associated with a pre-determined molecular subtype,
    wherein diagnosing HER2 status based on at least gene expression data from a third sample of the patient comprises determining a molecular subtype of the gene expression data as corresponding to the HER2 status, based on the comparison of the summary score and the one or more enrichment scores.

15. The computer-implemented method of claim 1, wherein the trained IHC classification model is trained with histopathology slide image data to classify HER2 status; and wherein the trained FISH classification model is trained with histopathology slide image data to classify HER2 status.

16. The computer-implemented method of claim 15, wherein the trained IHC classification model and the trained FISH classification model are convolutional neural networks.

17. The computer-implemented method of claim 15, further comprising, in response identifying discordant HER2 status result between the HER2 status from the IHC image and the HER2 status from the FISH image and diagnosing HER2 status based on the at least gene expression data from the third sample of the patient, providing the discordant HER2 status results and the diagnosed HER2 status based on the at least gene expression data to a hybrid classification model.

18. The computer-implemented method of claim 17, wherein the hybrid classification model comprises a convolutional neural network.

19. The computer-implemented method of claim 1, wherein the first sample, the second sample, and the third sample are from a single biopsy block.

20. The computer-implemented method of claim 19, wherein the first sample, the second sample, and the third sample are different slices from the biopsy block.

21. A system having a memory and a processor, the memory storing instructions, that when executed, cause the processor to:
- obtain human epidermal growth factor receptor 2 (HER2) status for a specimen from analysis of immunohistochemistry (IHC) image from a first sample of the patient using a trained IHC classification model;
- obtain HER2 status for a specimen from analysis of fluorescence in-situ hybridization (FISH) image from a second sample of the patient using a trained FISH classification model;
- identify discordant HER2 status result between the HER2 status obtained from the IHC image and the HER2 status obtained from the FISH image; and
- in response to the identification of discordant HER2 status, diagnose HER2 status based on at least gene expression data from a third sample of the patient,
- wherein the trained IHC classification model and the trained FISH classification model are machine learning models.

22. The system of claim 21, the memory storing further instructions, that when executed, cause the processor to: generate a HER2 discordance status report indicating biologic pathways in gene expression data.

23. The system of claim 21, the memory storing further instructions, that when executed, cause the processor to: generate a HER2 discordance status report including an indication of a model of molecular subtype gene expression used to identify the discordant HER2.

24. The system of claim 21, wherein model of molecular subtype gene expression comprises a linear gene expression model.

25. The system of claim 21, wherein the model of molecular subtype gene expression comprises a pathway gene expression model.

26. The system of claim 21, the memory storing further instructions, that when executed, cause the processor to: generate the HER2 discordance status report including a listing of pathways identified by the pathway gene expression model.

27. The system of claim 21, wherein the model of molecular subtype gene expression comprises a multiple gene linear regression gene expression model.

28. The system of claim 21, the memory storing further instructions, that when executed, cause the processor to: generate the HER2 discordance status report including a listing of genes identified by the multiple gene linear regression gene expression model.

29. The system of claim 21, the memory storing further instructions, that when executed, cause the processor to: generate a HER2 discordance status report indicating a molecular subtype determined from the gene expression data.

* * * * *